US008470803B2

(12) United States Patent
Akama et al.

(10) Patent No.: US 8,470,803 B2
(45) Date of Patent: Jun. 25, 2013

(54) BORON-CONTAINING SMALL MOLECULES

(75) Inventors: Tsutomu Akama, Sunnyvale, CA (US); Jacob J. Plattner, Orinda, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 289 days.

(21) Appl. No.: 13/062,466

(22) PCT Filed: Sep. 10, 2009

(86) PCT No.: PCT/US2009/055611
§ 371 (c)(1),
(2), (4) Date: Mar. 4, 2011

(87) PCT Pub. No.: WO2010/027975
PCT Pub. Date: Mar. 11, 2010

(65) Prior Publication Data
US 2011/0166103 A1 Jul. 7, 2011

Related U.S. Application Data

(60) Provisional application No. 61/094,405, filed on Sep. 4, 2008.

(51) Int. Cl.
*A61K 31/69* (2006.01)
*C07F 5/04* (2006.01)

(52) U.S. Cl.
USPC .................. 514/64; 546/13; 558/288

(58) Field of Classification Search
USPC .................. 514/64; 546/13; 558/288
See application file for complete search history.

(56) References Cited

U.S. PATENT DOCUMENTS

| | | | |
|---|---|---|---|
| 2,260,336 A | 10/1941 | Prescott, et al. |
| 3,686,398 A | 8/1972 | Kohn et al. |
| 3,873,279 A | 3/1975 | Singer |
| 4,602,011 A | 7/1986 | West et al. |
| 4,716,035 A | 12/1987 | Sampathkumar |
| 4,766,113 A | 8/1988 | West et al. |
| 4,894,220 A | 1/1990 | Nabi et al. |
| 4,919,934 A | 4/1990 | Deckner et al. |
| 5,348,947 A | 9/1994 | Patel et al. |
| 5,348,948 A | 9/1994 | Patel et al. |
| 5,591,731 A | 1/1997 | Kennedy et al. |
| 5,668,258 A | 9/1997 | Stolowitz |
| 5,688,928 A | 11/1997 | Stolowitz |
| 5,831,045 A | 11/1998 | Stolowitz et al. |
| 5,880,188 A | 3/1999 | Austin et al. |
| 5,962,498 A | 10/1999 | Driedger et al. |
| 6,083,903 A | 7/2000 | Adams et al. |
| 6,221,640 B1 | 4/2001 | Tao et al. |
| 6,306,628 B1 | 10/2001 | Rothschild et al. |
| 6,369,098 B1 | 4/2002 | Pershadsingh et al. |
| 6,521,619 B2 | 2/2003 | Link et al. |
| 6,800,645 B1 | 10/2004 | Cox et al. |
| 6,855,848 B2 | 2/2005 | Scherer et al. |
| 7,169,603 B2 | 1/2007 | Hedley et al. |
| 7,205,425 B2 | 4/2007 | Shibasaki et al. |
| 7,217,701 B2 | 5/2007 | Mikoshiba et al. |
| 7,390,806 B2 | 6/2008 | Lee et al. |
| 7,446,236 B2 | 11/2008 | Naud et al. |
| 7,465,836 B2 | 12/2008 | Lee et al. |
| 7,582,621 B2 | 9/2009 | Baker et al. |
| 7,767,657 B2 | 8/2010 | Baker et al. |
| 7,816,344 B2 | 10/2010 | Baker et al. |
| 8,039,450 B2 | 10/2011 | Akama et al. |
| 8,168,614 B2 | 5/2012 | Baker et al. |
| 2002/0028831 A1 | 3/2002 | Manley |
| 2002/0161230 A1 | 10/2002 | Meudt et al. |
| 2003/0032673 A1 | 2/2003 | Nagy |
| 2004/0077601 A1 | 4/2004 | Adams et al. |
| 2004/0224923 A1 | 11/2004 | Lee et al. |
| 2005/0054644 A1 | 3/2005 | Lee et al. |
| 2005/0125852 A1 | 6/2005 | Caenepeel et al. |
| 2006/0009386 A1 | 1/2006 | Stossel et al. |
| 2006/0222671 A1 | 10/2006 | Weidner |
| 2006/0234981 A1 | 10/2006 | Baker et al. |
| 2007/0155699 A1 | 7/2007 | Baker et al. |
| 2007/0286822 A1 | 12/2007 | Sanders et al. |
| 2007/0293457 A1 | 12/2007 | Baker et al. |
| 2009/0227541 A1 | 9/2009 | Baker et al. |
| 2010/0048570 A1 | 2/2010 | Kim et al. |
| 2010/0256092 A1 | 10/2010 | Xia et al. |

FOREIGN PATENT DOCUMENTS

| | | |
|---|---|---|
| EP | 0969531 | 1/2000 |
| EP | 1155698 A1 | 11/2001 |
| EP | 1 444 981 A1 | 8/2004 |
| WO | WO 9533754 | 5/1995 |
| WO | WO 9622023 | 7/1996 |
| WO | WO 9812206 A1 | 3/1998 |
| WO | WO 0027822 | 5/2000 |
| WO | WO 0044387 A1 | 8/2000 |
| WO | WO 0075142 A2 | 12/2000 |

(Continued)

OTHER PUBLICATIONS

Austin, et al., "Oxaboroles and Salts and their Use of Biocides for Plastics", CAS, vol. 124, pp. 234-024, (1996).

Bailey, et al., "Boron-Containing Antibacterial Agents: Effects on Growth and Morphology of Bacteria Under Various Culture Conditions," Antimicrobial Agents and Chemotherapy, 17(04):549-553, (Apr. 1980).

Baker, et al., "Discovery of New Boron-Containing Antifungal Agent, 5-Fluoro-1,3-dihydro-1-hydroxy-2, 1-benzoxaborole (AN2690) for Potential Treatment of Onychomoycosis", Journal of Medicinal Chemistry, vol. 49, No. 15; pp. 4447-4450, (Jul. 27, 2006).

Baker, et al., "Progress on New Therapeutics for Fungal Nail Infections", Annual Reports in Medicinal Chemistry, vol. 40: pp. 323-335, (2005).

Bessis, N., "Gene Therapy for Rheumatoid Arthritis," J. Gene Med, vol. 4; pp. 581-591 (2002).

(Continued)

Primary Examiner — Charanjit Aulakh
(74) Attorney, Agent, or Firm — Morgan, Lewis & Bockius LLP

(57) ABSTRACT

This invention provides, among other things, novel compounds useful for treating inflammatory conditions, pharmaceutical compositions containing such compounds, as well as combinations of these compounds with at least one additional therapeutically effective agent.

66 Claims, No Drawings

FOREIGN PATENT DOCUMENTS

| WO | WO 0114578 A1 | 3/2001 |
|---|---|---|
| WO | WO 0149303 A1 | 7/2001 |
| WO | WO 0187846 A2 | 11/2001 |
| WO | WO 0244184 | 6/2002 |
| WO | WO 03033002 A1 | 4/2003 |
| WO | WO 03059916 A2 | 7/2003 |
| WO | WO 2004056322 A2 | 7/2004 |
| WO | WO 2005013892 A3 | 2/2005 |
| WO | WO 2005123094 A2 | 12/2005 |
| WO | WO 2006007384 | 1/2006 |
| WO | WO 2006062731 A1 | 6/2006 |
| WO | WO 2006079843 A1 | 8/2006 |
| WO | WO 2006089067 A2 | 8/2006 |
| WO | WO 2006096131 A1 | 9/2006 |
| WO | WO 2007022437 A2 | 2/2007 |
| WO | WO 2007078340 A2 | 7/2007 |
| WO | WO 2007095638 A2 | 8/2007 |
| WO | WO 2007146965 A2 | 12/2007 |
| WO | WO 2008157726 A1 | 12/2008 |
| WO | WO 2009111676 A2 | 9/2009 |
| WO | WO 2009014309 A2 | 11/2009 |
| WO | WO 2009140309 A2 | 11/2009 |
| WO | WO 2010028005 A1 | 3/2010 |
| WO | WO 2010045503 A | 4/2010 |
| WO | WO 2010045505 A1 | 4/2010 |

OTHER PUBLICATIONS

Brown, et al., "Chiral Synthesis Via Organoboranes. 35. Simple Procedures for the Efficient Recycling of the Terpenyl Chiral Auxiliaries and Convenient Isolation of the Homoallylic Alcohols in Asymmetric Allyl- and Crotylboration of Aldehydes," J. Org. Chem., vol. 57, No. 24; pp. 6608-6614, (1992).

Cairns, et al., "Derivatives of 1,4-Xylene-2,5-diboronic acid and 1,4-xylene-2-boronic acid", J. Org. Chem. vol. 29; pp. 2810-2812, (1964).

Chander, et al. "Prevalence of Fungal Corneal Ulcers in Northern India", Infections, vol. 22, No. 3; pp. 207-209, (1994).

Chemical Abstracts Registry No. 845302-09-2, Entered STN Mar. 11, 2005.

Cui, et al., "Organoboron Compounds with an 8-Hydroxyquinolato Chelate and Its Derivatives: Substituent Effects on Structures and Luminescence," Inorganic Chemistry, vol. 44, No. 03; pp. 601-609, (Feb. 7, 2005).

Dale, et al., "Substituted Styrenes VIII Syntheses and some Reactions of the Vinylbenzeneboronic Acids" J. Org. Chem. vol. 27; pp. 2598-2603, (1962).

Denis, "Pharmacology 1104 Lecture: Drug Classifications & Characteristics of Antimicrobials" (2003).

Farfan, et al., "Through-Bond Modulation on N-B Ring Formation Shown by NMR and X-Ray Diffraction Studies of Borate Derivatives of Pyridyl Alcohols," J. Chem. Soc. Perkin Trans., vol. 2; pp. 527-532 (1992).

Ferrer, Targeting Aminocytl-tRNA Synthetases for the Treatment of Fungal Infections, Drug News Perspective, vol. 19, No. 6; pp. 347-348, (Jul./Aug. 2006).

Fungicide: Definition from Answer.com, (1998).

Grassberger, et al., "Degradation of 1,2-dihydro-1-hydroxy-2-(organosulfonyl)2,3,1-benzodiasaborines and -thieno[3,2-d][1,,3]diazaborines in Alkaline Aqueous Solutions", Liebigs Annalen Der Chemie, vol. 4; pp. 683-688, (1985).

Guo-Zheng, et al., "Single Site Transarylation of 2,2'-Dimetalized-1,1'-Binaphthyl to Aminocloroborates and Synthesis of 2-Binaphthyl Boron Compounds," Youji Huaxue/Organic Chemistry, Science Press, vol. 16, No. 02; pp. 139-144, (1996) (English Abstract).

Haynes, et al., "Arylboronic Acids VIII. Reactions of boronphthalide" J. Org. Chem. vol. 29, No. 11; pp. 3229-3233, (1964).

Hauck, et al., "Preparation and Anticonvulsant Activity of Some Arydialkkylsuccinimides" Research Lab of Parke Davis Co. (1967).

He, et al., "Small-Molecule Inhibition of TNF-alpha", Science, vol. 310, No. 5750; pp. 1022-1025, (Nov. 11, 2005).

Lampe, et al., "Synthesis and Protien Kinase Inhibitory Activity of Balanol Analogues with Modified Benzophenone Subunits", J. Med. Chem., vol. 45; pp. 2624-2643, (2002).

Lennarz, et al., "Arylboronic Acids. IV. Reactions of Boronophthalide" J. Am. Chem. Soc. vol. 82; pp. 2172-2175, (1960).

Li, et al., "An Improved Protocol for Preparation of 3-Pyridyl- and Some Arylboronic Acids", J. Org. Chem., vol. 67; pp. 5394-5397, (2002).

Koster, et al., "Cyclisierugen von Bor-Stickstoff-Verbindugen in der Hietz" Liebigs Ann. Chem., vol. 720; pp. 23-31, (1968).

Koster, et al., "Boron Compounds, XXXIX. Alkenoxy(diorgany)boranes Substituted at the Alkeonxy Group from 2-methylacrolein and triorganylboranes," Justus Liebigs Annalen Der Chemie, No. 06; pp. 1116-1134, (1976).

McMillin, et al., "Systemic Aspects of Psoriasis: An Intergrative Model Based on Intestinal Etiology", Int. Med. vol. 2, Issue 2/3, (1999).

Moeder, et al., "Kinetic Analysis of the Asymmetric Amplification exhibited by B-chlorodiisopinocampheylborane," Journal of Physical Organic Chemistry, vol. 17, No. 4; pp. 317-324, (Apr. 2004).

Morissette, et al., "High-throughput Crystallization: Polymorphs, Salts, Co-Crystals and Solvates of Pharmaceutical Solids", Advanced Drug Delivery Reviews, vol. 56; pp. 273-300, (2004).

Mudran, "Drug Delivery to the Nail Following Topical Application", International Journal of Pharmaceutics, vol. 236: pp. 1-26, (2002).

Patani, et al., "Bioterrorism: A Rational Approach to Drug Design", Chem. Rev., vol. 96; pp. 3147-3176 (1996).

Qin, et al., "Luminescent Organoboron Quinolate Polymers," Journal of the American Chemical Society, vol. 126, No. 22; pp. 7015-7018, (Jun. 9, 2004).

Rock, et al., "An Antifungal Agents Inhibits Aminoacyl-tRNA Synthetase by Trapping tRNA in the Editing Site", Science, vol. 316, No. 5832; pp. 1759-1761, (Jun. 22, 2007).

Snyder, et al. "Common Bacteria Whose Susceptibility to Antimicrobials in no longer Predictable" J. Med. Liban, vol. 48 No. 4; pp. 208-214, (2000).

Sugar, et al., "Comparison of Three Methods of Antifungal Susceptibility Testing with the Proposed NCCLS Stardard Broth Macrodilution Assay: Lack of Effect of Phenol Red" Diagn. Microbiol. Infect. Dis. vol. 21; pp. 129-133, (1995).

Tabuchi, et al., "Anticoccidial Activity of some Azacyclo Organoborinates," Heterocycles, vol. 60, No. 01; pp. 177-182, (2003).

Toporcer, et al., "Preparation and Properties of some Tetracoordinate Boron Compounds. The Pseudo-metal Ion Concept," Inorganic Chemistry, vol. 4, No. 11; pp. 649-1655, (Nov. 1965).

Trujillo, et al., "X-Ray Crystallographic Study of Boroxazolidones, Obtained from L-ornithine, L-methionine, Kainic acid and 2,6-pyridinedicarboxylic acid", Journal of Organometallic Chemistry, vol. 571; pp. 21-29; (1998).

Tschampel, et al., "Arylboronic Acids. VII. Some Reactions to o-Formybenzeneboronic Acids", J. Org. Chem. vol. 29, No. 8; pp. 2168-2172, (1964).

Turner, et al., Current Pharmaceutical Design, vol. 2; pp. 209-224 (1996).

Vippagunta, "Crystalline Solids", Advanced Drug Delivery Reviews, vol. 48; pp. 3-26, (2001).

Wang, et al., "Expression, Purification and Characterization of Human cAMP-Specific Phosphodiesterase (PDE4) Subtypes A, B, C, and D", Biochemical and Biophysical Research Communications, vol. 234; pp. 320-324, (1997).

Ye, et al., "Convenient and Versatile Synthesis of formyl-substituted Benzoxaboroles", Tetrahedron, vol. 65; pp. 8738-8744, (2009).

Zhdankin, et al., "Synthesis and Structure of Benzoboroxoles: Novel Organboron Heterocycles," Tetrahedron Letters, vol. 40; pp. 6705-6708, (1999).

Zhou, et al., "Hemodextrin: a Self-assembled Cyclodextrin-Porphyrin Construct That Binds Dioxygen," Biophysical Chemistry, 105:639-648 (2003).

Zhou, et al., "Structure-activity Studies on a Library of Potent Calix[4]arene-based PDGF Antagonists that Inhibit PDGF-stimulated PDGFR Tyrosine Phosphorylation," Org. Biomol. Chem., 4:2376-2386 (2006).

Zhou, et al., "Pattern Recognition of Proteins Based on an Array of Functionalized Porphyrins," J. Am. Chem. Soc., 128:2421-2425 (2006).

Zixing, et al., "Synthesis of Aromatic Nitrogen-containing Heterocyclic Derivatives of Asymmetric Diarylborinic Acids," Wuhan Daxue Xuebo-Wuhan University Journal, vol. 3; pp. 67-71, (1990), (English Abstract).

Adamczyk-Wozniac, et al., "Benzoxaboroles-Old Compounds with new applications", Journal of Organometalic Chemistry 694;3533-3541 (2009).

Akama, et al., "Discovery and structure-activity study of novel benzoxaborole anti-inflammatory agent (AN2728) for the potential topical treatment of psoriasis and atopic dermatitis", Bioorganic & Medicinal Chemistry Letters, (2009) 19: 2129-2132.

Alley, et al., "Recent Progress on Topical Therapy of Onychomycosis", Expert Opinion Investigate Drugs(Feb. 2007) 16(2): 157-67.

Baker, et al., "Identification of a Novel Boron-Containing Antibacterial Agent (AN0128) with Anti-inflammatory activity, for the Potential Treatment of Cutaneous Diseases", Bioorganic & Medicinal Chemistry Letters (2006) 16: 5963-5937.

Cusack, S., et al., "The 2 A Crystal Structure of leucyl-tRNA Synthetase and its Complex with a Leucyl-Adenylate Analogue." EMBO Journal, vol. 19; pp. 2351-2361, (2000).

Dian, "International Nomenclature of Organics", China Petrochemical Press, 1st Edition; 50-51 (Jan. 21, 2004).

Goodman, et al., "Goodman & Gilman's Manual of Pharmacology and Therapeutics" Chapter 40;681-694 (2008).

Hui, et al., "In Vitro Penetration of a Novel Oxaborole Antifungal (AN2690) into the Human Nail Plate", Journal of Pharmaceutical Sciences (2007) 96(10): 2622-2631.

Lee, K., et al., "Molecular Study of the Editing Active Site of *Escherichia coli* Leucyl-tRNA Synthetase: Two Amino Acid Binding Site in the Editing Domain", vol. 54; pp. 693-704, (2004).

Luan, et al., "Inhibition of Experimental Periodontitis by a topical boron-base antimicrobial" J Dent. Res, 87(2):148-152 (2008).

Perola, E., et al., "Successful Virtual Screening of a Chemical Database for Farnesltransferase Inhibitor Leads." vol. 43; pp. 401-4008, (2000).

Qin, Clinical Mycology, Fudan Press, Shanghai Medical University Press, pp. 92, 111, 340-41, 365, 437 and 487 (2001) With English Translation.

Silverman, "The Organic Chemistry of Drug Design and Drug Action", 2nd Edition, Northwestern University, Department of Chemistry, Evanston, Illinois, Section 2: 29-32 (2004).

Tatsumi, et al., "Therapeutic Efficacy of Topically applied KP-103 against Experimental Tinea Uguium in Guinea Pigs in Comparison with Amorolfine and Terbinafine", Antimicrobial Agents and Chemotherapy, vol. 46, No. 12; pp. 3797-3801 (2002).

Williams, et al., "Foye's Principles of Medicinal Chemistry", 5th Edition, 2002, Lippincoot Williams & Wilkins, p. 59.

"Structure-Activity Studies led to the Discovery of AN2898 in Development for Topical Treatment of Psoriasis and Atopic Dermatitis", Scientific Presentation at the American Academy of Dermatology Annual Meeting, San Francisco, CA Mar. 6-10, 2009.

"AN2898 Inhibits Cytokines Relevant to Topical Treatment of Psoriasis and Atopic Dermatitis", Scientific Presentation at the American Academy of Dermatology Annual Meeting, San Francisco, CA Mar. 6-10, 2009.

"AN2718 has Broad Spectrum Antifungal Activity Necessary for the Topical Treatment of Skin and Nail Fungal Infections", Scientific Presentation at the American Academy of Dermatology Annual Meeting, San Francisco, CA Mar. 6-10, 2009.

"AN2718 Demonstrates Significant Efficacy in Three Phase lb Psoriasis Microplaque Trials" Scientific Presentation at the American Academy of Dermatology Annual Meeting, San Francisco, CA Mar. 6-10, 2009.

"AN2728 Demonstrates Significant Safety and Efficacy in Phase IIa Double Blind Trial in Plaque Type Psoriasis", Scientific Presentation at the American Academy of Dermatology Annual Meeting, San Francisco, CA Mar. 6-10, 2009.

"AN2728 Preclinical Studies Demonstrate an Acceptable Safety Profile for the Topical Treatment of Psoriasis and Atopic Dermatitis", Scientific Presentation at the American Academy of Dermatology Annual Meeting, San Francisco, CA May 6-10, 2009.

"A New Class of Benzoxaborole-based Potent Antitrypanosomal Agents: Probing Effect of Different Linkage Groups in *Trypanosoma brucei* Growth Inhibition", Scientific Presentation at the American Society of Tropical Medicine and Hygiene Conference, New Orleans, LA Dec. 7-11, 2008.

"AN2920, A Novel Oxaborole, Shows In Vitro and In Vivo Activity Against *Trypanosomal brucei*", Scientific Presentation at the American Society of Tropical Medicine and Hygiene Conference, New Orleans, LA Dec. 7-11, 2008.

"A Novel Oxaborole, AN3520, Show Efficacy against Human African Trypanomiasis In Vitro and In Vivo, Including Promise in a Murine CNS Model of T. brucei Infection", Scientific Presentation at the American Society of Tropical Medicine and Hygiene Conference, New Orleans, LA Dec. 7-11, 2008.

"Antifungal Activity and Mechanism of Action of a Benzoxaborole, AN2718, which is in Development for the Treatment of Tinea Pedis", Scientific Presentation at the 48th Interscience Conference on Antimicrobial Agents and Chemotherapy, Washington, D.C. Oct. 25-28, 2008.

"AN2728 Ointment, a Novel Oxaborole with Anti-Inflammatory Activity, Demonstrates Safety and Significant Efficacy in a Phase lb Psoriasis Plaque Test", Scientific Presentation at Montagna Symposium on Biology of Skin, Gleneden Beach, OR, Oct. 2-6, 2008.

"Preclinical Toxicology of AN2728, a Novel Oxaborole in Development for the Topical Treatment of Psoriasis", Scientific Presentation at the International Investigative Dermatology Conference, Kyoto, Japan, May 14-18, 2008.

"AN2898, a Novel Oxaborole Compound with Anti-Inflammatory Activity: Mechanism of Action and in vitro Cytokine Inhibition", Scientific Presentation at the International Investigative Dermatology Conference, Kyoto, Japan, May 14-18, 2008.

"Structure-Activity Studies of AN2728 and AN2898, Novel Oxaborole Compounds with Anti-Inflammatory Activity", Scientific Presentation at the International Investigative Dermatology Conference, Kyoto, Japan, May 14-18, 2008.

"In Vitro Activity and Mechanism of Action of AN2728, a Novel Oxaborole in Development for Treatment of Psoriasis", Scientific Presentation at the International Investigative Dermatology Conference, Kyoto, Japan, May 14-18, 2008.

"AN2898, a Novel Oxaborole Compound with Anti-Inflammatory Activity: Results of in Vivo Efficacy and Preclinical Safety Studies", Scientific Presentation at the International Investigative Dermatology Conference, Kyoto, Japan, May 14-18, 2008.

"AN2728, a Novel Oxaborole in Development for Treatment of Psoriasis, Demonstrates Significant Activity in a Micro Plaque Study", Scientific Presentation at the International Investigative Dermatology Conference, Kyoto, Japan, May 14-18, 2008.

"Preclinical Toxicology of AN2728, a Novel Borinic Acid Ester with Anti-Inflammatory Activity", American Academy of Dermatology, 65th Annual Meeting, Washington, DC, Feb. 2-6, 2007.

"AN2728, a Novel Oxaborole with Broad-Spectrum in Vitro Anti-Inflammatory Activity", American Academy of Dermatology, 65th Annual Meeting, Washington, DC, Feb. 2-6, 2007.

"In Vitro Nail Penetration of AN2690, Effect of Vehicle and Co-Efficient of Efficacy", American Academy of Dermatology, 65th Annual Meeting, Washington, DC, Feb. 2-6, 2007.

"Interim Results of a Multi-Center Study to Evaluate the Safety and Efficacy of Topically Applied AN2690 5.0% and 7.5% Solutions for the Treatment of Onychomycosis of the Great Toenail", American Academy of Dermatology, 65th Annual Meeting, Washington, DC, Feb. 2-6, 2007.

"In vivo Nail Residence Time of AN2690, a Novel Broad-Spectrum Antifungal Agent in Development for the Topical Treatment of Onychomycosis", American Academy of Dermatology, 65th Annual Meeting, Washington, DC, Feb. 2-6, 2007.

"An Open-Label, Multi-dose Study of Absorption and Systemic Pharmacokinetics of AN2690 Applied as a 7.5% Solution to All Toenails of Adult Patients with Moderate to Severe Onychomycosis", American Academy of Dermatology, 65th Annual Meeting, Washington, DC, Feb. 2-6, 2007.

"Medicinal Chemistry Development of AN2728, A Novel Oxaborole in Development for the Topical Treatment of Psoriasis", American Academy of Dermatology, 65th Annual Meeting, Washington, DC, Feb. 2-6, 2007.

"Skin Penetration and Anti-Inflammatory Activity of AN2728, a Novel Oxaborole", American Academy of Dermatology, 65th Annual Meeting, Washington, DC, Feb. 2-6, 2007.

"Nail Penetration and Nail Concentration of AN2690, a Novel Broad-Spectrum Antifungal Agent in Development for the Topical Treatment of Onychomycosis", Scientific Presentation at the American Associate of Pharmaceutical Scientist, Annual Meeting, San Antonio, TX, Oct. 29-Nov. 2, 2006.

BORON-CONTAINING SMALL MOLECULES

CROSS-REFERENCE TO RELATED APPLICATIONS

This application claims the benefit of U.S. Provisional Pat. App. No. 61/094,405, filed Sep. 4, 2008, which is incorporated by reference in its entirety for all purposes.

BACKGROUND FOR THE INVENTION

Irregular inflammation is a major component of a wide range of human diseases. People suffering from degenerative disorders often exhibit excess levels of pro-inflammatory regulators in their blood. One type of such pro-inflammatory regulators are cytokines including IL-1α, β, IL-2, IL-3, IL-6, IL-7, IL-9, IL-12, IL-17, IL-18, IL-23, TNF-α, LT, LIF, Oncostatin, and IFNc1α, β, γ.

A non-limiting list of common medical problems that are directly caused by inflammatory cytokines include: arthritis where inflammatory cytokines can lead to lesions in the synovial membrane and destruction of joint cartilage and bone; kidney failure where inflammatory cytokines restrict circulation and damage nephrons; lupus where inflammatory cytokines exacerbate immune complex deposition and damage; asthma where inflammatory cytokines close the airway; psoriasis where inflammatory cytokines induce dermatitis; pancreatitis where inflammatory cytokines induce pancreatic cell injury; allergy where inflammatory cytokines induce vasopermeability and congestion; fibrosis where inflammatory cytokines attack traumatized tissue; surgical complications where inflammatory cytokines prevent healing; anemia where inflammatory cytokines attack erythropoietin production; and fibromyalgia where inflammatory cytokines are elevated in fibromyalgia patients.

Other diseases associated with chronic inflammation include cancer; heart attack where chronic inflammation contributes to coronary atherosclerosis; Alzheimer's disease where chronic inflammation destroys brain cells; congestive heart failure where chronic inflammation causes heart muscle wasting; stroke where chronic inflammation promotes thrombo-embolic events; and aortic valve stenosis where chronic inflammation damages heart valves. Arteriosclerosis, osteoporosis, Parkinson's disease, infection, inflammatory bowel disease including Crohn's disease and ulcerative colitis as well as multiple sclerosis (a typical autoimmune inflammatory-related disease) are also related to inflammation (Bebo, B. F., Jr., *J Neurosci Res*, 45: 340-348, (1996); Mennicken, F., *Trends Pharmacol Sci*, 20: 73-78, (1999); Watanabe, T, *Int J Cardiol*, 66 Suppl 1: S45-53; discussion S55, (1998); Sullivan, G. W., *J Leukoc Biol*, 67: 591-602, (2000); Franceschi, C., Ann N Y Acad Sci, 908: 244-254, (2000); Rogers, J, Ann N Y Acad Sci, 924: 132-135, (2000); Li, Y. J., Hum Mol Genet, 12: 3259-3267, (2003); Maccarrone, M., *Curr Drug Targets Inflamm Allergy*, 1: 53-63, (2002); Lindsberg, P. J., *Stroke*, 34: 2518-2532, (2003); DeGraba, T. J., *Adv Neurol*, 92: 29-42, (2003); Ito, H., *Curr Drug Targets Inflamm Allergy*, 2: 125-130, (2003); von der Thusen, J. H., *Pharmacol Rev*, 55: 133-166, (2003); Schmidt, M. I., *Clin Chem Lab Med*, 41: 1120-1130, (2003); Virdis, A., *Curr Opin Nephrol Hypertens*, 12: 181-187, (2003); Tracy, R. P., *Int J Clin Pract*, Suppl 10-17, (2003); Haugeberg, G., *Curr Opin Rheumatol*, 15: 469-475, (2003); Tanaka, Y., *J Bone Miner Metab*, 21: 61-66, (2003); Williams, J. D., *Clin Exp Dermatol*, 27: 585-590, (2002)). Some diseases in advanced stages can be life threatening. Several methodologies are available for the treatment of such inflammatory diseases; the results, however, are generally unsatisfactory as evidenced by a lack of efficacy and drug related side effects associated therewith.

Inflammatory Bowel Disease

Inflammatory bowel disease (IBD) comprises Crohn's disease (CD) and ulcerative colitis (UC), both of which are idiopathic chronic diseases occurring with an increasing frequency in many parts of the world. In the United States, more than 600,000 are affected every year. IBD can involve either small bowel, large bowel, or both. CD can involve any part of the gastrointestinal tract, but most frequently involves the distal small bowel and colon. It either spares the rectum, or causes inflammation or infection with drainage around the rectum. UC usually causes ulcers in the lower part of the large intestine, often starting at the rectum. Patients with IBD have defective intestinal epithelial barrier function, which allows bacterial colonization of the epithelia. As a result, bacterial products and pro-inflammatory cytokines (TNF-α, IL-1 and IL-6) cause persistent inflammatory stimulation. Bacterial antigens are introduced into the immune system by mucosal dendritic cells and macrophages. In response, intestinal phagocytes (mainly monocytes and neutrophils) proliferate and increase expression and secretion of pro-inflammatory cytokines Symptoms vary but may include diarrhea, fever, and pain. Patients with prolonged UC are at an increased risk of developing colon cancer. There is currently no satisfactory treatment, as the cause for IBD remains unclear although infectious and immunologic mechanisms have been proposed. IBD treatments aim at controlling inflammatory symptoms, conventionally using corticosteroids, aminosalicylates and standard immunosuppressive agents such as azathioprine (6-mercaptopurine), methotrexate and ciclosporine. Of these, the only disease-modifying therapies are the immunosuppressive agents azathioprine and methotrexate, both of which have a slow onset of action and only a moderate efficacy. Long-term therapy may cause liver damage (fibrosis or cirrhosis) and bone marrow suppression. Also patients often become refractory to such treatment. Other therapeutic regimes merely address symptoms (Rutgeerts, P. A, *J Gastroenterol Hepatol*, 17 Suppl: S176-185 (2002); Rutgeerts, P., *Aliment Pharmacol Ther*, 17: 185-192 (2003)).

Psoriasis

Psoriasis is one of the most common immune-mediated chronic skin diseases that comes in different forms and varied levels of severity, affecting approximately 2% of the population or more than 4.5 million people in the United States of which 1.5 million are considered to have a moderate to severe form of the disease. Ten to thirty percent of patients with psoriasis also develop a form of arthritis—psoriatic arthritis, which damages the bone and connective tissue around the joints. Psoriasis appears as patches of raised red skin covered by a flaky white buildup. It may also have a pimple-ish (pustular psoriasis) or burned (erythrodermic) appearance. Psoriasis may also cause intense itching and burning. Patients suffer psychologically as well as physically. Several modalities are currently available for treatment of psoriasis, including topical treatment, phototherapy, and systemic applications. However, they are generally considered to be only disease suppressive and disease modifying; none of them are curative. Moreover, many treatments are either cosmetically undesirable, inconvenient for long-term use, or associated with significant toxicity.

There are several types of psoriasis. Plaque psoriasis (psoriasis vulgaris) is the most common form of psoriasis. It affects 80 to 90% of people with psoriasis. Plaque psoriasis typically appears as raised areas of inflamed skin covered with silvery white scaly skin. These areas are called plaques.

Flexural psoriasis (inverse psoriasis) appears as smooth inflamed patches of skin. It occurs in skin folds, particularly around the genitals (between the thigh and groin), the armpits, under an overweight stomach (pannus), and under the breasts (inframammary fold). It is aggravated by friction and sweat, and is vulnerable to fungal infections. Guttate psoriasis is characterized by numerous small oval (teardrop-shaped) spots. These numerous spots of psoriasis appear over large areas of the body, such as the trunk, limbs, and scalp. Guttate psoriasis is associated with streptococcal throat infection. Pustular psoriasis appears as raised bumps that are filled with non-infectious pus (pustules). The skin under and surrounding pustules is red and tender. Pustular psoriasis can be localized, commonly to the hands and feet (palmoplantar pustulosis), or generalized with widespread patches occurring randomly on any part of the body. Nail psoriasis produces a variety of changes in the appearance of finger and toe nails. These changes include discoloring under the nail plate, pitting of the nails, lines going across the nails, thickening of the skin under the nail, and the loosening (onycholysis) and crumbling of the nail. Psoriatic arthritis involves joint and connective tissue inflammation. Psoriatic arthritis can affect any joint but is most common in the joints of the fingers and toes. This can result in a sausage-shaped swelling of the fingers and toes known as dactylitis. Psoriatic arthritis can also affect the hips, knees and spine (spondylitis). About 10-15% of people who have psoriasis also have psoriatic arthritis. Erythrodermic psoriasis involves the widespread inflammation and exfoliation of the skin over most of the body surface. It may be accompanied by severe itching, swelling and pain. It is often the result of an exacerbation of unstable plaque psoriasis, particularly following the abrupt withdrawal of systemic treatment. This form of psoriasis can be fatal, as the extreme inflammation and exfoliation disrupt the body's ability to regulate temperature and for the skin to perform barrier functions.

With increased understanding of the biological properties of psoriasis over the past two decades, biologic therapies targeting the activity of T lymphocytes and cytokines responsible for the inflammatory nature of this disease have become available. Currently, drugs prescribed for psoriasis include TNF-α inhibitors initially used for rheumatoid arthritis (RA) treatment, ENBREL® (etanercept), REMICADE® (infliximab) and HUMIRA® (adalimumab), and T-cell inhibitor AMEVIVE® (alefacept) from Biogen approved in 2002 and RAPTIVA® (efalizumab) from Genentech/Xoma approved in 2003 (Weinberg, J. M., *J Drugs Dermatol,* 1: 303-310, (2002)). AMEVIVE® (alefacept) is an immunoglobulin fusion protein composed of the first extracellular domain of human LFA-3 fused to the hinge, C(H)2 and C(H)3 domains of human IgG(1). It inhibits T cell proliferation through NK cells (Cooper, J. C., *Eur J Immunol,* 33: 666-675, (2003)). RAPTIVA® is also known as anti-CD11a, a humanized monoclonal antibody which targets the T cell adhesion molecule, leukocyte function-associated antigen-1 (LFA-1). Prevention of LFA-1 binding to its ligand (ICAM-1, intercellular adhesion molecule-1) inhibits lymphocyte activation and migration, resulting in a decreased lymphocyte infiltration, thereby limiting the cascade of events eventually leading to the signs and symptoms of psoriasis (Cather, J. C., *Expert Opin Biol Ther,* 3: 361-370, (2003)). Potential side effects for current TNF-α inhibitors of the prior art, however, are severe, including development of lymphoma (Brown, S. L., *Arthritis Rheum,* 46: 3151-3158, (2002)), worsening congestive heart failure, resulting in a serious infection and sepsis, and exacerbations of multiple sclerosis and central nervous system problems (Weisman, M. H., *J Rheumatol Suppl,* 65: 33-38, (2002); Antoni, C., *Clin Exp Rheumatol,* 20: S152-157, (2002)). While side effects of the T-cell inhibitor of AMEVIVE®/RAPTIVA® may be more tolerable in psoriasis treatment, RAPTIVA® is an immunosuppressive agent. Immunosuppressive agents have the potential to increase the risk of infection, reactivate latent, chronic infections or increase the risk of cancer development.

Although many advances have been made in the understanding of the biological properties of psoriasis over the past two decades and an unconventional treatment for psoriasis has become available as described above, much of the suffering it produces is still not adequately addressed. A survey of over 40,000 American patients with psoriasis performed by the National Psoriasis Foundation in 1998 showed 79% of the younger patients felt frustrated by the ineffectiveness of their treatment. Of those with severe disease, 32% felt their treatment was not aggressive enough (Mendonca, C. O., *Pharmacol Ther,* 99: 133-147, (2003); Schon, M. P., *J Invest Dermatol,* 112: 405-410, (1999)).

Rheumatoid Arthritis

Rheumatoid arthritis (RA) represents another example of troublesome inflammatory disorders. It is a common chronic inflammatory-related disease characterized by chronic inflammation in the membrane lining (the synovium) of the joints and/or other internal organs. The inflammatory cells can also invade and damage bone and cartilage. The joint involved can lose its shape and alignment, resulting in loss of movement. Patients with RA have pain, stiffness, warmth, redness and swelling in the joint, and other systemic symptoms like fever, fatigue, and anemia. Approximately 1% of the population or 2.1 million in the U.S. are currently affected, of which more are women (1.5 million) than men (0.6 million). The pathology of RA is not fully understood although the cascade of improper immunological reactions has been postulated as a mechanism. Conventional treatment is unfortunately inefficient in RA (Bessis, N., *J Gene Med,* 4: 581-591, (2002)) (29). The disease does not respond completely to symptomatic medications including corticosteroids and non-steroidal anti-inflammatory drugs (NSAIDs) used since the 1950s. Also, these medications carry a risk of serious adverse effects. The therapeutic effects of the disease-modifying anti-rheumatic drugs (DMARDs) such as Methotrexate (MTX) are often inconsistent and short-lived.

The role of the cytokine network in mediating inflammation and joint destruction in RA has been extensively investigated in recent years. In addition to TNF-α, IL-1 plays a pivotal role in the pathogenesis and the clinical manifestations of RA (54). The ability of IL-1 to drive inflammation and joint erosion and to inhibit tissue repair processes has been clearly established in in vitro systems and in animal models, and alleviation of inflammatory symptoms in RA patients has been achieved by blockage of IL-1 (Bresnihan, B., *Arthritis Rheum,* 41: 2196-2204, (1998)). IL-6 is a multifunctional cytokine that regulates the immune response, hematopoiesis, the acute phase response, and inflammation. Deregulation of IL-6 production is implicated in the pathology of several diseases including RA. A therapeutic approach to block the IL-6 signal has been carried out by using humanized anti-IL-6R antibody for RA among other diseases (Ito, H., *Curr Drug Targets Inflamm Allergy,* 2: 125-130, (2003); Ishihara, K *Cytokine Growth Factor Rev,* 13: 357-368, (2002)). IL-10 is an anti-inflammatory cytokine Expressing IL-10 has been shown to prevent arthritis or ameliorate the disease in animal models (57, 58). While it is obvious that cytokines such as TNF-α, IL-1, IL-6 and IL-10 have independent roles, they act in concert in mediating certain pathophysiological processes in RA. The finding of a class of molecules described in this invention, which are able to modulate these different cytokines, will result in dramatic therapeutic progress in the treatment of RA.

A new class of biologic DMARDs (disease-modifying antirheumatic drugs) for the treatment of RA has recently been developed based on an understanding of the role of cytokines, TNF-α and IL-1, in the inflammatory process. The FDA has approved several such DMARDs including ENBREL® (etanercept) from Immunex/Amgen Inc. in 1998, REMICADE® (infliximab) from Centocor/Johnson & Johnson, HUMIRA® (adalimumab) from Abbott Laboratories Inc. in 2002, and KINERET® (anakinra) from Amgen in 2001. ENBREL® is a soluble TNF receptor (TNFR) recombinant protein. REMICADE® is a humanized mouse (chimeric) anti-TNF-α monoclonal antibody. HUMIRA® is a fully human anti-TNF monoclonal antibody created using phage display technology resulting in an antibody with human-derived heavy and light chain variable regions and human IgG1:k constant regions. All these 3 protein-based drugs target and bind to TNF-α to block the effects of TNF-α. KINERET® is a recombinant IL-1 receptor antagonist, which is similar to native human IL-1Ra, except for the addition of a single methionine residue at its amino terminus. KINERET® blocks the biologic activity of IL-1 by competitively inhibiting IL-1 binding to the IL-1 type I receptor (IL-1RI) and consequently reducing the pro-inflammatory effects of IL-1.

Multiple Sclerosis

Multiple Sclerosis (MS) is an autoimmune disease diagnosed in 350,000 to 500,000 people in the United States. Multiple areas of inflammation and loss of myelin in the brain and spinal cord signify the disease. Patients with MS exhibit varied degrees of neurological impairment depending on the location and extent of the loss of the myelin. There is evidence that the expression of chemokines (IL-8 family members) during CNS autoimmune inflammation is regulated by some pro-inflammatory cytokines, such as TNF (Glabinski, A. R., *Scand J Immunol*, 58: 81-88, (2003)). The roles of other pro-/anti-inflammatory cytokines such as IL-1β, IL-6 and IL-10 were also confirmed in EAE animal models (Diab, A., *J Neuropathol Exp Neurol*, 56: 641-650, (1997); Samoilova, E. B., *J Immunol*, 161: 6480-6486, (1998); Robertson, J., *J Cell Biol*, 155: 217-226, (2001)) as well as in humans (de Jong, B. A., *J Neuroimmunol*, 126: 172-179, (2002)). IL-1β is present in MS lesions. IL-1 receptor antagonist (IL-1Ra) moderates the induction of experimental autoimmune encephalomyelitis (EAE). Increased risk of MS has been seen in individuals with High IL-1 (3 over IL-1Ra production ratio and high TNF over IL-10 production ratio (de Jong, B. A., *J Neuroimmunol*, 126: 172-179, (2002)). Common symptoms of MS include fatigue, weakness, spasticity, balance problems, bladder and bowel problems, numbness, vision loss, tremors and depression. Current treatment of MS only alleviates symptoms or delays the progression of disability, and several new treatments for MS including stem cell transplantation and gene therapy are conservatory (Fassas, A., *Blood Rev*, 17: 233-240, (2003); Furlan, R., *Curr Pharm Des*, 9: 2002-2008, (2003)). While anti-TNF antibodies have shown protective effects in experimental autoimmune encephalomyelitis (EAE), they aggravate the disease in MS patients, suggesting that inhibition of TNF-α alone is not sufficient (Ghezzi, P., *Neuroimmunomodulation*, 9: 178-182, (2001)).

Neurodegenerative Disorders

Alzheimer's disease (AD) and Parkinson's disease (PK) are the two most common neurodegenerative disorders. AD seriously affects a person's ability to carry out daily activities. It involves the parts of the brain that control thought, memory, and language. About 4 million Americans, usually after age 60, are estimated to suffer from AD.

PK is a progressive disorder of the central nervous system affecting over 1.5 million people in the United States. Clinically, the disease is characterized by a decrease in spontaneous movements, gait difficulty, postural instability, rigidity and tremor. PK is caused by the degeneration of the pigmented neurons in the substantia nigra of the brain, resulting in decreased dopamine availability. The causes of these neurodegenerative disorders are unknown and there is currently no cure for the disease.

Thus, novel approaches for the treatment of the above and other inflammatory-related diseases are needed. Although inflammatory-related disease mechanisms remain unclear and often vary from each other, dysfunction of the immune system caused by deregulation of cytokines has been demonstrated to play an important role in the initiation and progression of inflammation (Schon, M. P., *J Invest Dermatol*, 112: 405-410, (1999); Andreakos, E. T., *Cytokine Growth Factor Rev*, 13: 299-313, (2002); Najarian, D. J., *J Am Acad Dermatol*, 48: 805-821, (2003)).

Post-Radiotherapy Related Inflammation:

Radiation damage related inflammatory diseases to the rectum and sigmoid colon are most common complications with radiation therapy for cancers in the pelvic region, which include cancers of the cervix, uterus, prostate, bladder, and testes. Radiation proctosigmoiditis is the most common clinically apparent form of colonic damage after pelvic irradiation with an incidence of 5% to 20%. Patients typically exhibit symptoms of tenesmus, bleeding, low-volume diarrhea, and rectal pain. Rarely, low-grade obstruction or fistulous tracts into adjacent organs may develop.

Cytokines can be generally classified into 3 types: pro-inflammatory (IL-1α, β, IL-2, IL-3, IL-6, IL-7, IL-9, IL-12, IL-17, IL-18, IL-23, TNF-α, LT, LIF, Oncostatin, and IFNc1α, β, γ); anti-inflammatory (IL-4, IL-10, IL-11, W-13 and TGF-β); and chemokines (IL-8, Gro-α, MIP-1, MCP-1, ENA-78, and RANTES).

Tumor necrosis factor-α (TNF-α) and interleukin-1 (IL-1) are proinflammatory cytokines that mediate inflammatory responses associated with infectious agents and other cellular stresses. Overproduction of cytokines such as IL-1 and TNF-α is believed to underlie the progression of many inflammatory diseases including rheumatoid arthritis (RA), Crohn's disease, inflammatory bowel disease, multiple sclerosis, endotoxin shock, osteoporosis, Alzheimer's disease, congestive heart failure, and psoriasis among others (Dinarello, C. A. et al., *Rev. Infect. Diseases* 1984, 6:51; Salituro et al., *Curr. Med. Chem.* 1999, 6:807-823; Henry et al., *Drugs Fut.* 1999, 24:1345-1354). An accepted therapeutic approach for potential drug intervention in these conditions is the reduction of proinflammatory cytokines such as TNF-α (also referred to as TNFa) and interleukin-1β (IL-1b).

Phosphodiesterase4

The cyclic nucleotide specific phosphodiesterases (PDEs) represent a family of enzymes that catalyze the hydrolysis of various cyclic nucleoside monophosphates (including cAMP and cGMP). These cyclic nucleotides act as second messengers within cells, and as messengers, carry impulses from cell surface receptors having bound various hormones and neurotransmitters. PDEs act to regulate the level of cyclic nucleotides within cells and maintain cyclic nucleotide homeostasis by degrading such cyclic mononucleotides resulting in termination of their messenger role.

PDE enzymes can be grouped into eleven families according to their specificity toward hydrolysis of cAMP or cGMP, their sensitivity to regulation by calcium, calmodulin or cGMP, and their selective inhibition by various compounds. For example, PDE 1 is stimulated by $Ca^{2+}$/calmodulin. PDE 2 is cGMP-dependent, and is found in the heart and adrenals. PDE 3 is cGMP-dependent, and inhibition of this enzyme creates positive inotropic activity. PDE 4 is cAMP specific, and its inhibition causes airway relaxation, antiinflammatory and antidepressant activity. PDE 5 appears to be important in regulating cGMP content in vascular smooth muscle, and therefore PDE 5 inhibitors may have cardiovascular activity. Since the PDEs possess distinct biochemical properties, it is likely that they are subject to a variety of different forms of regulation.

PDE4 is distinguished by various kinetic properties including low Michaelis constant for cAMP and sensitivity to certain drugs. The PDE4 enzyme family consists of four genes, which produce 4 isoforms of the PDE4 enzyme designated PDE4A, PDE4B, PDE4C, and PDE4D [See: Wang et al., Expression, Purification, and Characterization of human cAMP-Specific Phosphodiesterase (PDE4) Subtypes A, B, C, and D, Biochem. Biophys. Res. Comm., 234, 320 324 (1997)] In addition, various splice variants of each PDE4 isoform have been identified.

PDE4 isoenzymes are localized in the cytosol of cells and are unassociated with any known membranous structures. PDE4 isoenzymes specifically inactivate cAMP by catalyzing its hydrolysis to adenosine 5'-monophosphate (AMP). Regulation of cAMP activity is important in many biological processes, including inflammation and memory Inhibitors of PDE4 isoenzymes such as rolipram, piclamilast, CDP-840 and ariflo are powerful antiinflammatory agents and therefore may be useful in treating diseases where inflammation is problematic such as asthma or arthritis. Further, rolipram improves the cognitive performance of rats and mice in learning paradigms.

Epidermal Growth Factor or EGF

The epidermal growth factor receptor (EGFR; ErbB-1; HER1 in humans) is the cell-surface receptor for members of the epidermal growth factor family (EGF-family) of extracellular protein ligands. The epidermal growth factor receptor is a member of the ErbB family of receptors. Mutations affecting EGFR expression or activity could result in cancer.

EGFR (epidermal growth factor receptor) exists on the cell surface and is activated by binding of its specific ligands, including epidermal growth factor and transforming growth factor α (TGFα).

Upon activation by its growth factor ligands, EGFR undergoes a transition from an inactive monomeric form to an active homodimer—although there is some evidence that preformed inactive dimers may also exist before ligand binding. In addition to forming homodimers after ligand binding, EGFR may pair with another member of the ErbB receptor family, such as ErbB2/Her2/neu, to create an activated heterodimer. There is also evidence to suggest that clusters of activated EGFRs form, although it remains unclear whether this clustering is important for activation itself or occurs subsequent to activation of individual dimers.

EGFR dimerization stimulates its intrinsic intracellular protein-tyrosine kinase activity. As a result, autophosphorylation of several tyrosine (Y) residues in the C-terminal domain of EGFR occurs. These include Y992, Y1045, Y1068, Y1148 and Y1173 as shown in the diagram to the left. This autophosphorylation elicits downstream activation and signaling by several other proteins that associate with the phosphorylated tyrosines through their own phosphotyrosine-binding SH2 domains. These downstream signaling proteins initiate several signal transduction cascades, principally the MAPK, Akt and JNK pathways, leading to DNA synthesis and cell proliferation. Such proteins modulate phenotypes such as cell migration, adhesion, and proliferation. The kinase domain of EGFR can also cross-phosphorylate tyrosine residues of other receptors it is aggregated with, and can itself be activated in that manner.

HM74A

HM74A or GPR109A is a G protein-coupled receptor for niacin. It couples to Gi alpha subunit. HM74A is known to be involved in the biosynthesis of niacin.

Histamine

Histamine is a biogenic amine involved in local immune responses as well as regulating physiological function in the gut and acting as a neurotransmitter. Histamine exerts its actions by combining with specific cellular histamine receptors. The four histamine receptors that have been discovered are designated H1 through H4. H1 is found on smooth muscle, endothelium and central nervous system tissue. H1 receptors cause vasodilation, bronchoconstriction, smooth muscle activation, separation of endothelial cells (responsible for hives) and pain and itching due to insect stings. H1 is also a primary receptor for allergic rhinitis symptoms and motion sickness. H2 is located on parietal cells and is primarily involved in gastric acid secretion. H3 is implicated with decreased neurotransmitter release. H4 has an unknown physiological role and is found primarily in the thymus, small intestine, spleen and colon, as well as basophils and bone marrow.

Beta-2 Adrenergic Receptor

The beta-2 adrenergic receptor ($β_2$ adrenoreceptor), also known as ADRB2, is a beta-adrenergic receptor, and also denotes the human gene encoding it. This receptor is directly associated with one of its ultimate effectors, the class C L-type calcium channel $Ca_v 1.2$. This receptor-channel complex also contains a G protein-$G_s$, which activate an adenylyl cyclase, cAMP-dependent kinase, and the counterbalancing phosphatase, PP2A. The assembly of the signaling complex provides a mechanism that ensures specific and rapid signaling by this G protein-coupled receptor. A two-state biophysical and molecular model has been proposed to account for the pH and REDOX sensitivity of this and other GPCRs. The beta-2 adrenergic receptor is involved with smooth muscle relaxation in the uterus. The beta-2 adrenergic receptor is involved with the digestion in the GI tract. The beta-2 adrenergic receptor is also involved with smooth muscle relaxation, dilation of blood vessels (such as coronary arteries, hepatic arteries and arteries to skeletal muscles). The beta-2 adrenergic receptor is also involved with striated muscle relaxation.

$K_{ATP}$ $K_{ATP}$ is implicated in the control of insulin release.

Protein Kinase C

Protein kinase C is a family of protein kinases consisting of ~10 isozymes. They are divided into three subfamilies, based on their second messenger requirements: conventional (or classical), novel, and atypical. Conventional (c)PKCs contain the isoforms α, $β_I$, $β_{II}$, and γ. These require $Ca^{2+}$, diacylglycerol (DAG), and a phospholipid such as phosphatidylcholine for activation. Novel (n)PKCs include the δ, ε, η, and θ isoforms, and require DAG, but do not require $Ca^{2+}$ for activation. Thus, conventional and novel PKCs are activated through the same signal transduction pathway as phospholipase C. On the other hand, atypical (a)PKCs (including protein kinase Mξ and ι/λ isoforms) require neither $Ca^{2+}$ nor diacylglycerol for activation. The term "protein kinase C" usually refers to the entire family of isoforms. PKC phosphorylates other proteins, altering their function. PKC is usually involved in smooth muscle contraction. In the vascular system, PKC is involved in vasoconstriction. In the bronchial system, PKC is involved in bronchoconstriction.

Protein Kinase A

Protein kinase A is a family of enzymes whose activity is dependent on the level of cyclic AMP (cAMP) in the cell. PKA is also known as cAMP-dependent protein kinase). Protein kinase A has several functions in the cell, including regulation of glycogen, sugar, and lipid metabolism. Each PKA is a holoenzyme that consists of two regulatory and two catalytic subunits. Under low levels of cAMP, the holoenzyme remains intact and is catalytically inactive. When the concentration of cAMP rises (e.g. activation of adenylate cyclases by G protein-coupled receptors coupled to $G_s$, inhibition of phosphodiesterases which degrade cAMP), cAMP binds to the two binding sites on the regulatory subunits, which leads to the release of the catalytic subunits. The free catalytic subunits can then catalyze the transfer of ATP terminal phosphates to protein substrates at serine, or threonine residues. This phosphorylation usually results in a change in activity of the substrate. Since PKAs are present in a variety of cells and act on different substrates, PKA and cAMP regulation are involved in many different pathways. PKA is usually influenced by cAMP. Also, the catalytic subunit itself can be regulated by phosphorylation. Downregulation of protein kinase A occurs by a feedback mechanism: one of the substrates that is activated by the kinase is a phosphodiesterase, which quickly converts cAMP to AMP, thus reducing the amount of cAMP that can activate protein kinase A. In adipocytes, PKA in involved with lipolysis. In myocytes, PKA in involved with the production of glucose as well as vasodilation.

Protease Activated Receptor1

Protease-activated receptors are a subfamily of related G protein-coupled receptors that are activated by cleavage of part of their extracellular domain. They are highly expressed in platelets, but also on endothelial cells, myocytes and neurons. PAR's are activated by the action of serine proteases such as thrombin (acts on PAR1) and trypsin. These enzymes cleave the N-terminus of the receptor, which in turn acts as a tethered ligand. In the cleaved state, part of the receptor itself acts as the agonist, causing a physiological response.

Most of the PAR family act through the actions of G-proteins i (cAMP inhibitory), 12/13 (Raf/Ras activation) and q (calcium signaling) to cause cellular actions.

TLR 3

TLR 3 is a member of the Toll-like receptor family of pattern recognition receptors of the innate immune system. Discovered in 2001, TLR3 recognizes double-stranded RNA, a form of genetic information carried by some viruses such as reoviruses. Upon recognition, TLR 3 induces the activation of NF-kB to increase production of type I interferons which signal other cells to increase their antiviral defenses. Double-stranded RNA is also recognized by the cytoplasmic receptors RIG-I and MDA-5. TLR3 has also been designated as CD283 (cluster of differentiation 283).

Compounds which can inhibit the biological moieties described above, or treat diseases involving those biological moieties, would be a significant advance in the art.

SUMMARY OF THE INVENTION

In a first aspect, the invention provides a compound of the invention. In an exemplary embodiment, the compound is a compound described herein or a pharmaceutically acceptable salt thereof. In an exemplary embodiment, the compound is according to a formula described herein.

In a first aspect, the invention provides a compound having a structure according to the following formula:

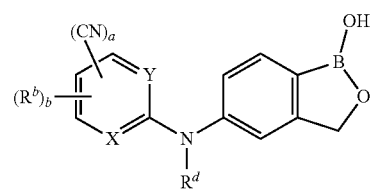

wherein X is selected from the group consisting of CH, C(CN), $CR^b$ and N; Y is selected from the group consisting of CH, C(CN), $CR^b$ and N; a is 0 or 1; b is 0 or 1; $R^d$ is selected from the group consisting of H, unsubstituted $C_1$-$C_6$ alkyl, $COR^{10}$, and —C(O)$OR^{10}$, wherein $R^{10}$ is selected from the group consisting of H and unsubstituted $C_1$-$C_6$ alkyl; with the proviso that when X or Y is C(CN), then a is 0; with the proviso that when X or Y is $CR^b$, then b is 0; with the proviso that X and Y cannot both be C(CN); with the proviso that X and Y cannot both be $CR^b$; $R^b$ is selected from the group consisting of $OR^4$, $NR^4R^5$, $SR^4$, —S(O)$R^4$, —S(O)$_2R^4$, —S(O)$_2NR^4R^5$, —C(O)$R^4$, —C(O)$OR^4$, —C(O)$NR^4R^5$, nitro, cyano, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein $R^4$ and $R^5$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, with the proviso that that $R^4$ and $R^5$, together with the atoms to which they are attached, are optionally combined to form a 5- to 7-membered substituted or unsubstituted heterocycloalkyl ring, or a salt thereof.

In another aspect, the invention provides a pharmaceutical formulation comprising: a) the compound of the invention, or a salt thereof; and b) a pharmaceutically acceptable excipient.

In another aspect, the invention provides a method of decreasing the release of a cytokine or a chemokine, the method comprising: contacting a cell with the compound of the invention, wherein the release of the cytokine or chemokine by the cell is decreased.

In another aspect, the invention provides a method of treating a condition in an animal, the method comprising administering to the animal a therapeutically effective amount of the compound of the invention, thereby treating the condition.

The invention also provides methods of making the compounds described herein.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: aq. is aqueous; AcOH is acetic acid; ACTBr is cetyltrimethylammonium bromide; B₂pin₂-bis(pinacolato)diboron; Boc is tert-butoxy carbonyl; Boc₂O-di-tert-butyl dicarbonate; BzOOH-benzoyl peroxide; Cs₂CO₃ is cesium carbonate; DABCO is 1,4-diazabicyclo[2.2.2]octane; DCM is dichloromethane or methylene chloride; DIAD is diisopropyl azodicarboxylate; DIEA is diisopropylethylamine; N,N-Diisopropylethylamine is DIPEA; DMAP is 4-(dimethylamino)pyridine; DME is 1,2-dimethoxyethane; DMF is N,N-dimethylformamide; DMSO is dimethylsulfoxide; eq. is equivalent; EtOAc is ethyl acetate; EtOH is ethanol; Et₂O is diethyl ether; EDCI-N-(3-dimethylaminopropyl)-N'-ethylcarbodiimide hydrochloride; m-CPBA-3-chloroperoxybenzoic acid; equiv-equivalent; h is hours; HATU is O-(7-azabenzotriazol-1-yl)-N,N,N',N'-tetramethyluronium hexafluorophosphate; HCl is hydrochloric acid; HPLC is high pressure liquid chromatography; ISCO Companion is automated flash chromatography equipment with fraction analysis by UV absorption available from Presearch; KOAc is potassium acetate; K₂CO₃ is potassium carbonate; LiAlH₄ or LAH is lithium aluminum hydride; LDA is lithium diisopropylamide; LHMDS is lithium bis(trimethylsilyl)amide; KHMDS is potassium bis(trimethylsilyl)amide; LiOH is lithium hydroxide; m-CPBA is 3-chloroperoxybenzoic acid; MeCN is acetonitrile; MeOH is methanol; MgSO₄ is magnesium sulfate; mins or min is minutes; Mp or MP is melting point; NaCNBH₃ is sodium cyanoborohydride; NaOH is sodium hydroxide; Na₂SO₄ is sodium sulfate; NH₄Cl is ammonium chloride; N₂ is nitrogen; NMM-N-methylmorpholine; n-BuLi is n-butyllithium; overnight is O/N; PdCl₂(pddf) is 1,1'-Bis(diphenylphosphino)ferrocene] dichloropalladium(II); PrOH is 1-propanol; iPrOH is 2-propanol; POCl₃ is phosphorus chloride oxide; RT or rt is room temperature; TFA is trifluoroacetic acid; Tf₂O is trifluoromethanesulfonic anhydride; THF is tetrahydrofuran; THP-tetrahydropyranyl; TMSI is trimethylsilyl iodide; H₂O is water; Ac-acetyl; PTSA-para-toluene sulfonic acid; Pyr.-Pyridine; Cbz-benzyloxycarbonyl; PMB-p-methoxybenzyl; DHP-dihydropyran; CSA-camphor sulfonic acid; CTAB-cetyltrimethylammonium bromide; sat.-saturated; Cy-cyclohexyl; Ph-phenyl; Ar-aryl.

"Compound of the invention," as used herein refers to the compounds discussed herein, salts (such as pharmaceutically acceptable salts), prodrugs, solvates and hydrates of these compounds.

"Inhibiting" and "blocking," are used interchangeably herein to refer to the partial or full blockade of the expression of a pro-inflammatory cytokine by a method of the invention, which leads to a decrease in the amount of the cytokine in the animal.

Where substituent groups are specified by their conventional chemical formulae, written from left to right, they equally encompass the chemically identical substituents, which would result from writing the structure from right to left, e.g., —CH₂O— is intended to also recite —OCH₂—.

The term "poly" as used herein means at least 2. For example, a polyvalent metal ion is a metal ion having a valency of at least 2.

"Moiety" refers to the radical of a molecule that is attached to another moiety.

The symbol , whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C₁-C₁₀ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "unsubstituted alkyl" encompasses straight or branched chain saturated hydrocarbon radicals. Examples of saturated hydrocarbon radicals include, but are not limited to, groups such as methyl, ethyl, n-propyl, isopropyl, n-butyl, t-butyl, isobutyl, sec-butyl, n-pentyl.

The term "alkylene" by itself or as part of another substituent means a divalent radical derived from an alkane, as exemplified, but not limited, by —CH₂CH₂CH₂CH₂—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —CH₂—CH₂—O—CH₃, —CH₂—CH₂—NH—CH₃, —CH₂—CH₂—N(CH₃)—CH₃, —CH₂—S—CH₂—CH₃, —CH₂—CH₂, —S(O)—CH₃, —CH₂—CH₂—S(O)₂—CH₃, —CH=CH—O—CH₃, —CH₂—CH=N—OCH₃, and —CH=CH—N(CH₃)—CH₃. Up to two heteroatoms may be consecutive, such as, for example, —CH₂—NH—OCH₃. Similarly, the term "heteroalkylene" by itself or as part of another substituent means a divalent radical derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written.

For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, 6-quinolyl, dioxaborolane, dioxaborinane and dioxaborepane. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes those radicals in which an aryl group is attached through the next moiety to the rest of the molecule. Thus, the term "arylalkyl" is meant to include those radicals in which an aryl group is attached to an alkyl group (e.g., benzyl, 1-(3-nitrophenyl)ethyl and the like). A substituent such as benzyl or 1-(3-nitrophenyl)ethyl can also be represented by 'substituted alkyl' wherein the ethyl radical is substituted with a 3-nitrophenyl moiety. The term "aryloxy" is meant to include those radicals in which an aryl group is attached to an oxygen atom. The term "aryloxyalkyl" is meant to include those radicals in which an aryl group is attached to an oxygen atom which is then attached to an alkyl group (e.g., phenoxymethyl, 3-(1-naphthyloxy)propyl, and the like).

For brevity, the term "heteroaryl" when used in combination with other terms (e.g., heteroaryloxy, heteroarylthioxy, heteroarylalkyl) includes those radicals in which a heteroaryl group is attached through the next moiety to the rest of the molecule. Thus, the term "heteroarylalkyl" is meant to include those radicals in which a heteroaryl group is attached to an alkyl group (e.g., pyridylmethyl and the like). The term "heteroaryloxy" is meant to include those radicals in which a heteroaryl group is attached to an oxygen atom. The term "heteroaryloxyalkyl" is meant to include those radicals in which an aryl group is attached to an oxygen atom which is then attached to an alkyl group. (e.g., 2-pyridyloxymethyl and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""—C(NR'R")=NR'", —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to (2m'+1), where m' is the total number of carbon atoms in such radical. R', R", R'", R"" and R""' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'", R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O) CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""—C(NR'R")=NR'", —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", R"" and R""' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R""' groups when more than one of these groups is present.

Two of the substituents on adjacent atoms of the aryl or heteroaryl ring may optionally be replaced with a substituent of the formula -T-C(O)—(CRR')$_q$-U-, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_n$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted ($C_1$-$C_6$)alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of a active agent to provide the desired local or systemic effect. A "Topically effective," "Cosmetically effective," "pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

"Cosmetically effective" refers to a material that, when applied to the skin, nail, hair, claw or hoof, produces a desired cosmetic result locally at the place of application of an active ingredient in the material.

The terms "pharmaceutically acceptable salts" or "a salt thereof" are meant to include salts of the compounds of the invention which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the present invention provides compounds which are in a prodrug form. Prodrugs of the compounds or complexes described herein readily undergo chemical changes under physiological conditions to provide the compounds of the present invention. Additionally, prodrugs can be converted to the compounds of the present invention by chemical or biochemical methods in an ex vivo environment.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention. The graphic representations of racemic, ambiscalemic and scalemic or enantiomerically pure compounds used herein are taken from Maehr, *J. Chem. Ed.* 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy,* 21st Ed., Lippincott, Williams & Wilkins (2005) which is incorporated herein by reference.

The term "pharmaceutically acceptable carrier" or "pharmaceutically acceptable vehicle" refers to any formulation or carrier medium that provides the appropriate delivery of an effective amount of a active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy,* 21st Ed., Lippincott, Williams & Wilkins (2005) which is incorporated herein by reference.

"Pharmaceutically acceptable topical carrier" and equivalent terms refer to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal skin, nail, hair, claw or hoof using a diffusion cell apparatus. A diffusion cell is described by Merritt et al. Diffusion Apparatus for Skin Penetration, *J of Controlled Release,* 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical composition administered to a subject via the oral cavity, in which one or more antiplatelet agents and one or more acid inhibitors are administered concurrently in combination, optionally with one or more additional drugs. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package.

In a preferred embodiment, the oral dosage form is one, two or three units. In a particularly preferred embodiment, the oral dosage form is one unit.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment or lotion. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

The term, "prodrug", as defined herein, is a biologically inactive derivative of a parent drug molecule that exerts its pharmacological effect only after chemical and/or enzymatic conversion to its active form in vivo. Prodrugs include those designed to circumvent problems associated with delivery of the parent drug. This may be due to poor physicochemical properties, such as poor chemical stability or low aqueous solubility, and may also be due to poor pharmacokinetic properties, such as poor bioavailability or poor half-life. Thus, certain advantages of prodrugs may include improved chemical stability, absorption, and/or PK properties of the parent carboxylic acids. Prodrugs may also be used to make drugs more "patient friendly," by minimizing the frequency (e.g., once daily) or route of dosing (e.g., oral), or to improve the taste or odor if given orally, or to minimize pain if given parenterally.

In some embodiments, the prodrugs effect a "slow-release" of the active drug, thereby changing the time-course of D-serine increase in a manner that improves the efficacy of the parent compound. For example, compounds of the invention that extend D-serine level increases demonstrate improved efficacy in animal models of cognition (e.g., Contextual Fear Conditioning or Novel Object Recognition).

In some embodiments, the prodrugs are chemically more stable than the active drug, thereby improving formulation and delivery of the parent drug, compared to the drug alone.

Prodrugs for carboxylic acid analogs of the invention may include a variety of esters. In an exemplary embodiment, the pharmaceutical compositions of the invention include a carboxylic acid ester. In an exemplary embodiment, the prodrug is suitable for treatment/prevention of those diseases and conditions that require the drug molecule to cross the blood brain barrier. In an exemplary embodiment, the prodrug enters the brain, where it is converted into the active form of the drug molecule. In one embodiment, a prodrug is used to enable an active drug molecule to reach the inside of the eye after topical application of the prodrug to the eye. Additionally, a prodrug can be converted to its parent compound by chemical or biochemical methods in an ex vivo environment. For example, a prodrug can be slowly converted to its parent compound when placed in a transdermal patch reservoir with a suitable enzyme or chemical reagent.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to an broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

The term "substrates" means pharmaceutically acceptable particulate materials such as beads, particles, granules, pellets, and the like, in an oral dosage form.

The term, "substantially free", as used herein, refers to a composition which contains none of the substance or less than a therapeutically effective amount of the substance for any known purpose for which the composition is intended.

The term "microbial infection" refers to any infection of a host tissue by an infectious agent including, but not limited to, viruses, bacteria, mycobacteria, fungus and parasites (see, e.g., Harrison's Principles of Internal Medicine, pp. 93-98 (Wilson et al., eds., 12th ed. 1991); Williams et al., *J. of Medicinal Chem.* 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl, trichloroacetyl or trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

Boron is able to form dative bonds (or coordination bonds) with oxygen, sulfur or nitrogen under some circumstances in this invention. Dative bonds are usually weaker than covalent bonds. In situations where a boron atom is covalently bonded to at least one oxygen, sulfur or nitrogen, and is at the same time datively bonded to an oxygen, sulfur or nitrogen, respectively, the dative bond and covalent bond between the boron and the two identical heteroatoms can interconvert or be in the form of a resonance hybrid. There is potential uncertainty surrounding the exact nature and extent of electron sharing in these situations. The structures supplied are not intended to include any and all possible bonding scenarios between boron and the atom to which it is bound. Non limiting examples of these bonds are as follows:

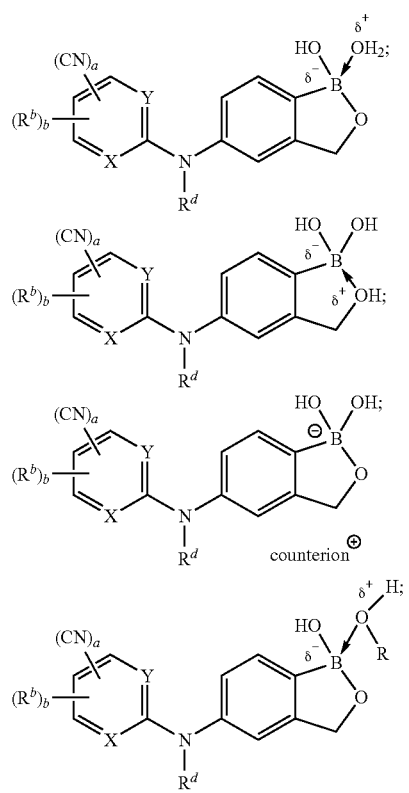

-continued

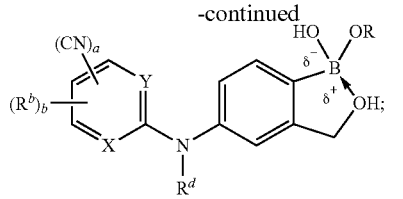

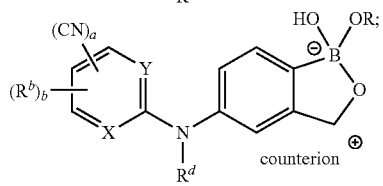

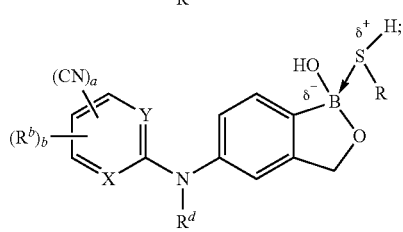

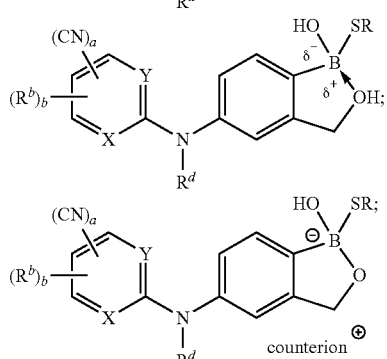

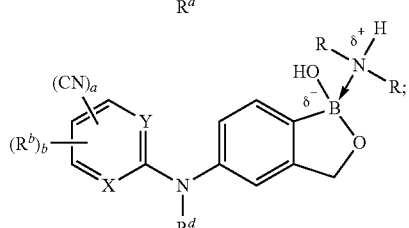

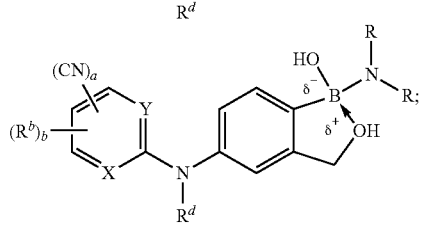

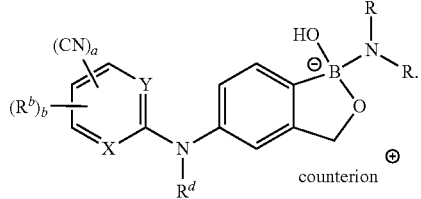

The compounds comprising a boron bonded to a carbon and three heteroatoms (such as three oxygens described in this section) can optionally contain a fully negatively charged boron or partially negatively charged boron, due to the nature of the dative bond between the boron and one of the oxygens.

Due to the negative charge, a positively charged counterion may associate with this compound, thus forming a salt. Examples of positively charged counterions include H', H₃O⁺, calcium, sodium, ammonium, potassium. The salts of these compounds are implicitly contained in descriptions of these compounds.

The present invention also encompasses compounds that are poly- or multi-valent species, including, for example, species such as dimers, trimers, tetramers and higher homologs of the compounds of use in the invention or reactive analogues thereof. For example, dimers can form under the following conditions:

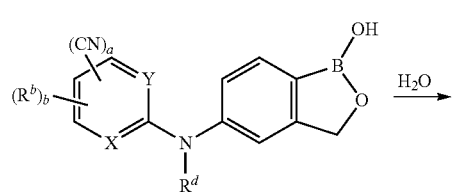

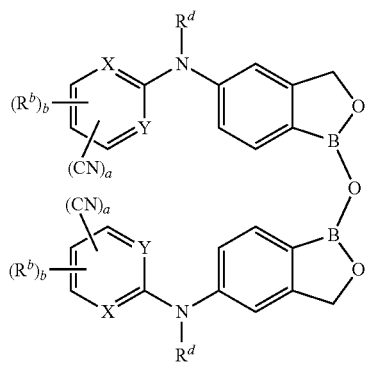

Trimers of the compounds of the invention are also produced. For example, trimers of acyclic boronic esters can be formed as follows:

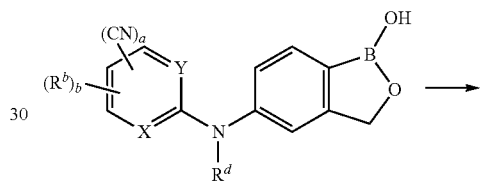

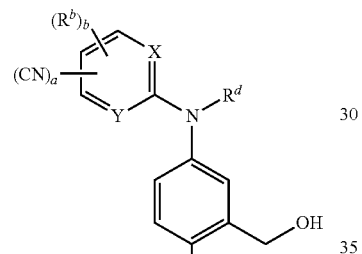

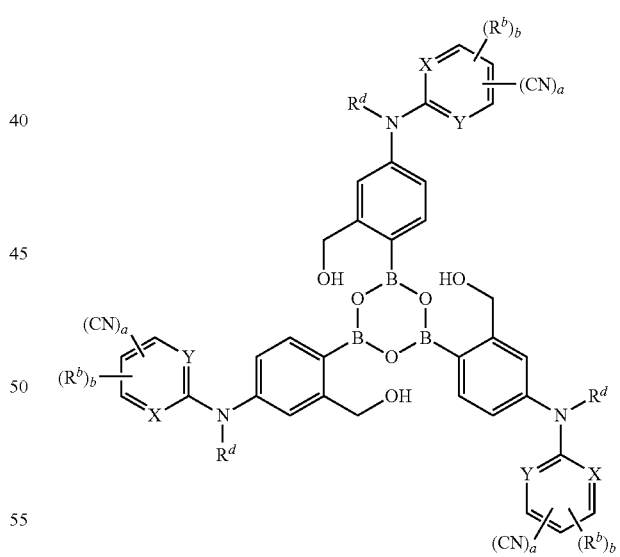

The present invention also encompasses compounds that are anhydrides of the cyclic boronic esters are synthesized by subjecting these compounds to dehydrating conditions. Examples of these anhydrides are provided below:

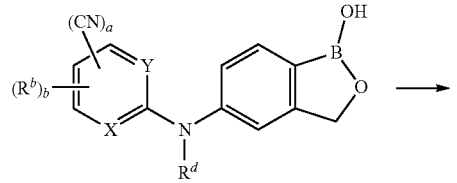

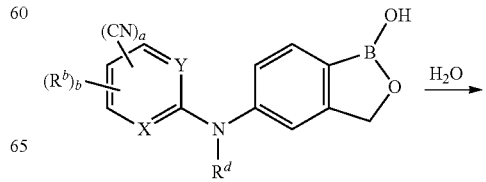

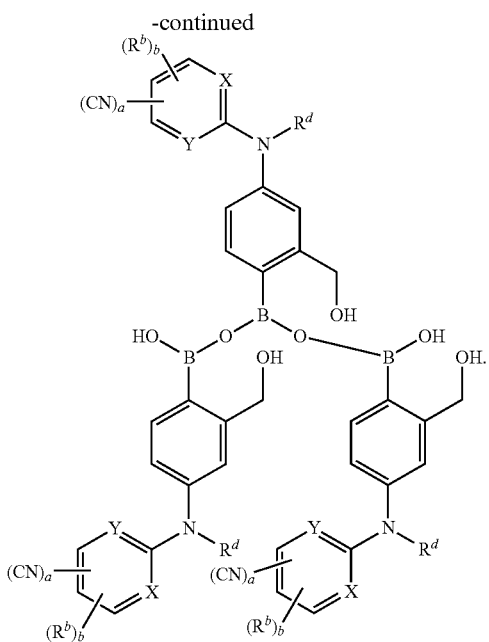

Polymers of the compounds of the invention are also produced through the removal of certain protecting groups in strong acid. For example, trimers can be formed as follows:

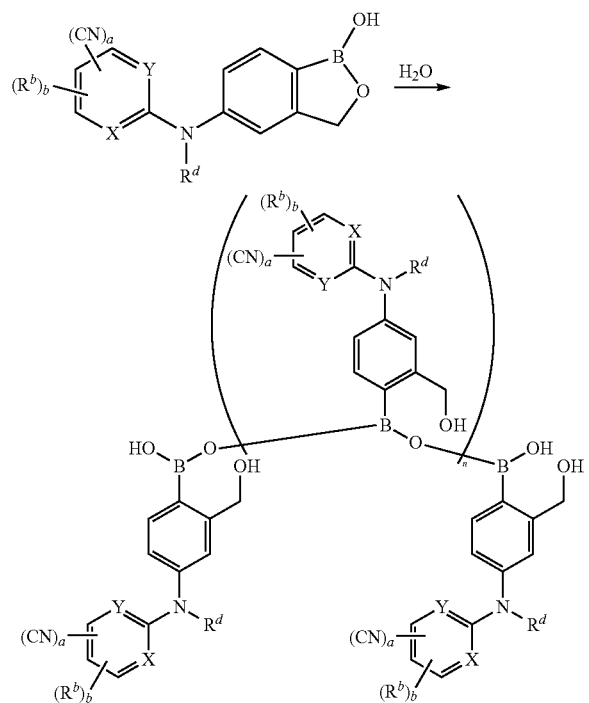

Also of use in the present invention are compounds that are poly- or multi-valent species, including, for example, species such as dimers, trimers, tetramers and higher homologs of the compounds of use in the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, is attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of use in the invention). Moreover, the framework can be derivatized with a single species of the invention or more than one species of the invention.

Moreover, the present invention includes the use of compounds within the motif set forth in the formulae contained herein, which are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to replace a hydroxyl group with a diol, or an amine with a quaternary amine, hydroxy amine or similar more water-soluble moiety. In a preferred embodiment, additional water solubility is imparted by substitution at a site not essential for the activity towards the editing domain of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

II. Introduction

The present invention has multiple aspects. These aspects include inventions directed to compounds, pharmaceutical formulations, methods of treating a condition, enhancing an effect, increasing the production of a cytokine and/or chemokine, decreasing the production of a cytokine and/or chemokine, increasing the release of a cytokine and/or chemokine, decreasing the release of a cytokine and/or chemokine, or inhibiting a phosphodiesterase.

III. Compounds

IIIa.

In a first aspect, the invention is a compound of the invention. In an exemplary embodiment, the invention is a compound described herein. In an exemplary embodiment, the compound is according to a formula described herein.

In a second aspect, the invention provides a compound having a structure according to the formula:

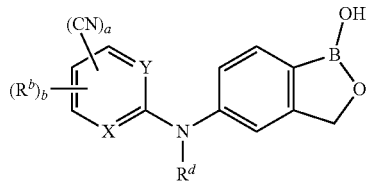

wherein X is selected from the group consisting of CH, C(CN), $CR^b$ and N. Y is selected from the group consisting of CH, C(CN), $CR^b$ and N. a is 0 or 1. b is 0 or 1. $R^d$ is selected from the group consisting of H, unsubstituted $C_1$-$C_6$ alkyl, $COR^{10}$, and —$C(O)OR^{10}$, wherein $R^{10}$ is selected from the group consisting of H and unsubstituted $C_1$-$C_6$ alkyl. There is a proviso that when X or Y is C(CN), then a is 0. There is a proviso that when X or Y is $CR^b$, then b is 0. There is a proviso that X and Y cannot both be C(CN). There is a proviso that X and Y cannot both be $CR^b$. $R^b$ is selected from the group consisting of $OR^4$, $NR^4R^5$, $SR^4$, —$S(O)R^4$, —$S(O)_2R^4$, —$S(O)_2NR^4R^5$, —$C(O)R^4$, —$C(O)OR^4$, —$C(O)NR^4R^5$, nitro, cyano, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein $R^4$ and $R^5$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. There is a proviso that $R^4$ and $R^5$, together with the atoms to which they are attached, are optionally combined to form a 5- to 7-membered substituted or unsubstituted heterocycloalkyl ring.

In an exemplary embodiment, X is N; and Y, a, b, $R^b$ and $R^d$ are as described herein. In an exemplary embodiment, X is CH; and Y, a, b, $R^b$ and $R^d$ are as described herein. In an exemplary embodiment, X is C(CN); a is 0; and Y, b, $R^b$ and $R^d$ are as described herein. In an exemplary embodiment, X is $CR^b$; Y, b, $R^b$ and $R^d$ are as described herein.

In an exemplary embodiment, X is N; Y is CH; a, b, $R^b$ and $R^d$ are as described herein. In an exemplary embodiment, X is CH; Y is CH; a, b, $R^b$ and $R^d$ are as described herein. In an exemplary embodiment, X is C(CN); Y is CH; a is 0; and b, $R^b$ and $R^d$ are as described herein. In an exemplary embodiment, X is $CR^b$; Y is CH; b, $R^b$ and $R^d$ are as described herein.

In an exemplary embodiment, Y is N; and X, a, b, $R^b$ and $R^d$ are as described herein. In an exemplary embodiment, Y is CH; and X, a, b, $R^b$ and $R^d$ are as described herein. In an exemplary embodiment, Y is C(CN); a is 0; and X, a, b, $R^b$ and $R^d$ are as described herein. In an exemplary embodiment, Y is $CR^b$; and X, a, b, $R^b$ and $R^d$ are as described herein.

In an exemplary embodiment, $R^d$ is H; and X, Y, a, b and $R^b$ are as described herein. In an exemplary embodiment, $R^d$ is methyl; and X, Y, a, b and $R^b$ are as described herein. In an exemplary embodiment, $R^d$ is ethyl; and X, Y, a, b and $R^b$ are as described herein. In an exemplary embodiment, $R^d$ is unsubstituted $C_3$ alkyl; and X, Y, a, b and $R^b$ are as described herein. In an exemplary embodiment, $R^d$ is propyl; and X, Y, a, b and $R^b$ are as described herein. In an exemplary embodiment, $R^d$ is unsubstituted $C_4$ alkyl; and X, Y, a, b and $R^b$ are as described herein. In an exemplary embodiment, $R^d$ is butyl; and X, Y, a, b and $R^b$ are as described herein. In an exemplary embodiment, $R^d$ is unsubstituted $C_5$ alkyl; and X, Y, a, b and $R^b$ are as described herein. In an exemplary embodiment, $R^d$ is pentyl; and X, Y, a, b and $R^b$ are as described herein. In an exemplary embodiment, $R^d$ is unsubstituted $C_6$ alkyl; and X, Y, a, b and $R^b$ are as described herein. In an exemplary embodiment, $R^d$ is hexyl; and X, Y, a, b and $R^b$ are as described herein.

In an exemplary embodiment, X, Y, a, b and $R^b$ are as described herein and $R^d$ is —$C(O)OR^{10}$, wherein $R^{10}$ is $C_1$-$C_6$ unsubstituted alkyl. In an exemplary embodiment, X, Y, a, b and $R^b$ are as described herein and $R^d$ is —$C(O)OCH_3$. In an exemplary embodiment, X, Y, a, b and $R^b$ are as described herein and $R^d$ is —$C(O)OCH_2CH_3$. In an exemplary embodiment, X, Y, a, b and $R^b$ are as described herein and $R^d$ is —$C(O)OR^{10}$, wherein $R^{10}$ is propyl. In an exemplary embodiment, X, Y, a, b and $R^b$ are as described herein and $R^d$ is —$C(O)OR^{10}$, wherein $R^{10}$ is isopropyl. In an exemplary embodiment, X, Y, a, b and $R^b$ are as described herein and $R^d$ is —$C(O)OR^{10}$, wherein $R^{10}$ is n-butyl. In an exemplary embodiment, X, Y, a, b and $R^b$ are as described herein and $R^d$ is —$C(O)OR^{10}$, wherein $R^{10}$ is isobutyl. In an exemplary embodiment, X, Y, a, b and $R^b$ are as described herein and $R^d$ is —$C(O)OR^{10}$, wherein $R^{10}$ is t-butyl. In an exemplary embodiment, X, Y, a, b and $R^b$ are as described herein and $R^d$ is —$C(O)OR^{10}$, wherein $R^{10}$ is sec-butyl. In an exemplary embodiment, X, Y, a, b and $R^b$ are as described herein and $R^d$ is —$C(O)OR^{10}$, wherein $R^{10}$ is pentyl. In an exemplary embodiment, X, Y, a, b and $R^b$ are as described herein and $R^d$ is —$C(O)OR^{10}$, wherein $R^{10}$ is isopentyl. In an exemplary embodiment, X, Y, a, b and $R^b$ are as described herein and $R^d$ is —$C(O)OR^{10}$, wherein $R^{10}$ is hexyl. In an exemplary embodiment, X, Y, a, b and $R^b$ are as described herein and $R^d$ is —$C(O)OH$.

In an exemplary embodiment, X, Y, a, b and $R^b$ are as described herein and $R^d$ is —$C(O)R^{10}$, wherein $R^{10}$ is $C_1$-$C_6$ unsubstituted alkyl. In an exemplary embodiment, X, Y, a, b and $R^b$ are as described herein and $R^d$ is —$C(O)CH_3$. In an exemplary embodiment, X, Y, a, b and $R^b$ are as described herein and $R^d$ is —$C(O)CH_2CH_3$. In an exemplary embodiment, X, Y, a, b and $R^b$ are as described herein and $R^d$ is —$C(O)R^{10}$, wherein $R^{10}$ is propyl. In an exemplary embodiment, X, Y, a, b and $R^b$ are as described herein and $R^d$ is —$C(O)R^{10}$, wherein $R^{10}$ is isopropyl. In an exemplary embodiment, X, Y, a, b and $R^b$ are as described herein and $R^d$ is —$C(O)R^{10}$, wherein $R^{10}$ is n-butyl. In an exemplary embodiment, X, Y, a, b and $R^b$ are as described herein and $R^d$ is —$C(O)R^{10}$, wherein $R^{10}$ is isobutyl. In an exemplary embodiment, X, Y, a, b and $R^b$ are as described herein and $R^d$ is —$C(O)R^{10}$, wherein $R^{10}$ is t-butyl. In an exemplary embodiment, X, Y, a, b and $R^b$ are as described herein and $R^d$ is —$C(O)R^{10}$, wherein $R^{10}$ is sec-butyl. In an exemplary embodiment, X, Y, a, b and $R^b$ are as described herein and $R^d$ is —$C(O)R^{10}$, wherein $R^{10}$ is pentyl. In an exemplary embodiment, X, Y, a, b and $R^b$ are as described herein and $R^d$ is —$C(O)R^{10}$, wherein $R^{10}$ is isopentyl. In an exemplary embodiment, X, Y, a, b and $R^b$ are as described herein and $R^d$ is —$C(O)R^{10}$, wherein $R^{10}$ is hexyl. In an exemplary embodiment, X, Y, a, b and $R^b$ are as described herein and $R^d$ is —$C(O)H$.

In an exemplary embodiment, X, Y, a and $R^d$ are as described herein; b is 1; and $R^b$ is as described herein. In an exemplary embodiment, X, Y, a and $R^d$ are as described herein; b is 1; and $R^b$ is selected from the group consisting of $OR^4$, $NR^4R^5$, $SR^4$, —$S(O)R^4$, —$S(O)_2R^4$, —$S(O)_2NR^4R^5$, —$C(O)R^4$, —$C(O)OR^4$, —$C(O)NR^4R^5$, nitro, cyano, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein each $R^4$ and $R^5$ are as described herein.

In an exemplary embodiment, X, Y, a and $R^d$ are as described herein; b is 1; $R^b$ is selected from the group consisting of —$CH_2C(O)OR^6$, —$CH_2NHC(O)R^6$ and —$CH_2NR^6R^7$, wherein $R^6$ and $R^7$ are each independently selected from the group consisting of H, methyl, trifluoromethyl, ethyl, propyl, butyl, t-butyl, —$C(O)H$, wherein $R^6$ and $R^7$, together with the together with nitrogen to which they are attached, are optionally combined to form a member selected from the group consisting of 4-methylpiperazinyl, piperidinyl, morpholino and pyrrolidinyl. In an exemplary embodiment, X, Y, a and $R^d$ are as described herein; b is 1; $R^b$ is selected from the group consisting of methyl, trifluoromethyl, —CH$_2$OH, —CH$_2$N(CH$_3$)$_2$,

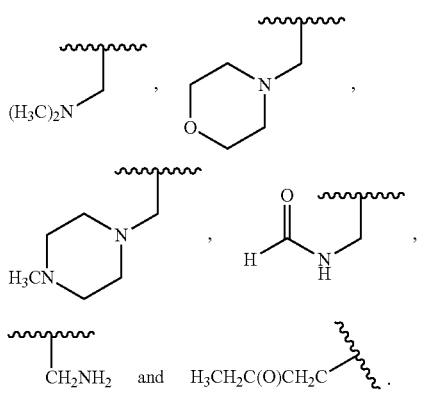

In an exemplary embodiment, X, Y, a and $R^d$ are as described herein; b is 1; $R^b$ is selected from the group consisting of —OR$^4$, —C(O)R$^4$, —C(O)OR$^4$ and —C(O)NR$^4$R$^5$, wherein R$^4$ and R$^5$ are each independently selected from the group consisting of H, methyl, ethyl, methoxyethyl, cyclopropyl, —CH$_2$C(O)OR$^8$, —CH$_2$C(O)NR$^8$R$^9$, 2-(dimethylamino)ethyl, 2-pyridinylmethyl, 2-(4-cyano)pyridinyl, with the proviso that R$^8$ and R$^9$, together with the atoms to which they are attached, are optionally combined to form a 5- to 7-membered substituted or unsubstituted heterocycloalkyl ring.

In an exemplary embodiment, X, Y, a and $R^d$ are as described herein; b is 1; $R^b$ is selected from the group consisting of —OH, —OCH$_3$, —OCH$_2$CH$_3$, —OCH$_2$CH$_2$OCH$_3$, —OCH$_2$C(O)OH, —OCH$_2$C(O)OCH$_2$CH$_3$, —OCH$_2$C(O)OC(CH$_3$)$_3$, —C(O)OCH$_3$, —C(O)OH, —C(O)H, —OCH$_2$C(O)N(CH$_2$CH$_3$)$_2$,

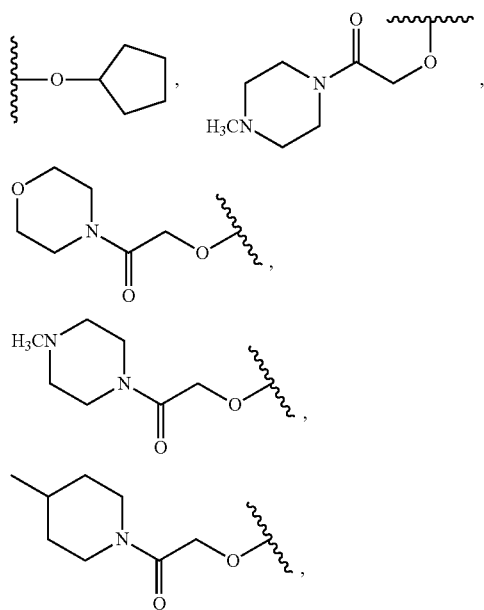

In an exemplary embodiment, X, Y, a and $R^d$ are as described herein; b is 1; $R^b$ is selected from the group consisting of F, Cl, methyl, trifluoromethyl, —CH$_2$OH, —CH$_2$N(CH$_3$)$_2$, —OH, —OCH$_3$, —OCH$_2$CH$_3$, —OCH$_2$CH$_2$OCH$_3$, —OCH$_2$C(O)OH, —OCH$_2$C(O)OCH$_2$CH$_3$, —OCH$_2$C(O)OC(CH$_3$)$_3$, —C(O)OCH$_3$, —C(O)OH, —C(O)H, —OCH$_2$C(O)N(CH$_2$CH$_3$)$_2$,

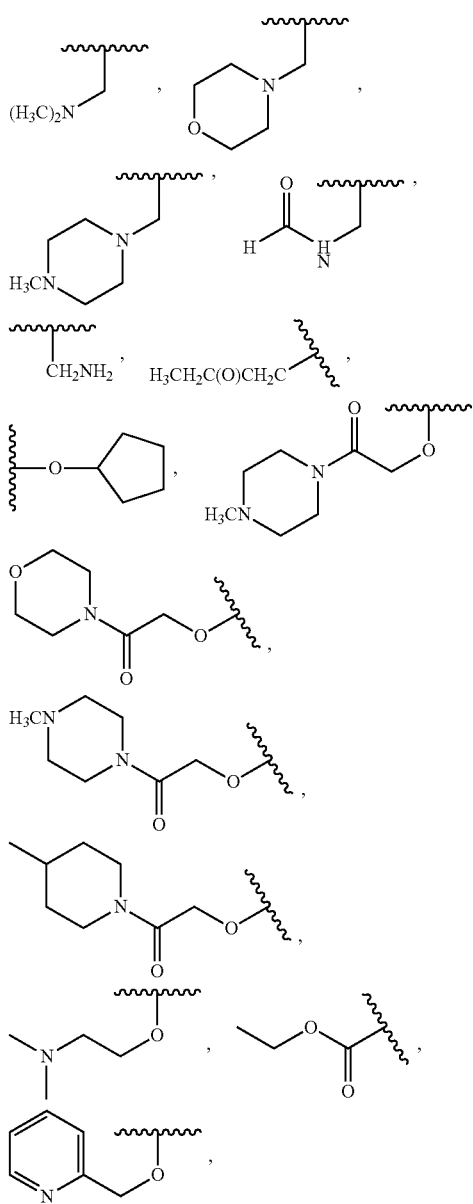

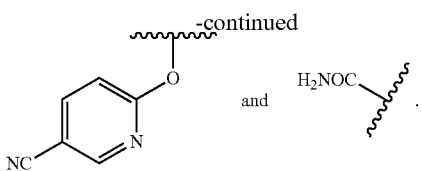

In an exemplary embodiment, the compound has a structure according to the formula:

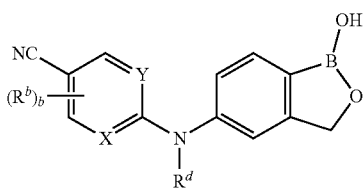

wherein X is N or CH or $CR^b$. Y is selected from the group consisting of N, CH and $CR^b$. $R^d$ is selected from the group consisting of H, unsubstituted $C_1$-$C_6$ alkyl, $COR^{10}$, and —$C(O)OR^{10}$, wherein $R^{10}$ is selected from the group consisting of H and unsubstituted $C_1$-$C_6$ alkyl. There is a proviso that b is 1 unless X or Y is $CR^b$, when b is 0. There is a proviso that X and Y cannot both be $CR^b$. $R^b$ is selected from the group consisting of $OR^4$, $NR^4R^5$, $SR^4$, —$S(O)R^4$, —$S(O)_2R^4$, —$S(O)_2NR^4R^5$, —$C(O)R^4$, —$C(O)OR^4$, —$C(O)NR^4R^5$, nitro, cyano, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein $R^4$ and $R^5$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. There is a proviso that $R^4$ and $R^5$, together with the atoms to which they are attached, are optionally combined to form a 5- to 7-membered substituted or unsubstituted heterocycloalkyl ring.

In an exemplary embodiment, X, Y and $R^d$ are as described herein; b is 1; $R^b$ is alkyl, optionally substituted with a member selected from the group consisting of halogen, $OR^{4a}$, $C(O)OR^{4a}$, $NR^{4a}R^{4b}$, substituted or unsubstituted heterocycloalkyl or unsubstituted heteroaryl, wherein $R^{4a}$ and $R^{4b}$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{4a}$ is H or unsubstituted alkyl. In an exemplary embodiment, $R^{4b}$ is H or unsubstituted alkyl or C(O)H. In an exemplary embodiment, $R^b$ is fluoro. In an exemplary embodiment, $R^b$ is chloro.

In an exemplary embodiment, X, Y and $R^d$ are as described herein; b is 1; $R^b$ is OH. In an exemplary embodiment, X, Y and $R^d$ are as described herein; b is 1; $R^b$ is $OR^4$, wherein $R^4$ is alkyl is optionally substituted with at least one halogen, hydroxyl, ether, carboxy or ester moiety. In an exemplary embodiment, X, Y and $R^d$ are as described herein; b is 1; $R^b$ is $OR^4$, wherein $R^4$ is alkyl is optionally substituted with one halogen or one hydroxyl or one ether or one carboxy or one ester moiety.

In an exemplary embodiment, X, Y and $R^d$ are as described herein; b is 1; $R^b$ is $OR^4$, wherein $R^4$ is unsubstituted alkyl. In an exemplary embodiment, X, Y and $R^d$ are as described herein; b is 1; $R^b$ is $OR^4$, wherein $R^4$ is unsubstituted $C_1$ or $C_2$ or $C_3$ alkyl. In an exemplary embodiment, X, Y and $R^d$ are as described herein; b is 1; $R^b$ is $OR^4$, wherein $R^4$ is unsubstituted $C_4$ or $C_5$ or $C_6$ alkyl. In an exemplary embodiment, X, Y and $R^d$ are as described herein; b is 1; $R^b$ is $OR^4$, wherein $R^4$ is methyl or ethyl or propyl or isopropyl or isobutyl.

In an exemplary embodiment, X, Y and $R^d$ are as described herein; b is 1; $R^b$ is $OR^4$, wherein $R^4$ is alkyl substituted with at least one halogen. In an exemplary embodiment, X, Y and $R^d$ are as described herein; b is 1; $R^b$ is $OR^4$, wherein $R^4$ is alkyl substituted with one or two or three halogen(s). In an exemplary embodiment, X, Y and $R^d$ are as described herein; b is 1; $R^b$ is $O(CH_2)_{m1}R^{31}$, wherein m1 is 0 or 1 or 2 or 3 or 4 or 5 or 6 and $R^{31}$ is a methyl moiety wherein at least one of the methyl hydrogens is substituted with a halogen. In an exemplary embodiment, the halogen is chloro. In an exemplary embodiment, the halogen is fluoro. In an exemplary embodiment, $R^{31}$ is —$CF_3$. In an exemplary embodiment, $R^{31}$ is —$CHF_2$. In an exemplary embodiment, m1 is 1 or 2 or 3. In an exemplary embodiment, X, Y and $R^d$ are as described herein; b is 1; $R^b$ is —$OCH_2CF_3$. In an exemplary embodiment, X, Y and $R^d$ are as described herein; b is 1; $R^b$ is —$OCH_2CHF_2$.

In an exemplary embodiment, X, Y and $R^d$ are as described herein; b is 1; $R^b$ is —$O(CH_2)_{m1}OC(O)R^{4d}$, wherein m1 is a number selected from 1 or 2 or 3 or 4 or 5 or 6 and $R^{4d}$ is unsubstituted alkyl. In an exemplary embodiment, m1 is 1 or 2 or 3. In an exemplary embodiment, m1 is 2. In an exemplary embodiment, $R^{4d}$ is unsubstituted $C_1$ or $C_2$ or $C_3$ alkyl. In an exemplary embodiment, $R^{4d}$ is unsubstituted $C_4$ or $C_5$ or $C_6$ alkyl. In an exemplary embodiment, $R^{4d}$ is methyl. In an exemplary embodiment, X, Y and $R^d$ are as described herein; b is 1; $R^b$ is —$O(CH_2)_2OC(O)CH_3$.

In an exemplary embodiment, X, Y and $R^d$ are as described herein; b is 1; $R^b$ is —$O(CH_2)_{m1}C(O)R^{4d}$, wherein m1 is a number selected from 1 or 2 or 3 or 4 or 5 or 6 and $R^{4d}$ is unsubstituted alkyl. In an exemplary embodiment, m1 is 2 or 3 or 4. In an exemplary embodiment, m1 is 3. In an exemplary embodiment, $R^{4d}$ is unsubstituted $C_1$ or $C_2$ or $C_3$ alkyl. In an exemplary embodiment, $R^{4d}$ is unsubstituted $C_4$ or $C_5$ or $C_6$ alkyl. In an exemplary embodiment, $R^{4d}$ is methyl. In an exemplary embodiment, X, Y and $R^d$ are as described herein; b is 1; $R^b$ is —$O(CH_2)_3C(O)CH_3$.

In an exemplary embodiment, X, Y and $R^d$ are as described herein; b is 1; $R^b$ is —$O(CH_2)_{m1}C(O)OR^{4d}$, wherein m1 is a number selected from 1 or 2 or 3 or 4 or 5 or 6 and $R^{4d}$ is H or unsubstituted alkyl. In an exemplary embodiment, X, Y and $R^d$ are as described herein; b is 1; $R^b$ is —$OCH_2C(O)OR^{4d}$, wherein $R^{4d}$ is as described herein. In an exemplary embodiment, $R^{4d}$ is H or methyl or ethyl or t-butyl. In an exemplary embodiment, X, Y and $R^d$ are as described herein; b is 1; $R^b$ is —$O(CH_2)C(O)OCH_2CH_3$ or —$O(CH_2)C(O)OH$ or —$O(CH_2)C(O)OC(CH_3)_3$.

In an exemplary embodiment, X, Y and $R^d$ are as described herein; b is 1; $R^b$ is $OR^4$, wherein $R^4$ is alkyl substituted with a substituted or unsubstituted amino. In an exemplary embodiment, X, Y and $R^d$ are as described herein; b is 1; $R^b$ is —$O(CH_2)_{m2}C(O)NR^{4e}R^{4f}$, wherein m2 is a number selected from 1 or 2 or 3 or 4 or 5 or 6, and $R^{4e}$ is H or unsubstituted alkyl, $R^{4f}$ is H or unsubstituted alkyl, or $R^{4e}$ and $R^{4f}$, together with the nitrogen to which they are attached, are optionally joined to form a substituted or unsubstituted 4 to 8 membered ring.

In an exemplary embodiment, X, Y and $R^d$ are as described herein; b is 1; $R^b$ is —$OCH_2C(O)NR^{4e}R^{4f}$, wherein $R^{4e}$ and $R^{4f}$ are as described herein. In an exemplary embodiment, $R^{4e}$ and $R^{4f}$ are the same and each are independently selected unsubstituted alkyl. In an exemplary embodiment, $R^{4e}$ and $R^{4f}$ are different and each are independently selected unsubstituted alkyl. In an exemplary embodiment, $R^{4e}$ is H. In an exemplary embodiment, $R^{4f}$ is H. In an exemplary embodiment, $R^{4e}$ and $R^{4f}$ are ethyl. In an exemplary embodiment, $R^{4e}$ and $R^{4f}$, together with the nitrogen to which they are attached, are joined to form piperazinyl, either unsubstituted or substituted with unsubstituted alkyl on the nitrogen at the 4-position. In an exemplary embodiment, $R^{4e}$ and $R^{4f}$, together with the nitrogen to which they are attached, are joined to form N-methyl piperazinyl. In an exemplary embodiment, $R^{4e}$ and $R^{4f}$, together with the nitrogen to which they are attached, are joined to form piperidinyl, either unsubstituted or substituted with unsubstituted alkyl. In an exemplary embodiment, $R^{4e}$ and $R^{4f}$, together with the nitrogen to which they are attached, are joined to form 4-methyl piperidinyl. In an exemplary embodiment, $R^{4e}$ and $R^{4f}$, together with the nitrogen to which they are attached, are joined to form unsubstituted morpholinyl.

In an exemplary embodiment, X, Y and $R^d$ are as described herein; b is 1; $R^b$ is $OR^4$, wherein $R^4$ is unsubstituted alkyl. In an exemplary embodiment, $R^4$ is $C_1$ or $C_2$ or $C_3$ or $C_4$ or $C_5$ or $C_6$ alkyl. In an exemplary embodiment, $R^4$ is $C_1$ alkyl. In an exemplary embodiment, X, Y and $R^d$ are as described herein; b is 1; $R^b$ is $OR^4$, wherein $R^4$ is alkyl substituted with unsubstituted pyridinyl. In an exemplary embodiment, X, Y and $R^d$ are as described herein; b is 1; $R^b$ is

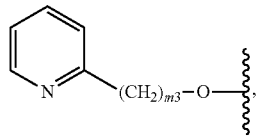

wherein m3 is 1 or 2 or 3 or 4 or 5 or 6. In an exemplary embodiment, m3 is 1.

In an exemplary embodiment, X, Y and $R^d$ are as described herein; b is 1; $R^b$ is $OR^4$, wherein $R^4$ is substituted or unsubstituted cycloalkyl. In an exemplary embodiment, X, Y and $R^d$ are as described herein; b is 1; $R^b$ is $OR^4$, wherein $R^4$ is unsubstituted cycloalkyl. In an exemplary embodiment, X, Y and $R^d$ are as described herein; b is 1; $R^b$ is $OR^4$, wherein $R^4$ is cyclopentyl. In an exemplary embodiment, $R^4$ is unsubstituted cyclohexyl.

In an exemplary embodiment, X, Y and $R^d$ are as described herein; b is 1; $R^b$ is $OR^4$, wherein $R^4$ is alkyl substituted with unsubstituted alkoxy. In an exemplary embodiment, X, Y and $R^d$ are as described herein; b is 1; $R^b$ is —$O(CH_2)_{m5}OR^{30}$, wherein m5 is 1 or 2 or 3 or 4 or 5 or 6 and $R^{30}$ is H or unsubstituted alkyl or unsubstituted tetrahydropyran. In an exemplary embodiment, $R^{30}$ is $C_1$ or $C_2$ or $C_3$ or $C_4$ or $C_5$ or $C_6$ alkyl. In an exemplary embodiment, m5 is 1 or 2 or 3. In an exemplary embodiment, m5 is 2. In an exemplary embodiment, $R^{30}$ is $C_1$ or $C_2$ or $C_3$ alkyl. In an exemplary embodiment, $R^{30}$ is $C_4$ or $C_5$ or $C_6$ alkyl. In an exemplary embodiment, $R^{30}$ is H. In an exemplary embodiment, $R^{30}$ is methyl or isopropyl. In an exemplary embodiment, $R^{30}$ is 2-tetrahydropyran. In an exemplary embodiment, X, Y and $R^d$ are as described herein; b is 1; $R^b$ is —$O(CH_2)_2OCH(CH_3)_2$ or —$O(CH_2)_2OH$ or —$O(CH_2)_2O$—THP (TetraHydroPyran).

In an exemplary embodiment, X, Y and $R^d$ are as described herein; b is 1; $R^b$ is $OR^4$, wherein $R^4$ is alkyl substituted with unsubstituted cycloalkyl. In an exemplary embodiment, X, Y and $R^d$ are as described herein; b is 1; $R^b$ is —$O(CH_2)_{m5}OR^{30}$, wherein m5 is 1 or 2 or 3 or 4 or 5 or 6 and $R^{30}$ is a 3-8 membered cycloalkyl. In an exemplary embodiment, $R^{30}$ is a 3-6 membered cycloalkyl. In an exemplary embodiment, $R^{30}$ is cyclopropyl or cyclopentyl. In an exemplary embodiment, m5 is 1 or 2 or 3. In an exemplary embodiment, m5 is 1.

In an exemplary embodiment, X, Y and $R^d$ are as described herein; b is 1; $R^b$ is $C(O)R^4$, wherein $R^4$ is unsubstituted alkyl. In an exemplary embodiment, $R^4$ is $C_1$ or $C_2$ or $C_3$ or $C_4$ or $C_5$ or $C_6$ alkyl. In an exemplary embodiment, $R^4$ is $C_1$ alkyl. In an exemplary embodiment, X, Y and $R^d$ are as described herein; b is 1; $R^b$ is $C(O)H$. In an exemplary embodiment, X, Y and $R^d$ are as described herein; b is 1; $R^b$ is $C_1$ or $C_2$ or $C_3$ or $C_4$ or $C_5$ or $C_6$ alkyl. In an exemplary embodiment, $R^b$ is $C_1$ alkyl. In an exemplary embodiment, X, Y and $R^d$ are as described herein; b is 1; $R^b$ is alkyl substituted with halogen. In an exemplary embodiment, X, Y and $R^d$ are as described herein; b is 1; $R^b$ is alkyl substituted with at least one halogen. In an exemplary embodiment, X, Y and $R^d$ are as described herein; b is 1; $R^b$ is alkyl substituted with at least one fluoro. In an exemplary embodiment, X, Y and $R^d$ are as described herein; b is 1; $R^b$ is $CF_3$.

In an exemplary embodiment, X, Y and $R^d$ are as described herein; b is 1; $R^b$ is alkyl substituted with hydroxy. In an exemplary embodiment, X, Y and $R^d$ are as described herein; b is 1; $R^b$ is —$(CH_2)_{m4}OH$, wherein m4 is a number selected from 1 or 2 or 3 or 4 or 5 or 6. In an exemplary embodiment, m4 is 1.

In an exemplary embodiment, X, Y and $R^d$ are as described herein; b is 1; $R^b$ is alkyl substituted with carboxy or ester. In an exemplary embodiment, X, Y and $R^d$ are as described herein; b is 1; $R^b$ is —$(CH_2)_{m1}C(O)OR^{4a}$, wherein m1 is a number selected from 1 or 2 or 3 or 4 or 5 or 6 and $R^{4a}$ is H or unsubstituted alkyl.

In an exemplary embodiment, X, Y and $R^d$ are as described herein; b is 1; $R^b$ is —$CH_2C(O)OR^{4a}$, wherein $R^{4a}$ is as described herein. In an exemplary embodiment, $R^{4a}$ is H or methyl or ethyl or t-butyl.

In an exemplary embodiment, X, Y and $R^d$ are as described herein; b is 1; $R^b$ is alkyl substituted with amino. In an exemplary embodiment, X, Y and $R^d$ are as described herein; b is 1; $R^b$ is —$(CH_2)_{m7}NR^{4a}R^{4b}$, wherein m7 is selected from the group consisting of 1, 2, 3, 4, 5 and 6 and $R^{4a}$ is selected from the group consisting of H, unsubstituted alkyl and formyl, $R^{4b}$ is selected from the group consisting of H, unsubstituted alkyl and formyl, or $R^{4a}$ and $R^{4b}$, together with the nitrogen to which they are attached, are optionally joined to form a substituted or unsubstituted 4 to 8 membered ring. In an exemplary embodiment, $R^{4b}$ is as described herein, $R^{4a}$ is H. In an exemplary embodiment, $R^{4a}$ is as described herein, $R^{4b}$ is H. In an exemplary embodiment, $R^{4b}$ is as described herein, $R^{4a}$ is methyl. In an exemplary embodiment, $R^{4a}$ is as described herein, $R^{4b}$ is methyl. In an exemplary embodiment, m7 is 1. In an exemplary embodiment, $R^{4a}$ and $R^{4b}$, together with the nitrogen to which they are attached, are joined to form piperazinyl, either unsubstituted or substituted with unsubstituted alkyl on the nitrogen at the 4-position. In an exemplary embodiment, $R^{4a}$ and $R^{4b}$, together with the nitrogen to which they are attached, are joined to form N-methyl piperazinyl. In an exemplary embodiment, $R^{4a}$ and $R^{4b}$, together with the nitrogen to which they are attached, are joined to form piperidinyl, either unsubstituted or substituted with unsubstituted alkyl. In an exemplary embodiment, $R^{4a}$ and $R^{4b}$, together with the nitrogen to which they are attached, are joined to form 4-methyl piperidinyl. In an exemplary embodiment, $R^{4a}$ and $R^{4b}$, together with the nitrogen to which they are attached, are joined to form unsubstituted morpholinyl.

In an exemplary embodiment, X, Y and $R^d$ are as described herein; b is 1; $R^b$ is $NH_2$. In an exemplary embodiment, X, Y and $R^d$ are as described herein; b is 1; $R^b$ is $NR^4R^5$ wherein $R^4$ is H or unsubstituted alkyl, and $R^5$ is selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, X, Y and $R^d$ are as described herein; b is 1; $R^b$ is $NR^4R^5$, $R^4$ is as described herein, $R^5$ is unsubstituted alkyl. In an exemplary embodiment, X, Y and $R^d$ are as described herein; b is 1; $R^b$ is $NR^4R^5$, wherein $R^4$ is H, $R^5$ is as described herein. In an exemplary embodiment, X, Y and $R^d$ are as described herein; b is 1; $R^b$ is $NR^4R^5$, wherein $R^4$ is unsubstituted alkyl, $R^5$ is as described herein. In an exemplary embodiment, X, Y and $R^d$ are as described herein; b is 1; $R^b$ is $NR^4R^5$, wherein $R^5$ is as described herein, $R^4$ is unsubstituted $C_1$ or $C_2$ or $C_3$ or $C_4$ or $C_5$ or $C_6$ alkyl. In an exemplary embodiment, X, Y and $R^d$ are as described herein; b is 1; $R^b$ is $NR^4R^5$, wherein $R^4$ is unsubstituted $C_1$ or $C_2$ or $C_3$ alkyl and $R^5$ is as described herein. In an exemplary embodiment, X, Y and $R^d$ are as described herein; b is 1; $R^b$ is $NR^4R^5$, wherein $R^4$ is methyl and $R^5$ is as described herein. In an exemplary embodiment, X, Y and $R^d$ are as described herein; b is 1; $R^b$ is $NR^4R^5$, wherein $R^4$ is as described herein and $R^5$ is unsubstituted $C_1$ or $C_2$ or $C_3$ or $C_4$ or $C_5$ or $C_6$ alkyl. In an exemplary embodiment, X, Y and $R^d$ are as described herein; b is 1; $R^b$ is $NR^4R^5$, wherein $R^5$ is methyl or tert-butyl, and $R^4$ is as described herein.

In an exemplary embodiment, X, Y and $R^d$ are as described herein; b is 1; $R^b$ is $NR^4R^5$, wherein $R^4$ is as described herein, $R^5$ is alkyl, substituted with a member selected from OH, unsubstituted arylalkoxy, unsubstituted alkoxy, and unsubstituted aryl. In an exemplary embodiment, X, Y and $R^d$ are as described herein; b is 1; $R^b$ is $NR^4R^5$, wherein $R^5$ is $—(CH_2)_{m8}Ph$.

In an exemplary embodiment, X, Y and $R^d$ are as described herein; b is 1; $R^b$ is $NR^4R^5$, wherein $R^5$ is $—(CH_2)_{m8}OR^{26}$, wherein m8 is selected from the group consisting of 1, 2, 3, 4, 5 and 6 and $R^{26}$ is selected from the group consisting of H and unsubstituted or arylsubstituted $C_1$ or $C_2$ or $C_3$ or $C_4$ or $C_5$ or $C_6$ alkyl. In an exemplary embodiment, m8 is 1 or 2 or 3. In an exemplary embodiment, m8 is 2. In an exemplary embodiment, $R^{26}$ is unsubstituted $C_1$ or $C_2$ or $C_3$ or $C_4$ or $C_5$ or $C_6$ alkyl. In an exemplary embodiment, $R^{26}$ is methyl. In an exemplary embodiment, $R^{26}$ is benzyl. In an exemplary embodiment, X, Y and $R^d$ are as described herein; b is 1; $R^b$ is $NR^4R^5$, wherein $R^4$ is as desibed herein, $R^5$ is $—(CH_2)_{m8}O(CH_2)_{m9}Ph$, wherein m8 is 1 or 2 or 3 or 4 or 5 or 6 and m9 is 1 or 2 or 3 or 4 or 5 or 6. In an exemplary embodiment, X, Y and $R^d$ are as described herein; b is 1; $R^b$ is $NR^4R^5$, wherein $R^4$ is as described herein $R^5$ is $—(CH_2)_{m8}O(CH_2)_{m9}Ph$, wherein m8 is 1 or 2 or 3 and m9 is 1 or 2 or 3. In an exemplary embodiment, X, Y and $R^d$ are as described herein; b is 1; $R^b$ is $NR^4R^5$, wherein $R^4$ is as described herein, $R^5$ is $—(CH_2)_{m8}O(CH_2)Ph$. In an exemplary embodiment, X, Y and $R^d$ are as described herein; b is 1; $R^b$ is $NR^4R^5$, wherein $R^4$ is as described herein $R^5$ is $—(CH_2)_2O(CH_2)_{m9}Ph$. In an exemplary embodiment, X, Y and $R^d$ are as described herein; b is 1; $R^b$ is $NR^4R^5$, wherein $R^4$ is as described herein $R^5$ is $—(CH_2)_2O(CH_2)Ph$.

In an exemplary embodiment, X, Y and $R^d$ are as described herein; b is 1; $R^b$ is selected from the group consisting of $—NH(CH_2)_2OH$, $—NH(CH_2)_2OCH_3$, $—NHCH_3$, $—NHC(CH_3)_3$, $—NH(CH_2)Ph$ and $—NH(CH_2)_2O(CH_2)Ph$.

In an exemplary embodiment, X, Y and $R^d$ are as described herein; b is 1; $R^b$ is selected from the group consisting of $—N(CH_3)_2$, $—N(CH_3)(CH_2)_2OH$, $—N(CH_3)(CH_2)_2OCH_3$, $—NHCH_3$, $—NHC(CH_3)_3$, $—NH(CH_2)Ph$, and $—NH(CH_2)_2O(CH_2)Ph$.

In an exemplary embodiment, X, Y and $R^d$ are as described herein; b is 1; $R^b$ is $—NR^4R^5$, wherein $R^4$ and $R^5$, together with the nitrogen to which they are attached, are joined to form a substituted or unsubstituted 4 to 8 membered ring. In an exemplary embodiment, the only non-carbon atom which forms the ring is the nitrogen to which $R^4$ and $R^5$ are attached. In an exemplary embodiment, X, Y and $R^d$ are as described herein; b is 1; $R^b$ is $—NR^4R^5$, wherein $R^4$ and $R^5$, together with the nitrogen to which they are attached, are joined to form substituted or unsubstituted pyrrolidinyl or substituted or unsubstituted piperidinyl. In an exemplary embodiment, X, Y and $R^d$ are as described herein; b is 1; $R^b$ is $—NR^4R^5$, wherein $R^4$ and $R^5$, together with the nitrogen to which they are attached, are joined to form unsubstituted pyrrolidinyl or unsubstituted piperidinyl. In an exemplary embodiment, the only non-carbon atom which forms the ring is nitrogen. In an exemplary embodiment, the ring contains one nitrogen atom and one oxygen atom. In an exemplary embodiment, the ring contains one nitrogen atom and one oxygen atom. In an exemplary embodiment, X, Y and $R^d$ are as described herein; b is 1; $R^b$ is $—NR^4R^5$, wherein $R^4$ and $R^5$, together with the nitrogen to which they are attached, are joined to form substituted or unsubstituted morpholinyl. In an exemplary embodiment, X, Y and $R^d$ are as described herein; b is 1; $R^b$ is $—NR^4R^5$, wherein $R^4$ and $R^5$, together with the nitrogen to which they are attached, are joined to form unsubstituted morpholinyl.

In an exemplary embodiment, the invention provides a compound having a structure according to the formula:

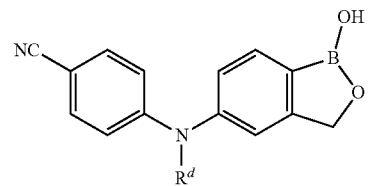

wherein $R^d$ is selected from the group consisting of H, unsubstituted $C_1$-$C_6$ alkyl and $—C(O)OR^{10}$, wherein $R^{10}$ is H or unsubstituted $C_1$-$C_6$ alkyl. In an exemplary embodiment, $R^d$ is selected from the group consisting of H, methyl, and t-butoxycarbonyl. In an exemplary embodiment, $R^d$ is selected from the group consisting of methyl, ethyl, propyl, isopropyl, butyl, pentyl and hexyl. In an exemplary embodiment, $R^{10}$ is selected from the group consisting of methyl, ethyl, propyl, isopropyl, butyl, isobutyl, sec-butyl, pentyl, isopentyl, cyclopentyl, hexyl, isohexyl and cyclohexyl.

In an exemplary embodiment, the compound has a structure according to the following formula:

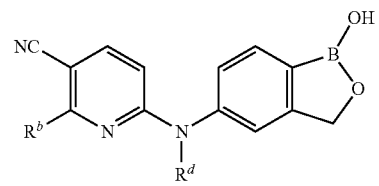

and salts thereof, wherein $R^b$ and $R^d$ are as described herein. In an exemplary embodiment, $R^b$ is selected from the group consisting of OR⁴, NR⁴R⁵, SR⁴, —S(O)R⁴, —S(O)₂R⁴, —S(O)₂NR⁴R⁵, —C(O)R⁴, —C(O)OR⁴, —C(O)NR⁴R⁵, nitro, cyano, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein each R⁴ and R⁵ are as described herein. In an exemplary embodiment, R$^b$ is as described herein and R$^d$ is H. In an exemplary embodiment, R$^b$ is as described herein and R$^d$ is unsubstituted C₁-C₆ alkyl. In an exemplary embodiment, R$^b$ is as described herein and R$^d$ is methyl. In an exemplary embodiment, R$^b$ is as described herein and R$^d$ is ethyl. In an exemplary embodiment, R$^b$ is as described herein and R$^d$ is unsubstituted C₃ alkyl.

In an exemplary embodiment, the compound has a structure according to the following formula:

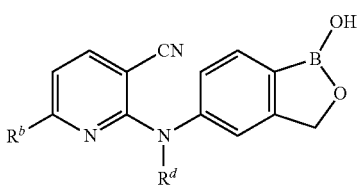

and salts thereof, wherein R$^b$ and R$^d$ are as described herein. In an exemplary embodiment, R$^b$ is as described herein and R$^d$ is H. In an exemplary embodiment, R$^b$ is as described herein and R$^d$ is unsubstituted C₁-C₆ alkyl. In an exemplary embodiment, R$^b$ is as described herein and R$^d$ is methyl. In an exemplary embodiment, R$^b$ is as described herein and R$^d$ is ethyl. In an exemplary embodiment, R$^b$ is as described herein and R$^d$ is unsubstituted C₃ alkyl.

In an exemplary embodiment, the compound has a structure according to the following formula:

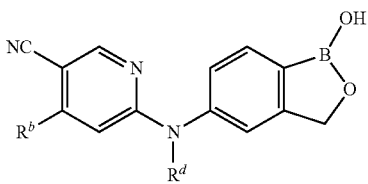

and salts thereof, wherein R$^b$ and R$^d$ are as described herein. In an exemplary embodiment, R$^b$ is as described herein and R$^d$ is H. In an exemplary embodiment, R$^b$ is as described herein and R$^d$ is unsubstituted C₁-C₆ alkyl. In an exemplary embodiment, R$^b$ is as described herein and R$^d$ is methyl. In an exemplary embodiment, R$^b$ is as described herein and R$^d$ is ethyl. In an exemplary embodiment, R$^b$ is as described herein and R$^d$ is unsubstituted C₃ alkyl.

In an exemplary embodiment, the compound has a structure according to the following formula:

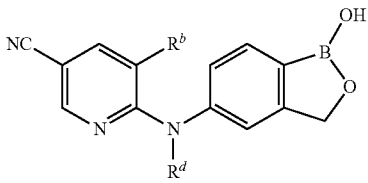

In an exemplary embodiment, the compound has a structure according to the following formula:

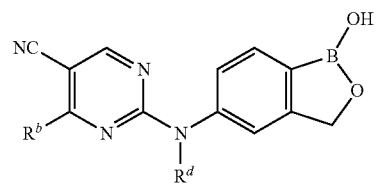

and salts thereof, wherein R$^b$ and R$^d$ are as described herein. In an exemplary embodiment, R$^b$ is as described herein and R$^d$ is H. In an exemplary embodiment, R$^b$ is as described herein and R$^d$ is unsubstituted C₁-C₆ alkyl. In an exemplary embodiment, R$^b$ is as described herein and R$^d$ is methyl. In an exemplary embodiment, R$^b$ is as described herein and R$^d$ is ethyl. In an exemplary embodiment, R$^b$ is as described herein and R$^d$ is unsubstituted C₃ alkyl.

In an exemplary embodiment, the compound has a structure according to the following formula:

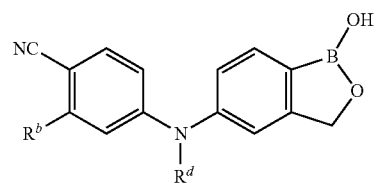

and salts thereof, wherein R$^b$ and R$^d$ are as described herein. In an exemplary embodiment, R$^b$ is as described herein and R$^d$ is H. In an exemplary embodiment, R$^b$ is as described herein and R$^d$ is unsubstituted C₁-C₆ alkyl. In an exemplary embodiment, R$^b$ is as described herein and R$^d$ is methyl. In an exemplary embodiment, R$^b$ is as described herein and R$^d$ is ethyl. In an exemplary embodiment, R$^b$ is as described herein and R$^d$ is unsubstituted C₃ alkyl.

In an exemplary embodiment, the compound has a structure according to the following formula:

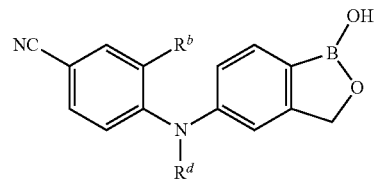

and salts thereof, wherein R$^b$ and R$^d$ are as described herein. In an exemplary embodiment, R$^b$ is as described herein and R$^d$ is H. In an exemplary embodiment, R$^b$ is as described herein and R$^d$ is unsubstituted C₁-C₆ alkyl. In an exemplary embodiment, R$^b$ is as described herein and R$^d$ is methyl. In an exemplary embodiment, R$^b$ is as described herein and R$^d$ is ethyl. In an exemplary embodiment, $R^b$ is as described herein and $R^d$ is unsubstituted $C_3$ alkyl.

In an exemplary embodiment, the compound has a structure according to the following formula:

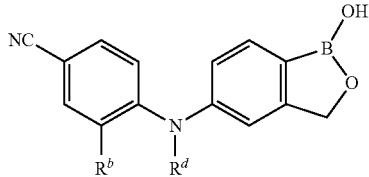

and salts thereof, wherein $R^b$ and $R^d$ are as described herein. In an exemplary embodiment, $R^b$ is as described herein and $R^d$ is H. In an exemplary embodiment, $R^b$ is as described herein and $R^d$ is unsubstituted $C_1$-$C_6$ alkyl. In an exemplary embodiment, $R^b$ is as described herein and $R^d$ is methyl. In an exemplary embodiment, $R^b$ is as described herein and $R^d$ is ethyl. In an exemplary embodiment, $R^b$ is as described herein and $R^d$ is unsubstituted $C_3$ alkyl.

In an exemplary embodiment, the compound has a structure according to the following formula:

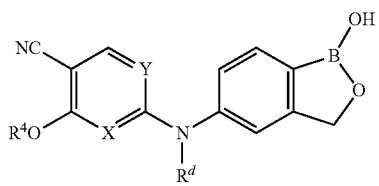

wherein $R^4$ is unsubstituted $C_1$-$C_6$ alkyl; X is CH or N; Y is CH or N; and $R^d$ is as described herein. In an exemplary embodiment, X, Y and $R^4$ are as described herein and $R^d$ is H. In an exemplary embodiment, X, Y and $R^4$ are as described herein and $R^d$ is unsubstituted $C_1$-$C_6$ alkyl. In an exemplary embodiment, X, Y and $R^4$ are as described herein and $R^d$ is methyl. In an exemplary embodiment, X, Y and $R^4$ are as described herein and $R^d$ is ethyl. In an exemplary embodiment, X, Y and $R^4$ are as described herein and $R^d$ is unsubstituted $C_3$ alkyl.

In an exemplary embodiment, the compound has a structure according to the following formula:

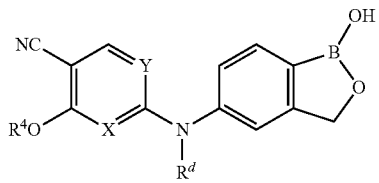

wherein $R^4$ is unsubstituted $C_1$-$C_6$ cycloalkyl; X is CH or N; Y is CH or N; and $R^d$ is as described herein. In an exemplary embodiment, X, Y and $R^4$ are as described herein and $R^d$ is H. In an exemplary embodiment, X, Y and $R^4$ are as described herein and $R^d$ is unsubstituted $C_1$-$C_6$ alkyl. In an exemplary embodiment, X, Y and $R^4$ are as described herein and $R^d$ is methyl. In an exemplary embodiment, X, Y and $R^4$ are as described herein and $R^d$ is ethyl. In an exemplary embodiment, X, Y and $R^4$ are as described herein and $R^d$ is unsubstituted $C_3$ alkyl.

In an exemplary embodiment, the compound has a structure according to the following formula:

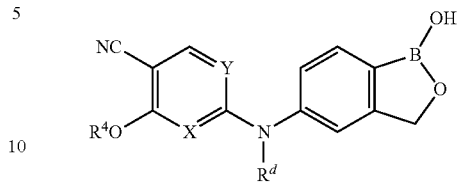

wherein $R^4$ is unsubstituted $C_1$-$C_6$ alkyl; X is CH or N; Y is CH or N; and $R^d$ is as described herein. In an exemplary embodiment, X, Y and $R^4$ are as described herein and $R^d$ is H. In an exemplary embodiment, X, Y and $R^4$ are as described herein and $R^d$ is unsubstituted $C_1$-$C_6$ alkyl. In an exemplary embodiment, X, Y and $R^4$ are as described herein and $R^d$ is methyl. In an exemplary embodiment, X, Y and $R^4$ are as described herein and $R^d$ is ethyl. In an exemplary embodiment, X, Y and $R^4$ are as described herein and $R^d$ is unsubstituted $C_3$ alkyl.

In an exemplary embodiment, the compound has a structure according to the following formula:

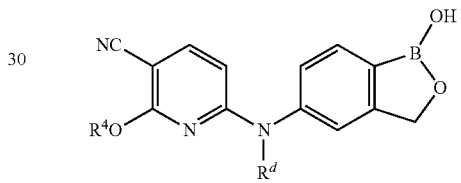

wherein $R^4$, X, Y and $R^d$ are as described herein. In an exemplary embodiment, the compound has a structure according to the following formula:

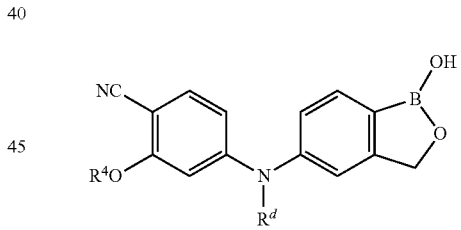

wherein $R^4$, X, Y and $R^d$ are as described herein.

In an exemplary embodiment, the compound has a structure which is selected from the group consisting of

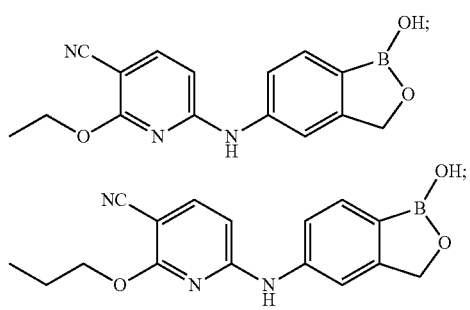

-continued

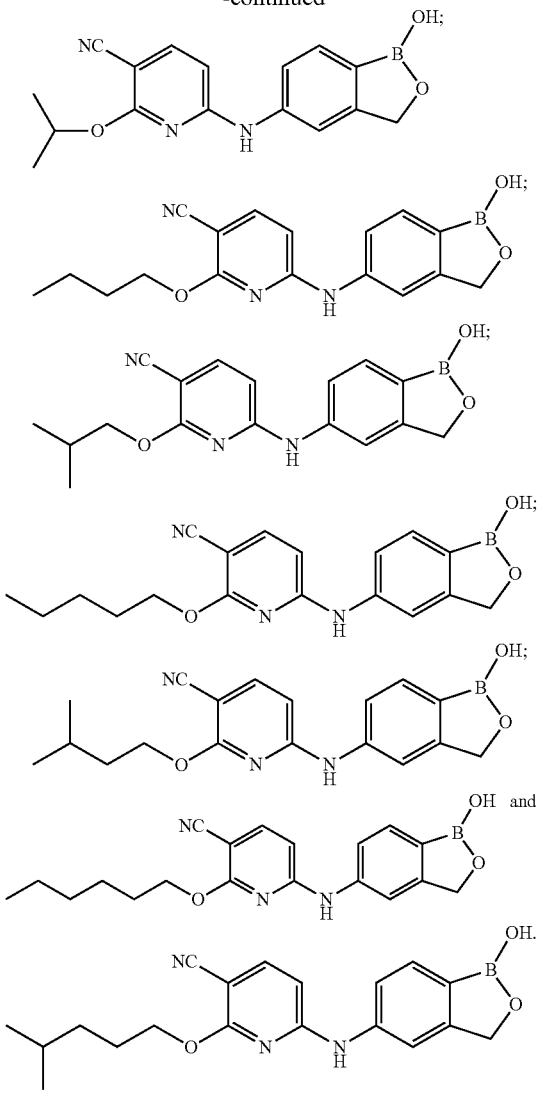

In an exemplary embodiment, the compound has a structure according to the following formula:

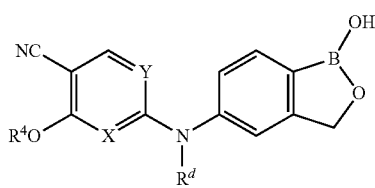

wherein $R^4$ is unsubstituted $C_3$-$C_8$ cycloalkyl; X is CH or N; Y is CH or N; and $R^d$ is as described herein. In an exemplary embodiment, X, Y and $R^4$ are as described herein and $R^d$ is H. In an exemplary embodiment, X, Y and $R^4$ are as described herein and $R^d$ is unsubstituted $C_1$-$C_6$ alkyl. In an exemplary embodiment, X, Y and $R^4$ are as described herein and $R^d$ is methyl. In an exemplary embodiment, X, Y and $R^4$ are as described herein and $R^d$ is ethyl. In an exemplary embodiment, X, Y and $R^4$ are as described herein and $R^d$ is unsubstituted $C_3$ alkyl. In an exemplary embodiment, the compound has a structure according to the following formula:

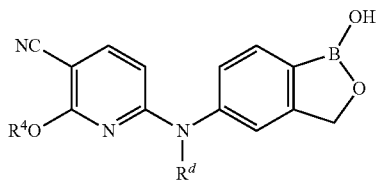

wherein $R^4$, X, Y and $R^d$ are as described herein. In an exemplary embodiment, the compound has a structure according to the following formula:

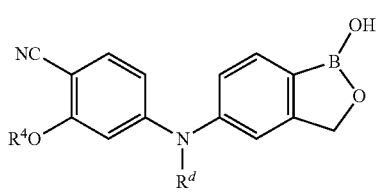

wherein $R^4$, X, Y and $R^d$ are as described herein.

In an exemplary embodiment, the compound has a structure which is selected from the group consisting of:

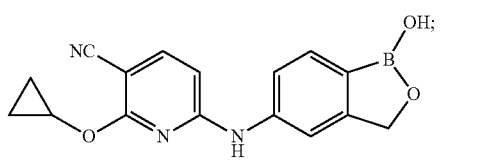

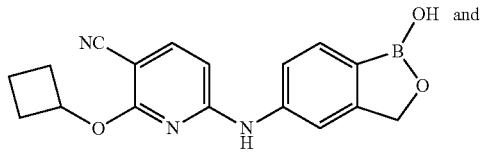

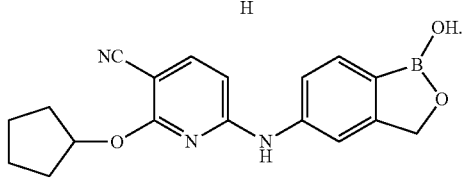

In an exemplary embodiment, the compound has a structure according to the following formula:

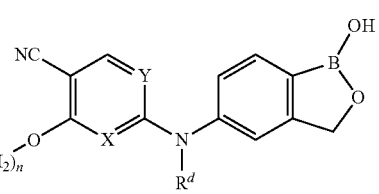

wherein n is an integer selected from 1 to 6; $R^{11}$ is unsubstituted $C_3$-$C_8$ cycloalkyl; X, Y and $R^d$ are as described herein. In an exemplary embodiment, X, Y, $R^d$ and $R^{11}$ are as described herein and n is 1. In an exemplary embodiment, X, Y, $R^d$ and $R^{11}$ are as described herein and n is 2. In an exemplary embodiment, X, Y, $R^d$ and $R^{11}$ are as described herein and n is 3. In an exemplary embodiment, X, Y, $R^d$ and $R^{11}$ are as described herein and n is 4. In an exemplary embodiment, X, Y, n and $R^{11}$ are as described herein and $R^d$ is H. In an exemplary embodiment, X, Y, n and $R^{11}$ are as described herein and $R^d$ is unsubstituted $C_1$-$C_6$ alkyl. In an exemplary embodiment, X, Y, n and $R^{11}$ are as described herein and $R^d$ is methyl. In an exemplary embodiment, X, Y, n and $R^{11}$ are as described herein and $R^d$ is ethyl. In an exemplary embodiment, X, Y, n and $R^{11}$ are as described herein and $R^d$ is unsubstituted $C_3$ alkyl. In an exemplary embodiment, the compound has a structure according to the following formula:

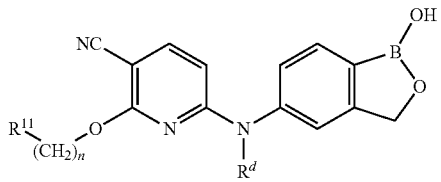

wherein n, $R^{11}$, X, Y and $R^d$ are as described herein. In an exemplary embodiment, the compound has a structure according to the following formula:

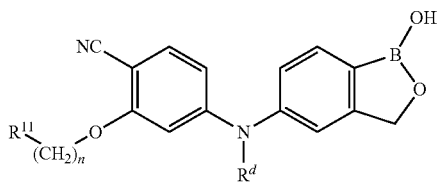

wherein n, $R^{11}$, X, Y and $R^d$ are as described herein.

In an exemplary embodiment, the compound has a structure which is selected from the group consisting of

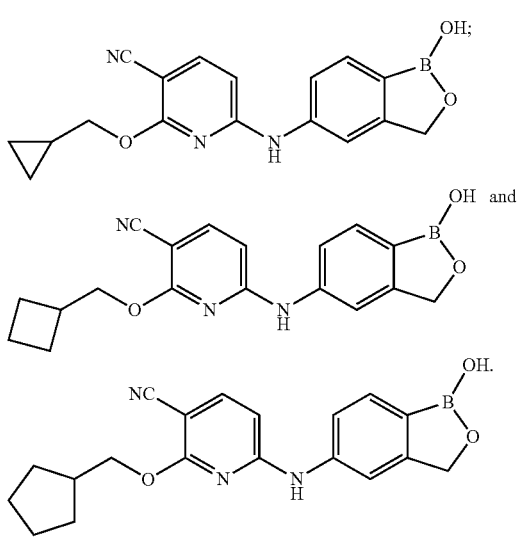

In an exemplary embodiment, the compound has a structure according to the following formula:

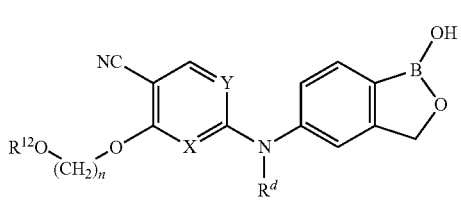

wherein n is an integer selected from 1 to 6; $R^{12}$ is H or unsubstituted $C_1$-$C_6$ alkyl or —C(O)$R^{13}$, wherein $R^{13}$ is unsubstituted $C_1$-$C_6$ alkyl; X, Y and $R^d$ are as described herein. In an exemplary embodiment, X, Y, $R^d$ and $R^{12}$ are as described herein and n is 1. In an exemplary embodiment, X, Y, $R^d$ and $R^{12}$ are as described herein and n is 2. In an exemplary embodiment, X, Y, $R^d$ and $R^{12}$ are as described herein and n is 3. In an exemplary embodiment, X, Y, $R^d$ and $R^{12}$ are as described herein and n is 4. In an exemplary embodiment, X, Y, $R^d$ and n are as described herein and $R^{12}$ is H. In an exemplary embodiment, X, Y, $R^d$ and n are as described herein and $R^{12}$ is methyl. In an exemplary embodiment, X, Y, $R^d$ and n are as described herein and $R^{12}$ is ethyl. In an exemplary embodiment, X, Y, $R^d$ and n are as described herein and $R^{12}$ is isopropyl. In an exemplary embodiment, X, Y, $R^d$ and n are as described herein and $R^{12}$ is C(O)CH$_3$. In an exemplary embodiment, X, Y, $R^{12}$ and n are as described herein and $R^d$ is H. In an exemplary embodiment, X, Y, $R^{12}$ and n are as described herein and $R^d$ is unsubstituted $C_1$-$C_6$ alkyl. In an exemplary embodiment, X, Y, $R^{12}$ and n are as described herein and $R^d$ is methyl. In an exemplary embodiment, X, Y, $R^{12}$ and n are as described herein and $R^d$ is ethyl. In an exemplary embodiment, X, Y, $R^{12}$ and n are as described herein and $R^d$ is unsubstituted $C_3$ alkyl. In an exemplary embodiment, the compound has a structure according to the following formula:

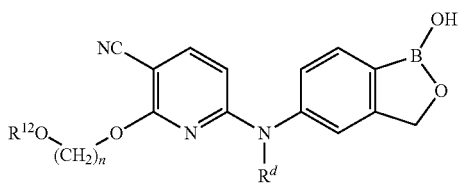

wherein n, $R^{12}$ and $R^d$ are as described herein. In an exemplary embodiment, the compound has a structure according to the following formula:

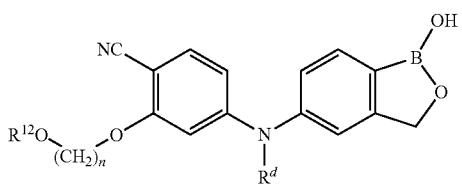

wherein n, $R^{12}$ and $R^d$ are as described herein.

In an exemplary embodiment, the compound has a structure which is selected from the group consisting of

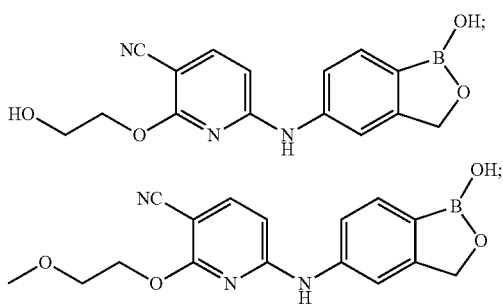

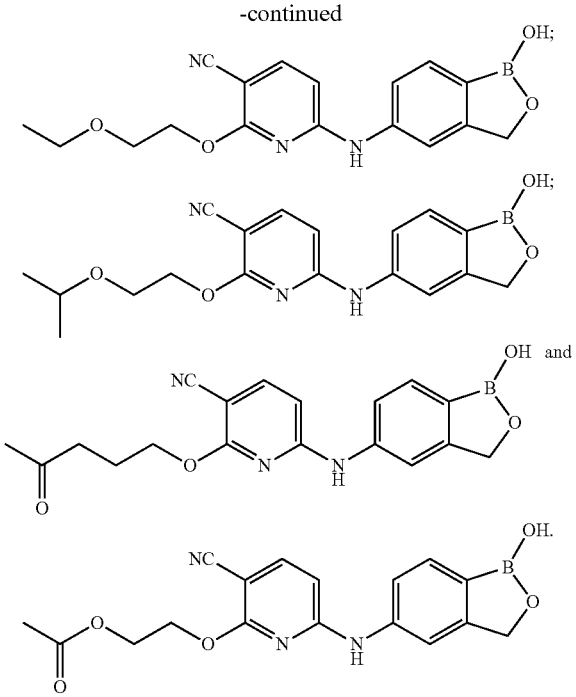

In an exemplary embodiment, the compound has a structure according to the following formula:

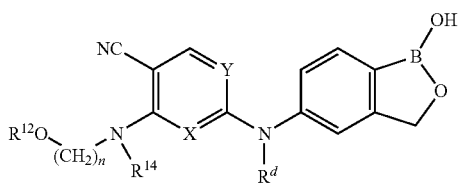

wherein n is an integer selected from 1 to 6; $R^{12}$ is H or unsubstituted $C_1$-$C_6$ alkyl or —C(O)$R^{13}$, wherein $R^{13}$ is unsubstituted $C_1$-$C_6$ alkyl; $R^{14}$ is H or unsubstituted $C_1$-$C_6$ alkyl; X, Y and $R^d$ are as described herein. In an exemplary embodiment, X, Y, $R^{12}$, $R^{14}$ and $R^d$ are as described herein and n is 1. In an exemplary embodiment, X, Y, $R^{12}$, $R^{14}$ and $R^d$ are as described herein and n is 2. In an exemplary embodiment, X, Y, $R^{12}$, $R^{14}$ and $R^d$ are as described herein and n is 3. In an exemplary embodiment, X, Y, $R^{12}$, $R^{14}$ and $R^d$ are as described herein and n is 4. In an exemplary embodiment, X, Y, n, $R^{14}$ and $R^d$ are as described herein and $R^{12}$ is H. In an exemplary embodiment, X, Y, $R^d$, n, $R^{14}$ are as described herein and $R^{12}$ is methyl. In an exemplary embodiment, X, Y, $R^d$, n, $R^{14}$ are as described herein and $R^{12}$ is ethyl. In an exemplary embodiment, X, Y, $R^d$, n, $R^{14}$ are as described herein and $R^{12}$ is isopropyl. In an exemplary embodiment, X, Y, $R^d$, n, $R^{14}$ are as described herein and $R^{12}$ is C(O)$CH_3$. In an exemplary embodiment, X, Y, $R^d$, n, $R^{12}$ are as described herein and $R^{14}$ is H. In an exemplary embodiment, X, Y, $R^d$, n, $R^{12}$ are as described herein and $R^{14}$ is methyl. In an exemplary embodiment, X, Y, $R^{14}$, n, $R^{12}$ are as described herein and $R^d$ is H. In an exemplary embodiment, X, Y, $R^{14}$, n, $R^{12}$ are as described herein and $R^d$ is unsubstituted $C_1$-$C_6$ alkyl. In an exemplary embodiment, X, Y, $R^{14}$, n, $R^{12}$ are as described herein and $R^d$ is methyl. In an exemplary embodiment, X, Y, $R^{14}$, n, $R^{12}$ are as described herein and $R^d$ is ethyl. In an exemplary embodiment, X, Y, $R^{14}$, n, $R^{12}$ are described herein and $R^d$ is unsubstituted $C_3$ alkyl. In an exemplary embodiment, the compound has a structure according to the following formula:

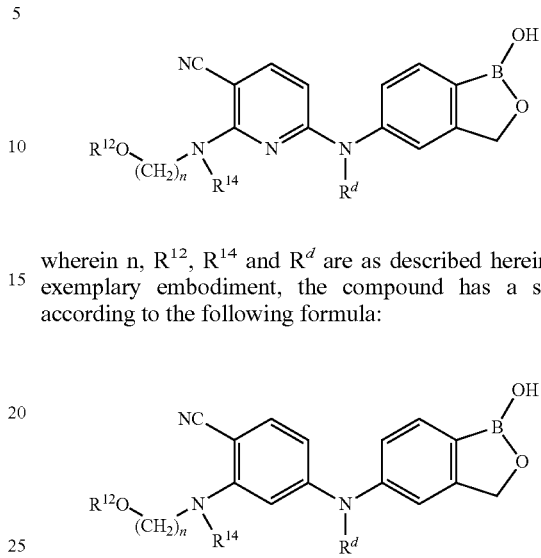

wherein n, $R^{12}$, $R^{14}$ and $R^d$ are as described herein. In an exemplary embodiment, the compound has a structure according to the following formula:

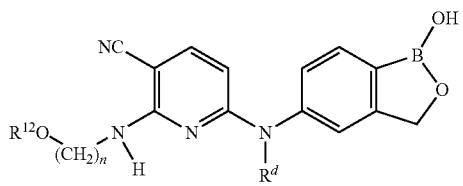

wherein n, $R^{12}$, $R^{14}$ and $R^d$ are as described herein. In an exemplary embodiment, the compound has a structure according to the following formula:

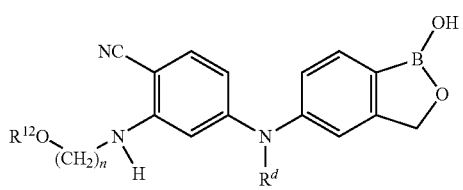

wherein n, $R^{12}$ and $R^d$ are as described herein. In an exemplary embodiment, the compound has a structure according to the following formula:

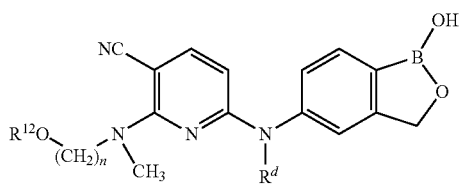

wherein n, $R^{12}$ and $R^d$ are as described herein. In an exemplary embodiment, the compound has a structure according to the following formula:

wherein n, $R^{12}$ and $R^d$ are as described herein. In an exemplary embodiment, the compound has a structure according to the following formula:

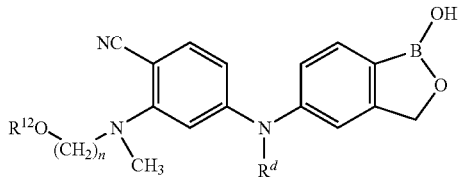

wherein n, $R^{12}$ and $R^d$ are as described herein.

In an exemplary embodiment, the compound has a structure which is selected from the group consisting of

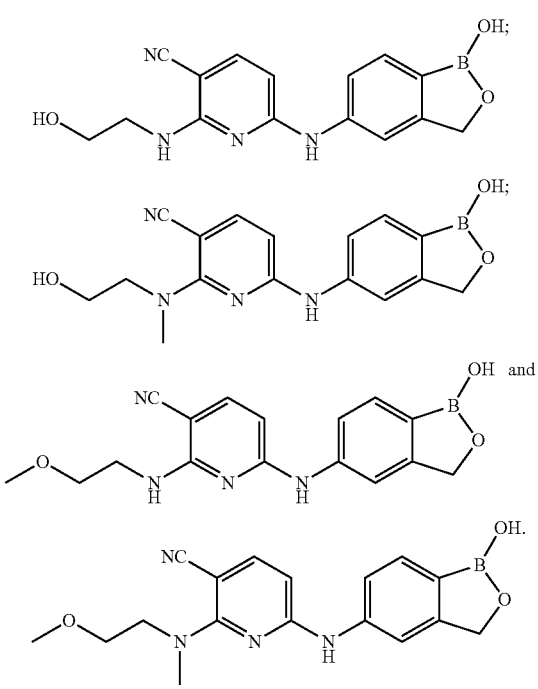

In an exemplary embodiment, the invention provides a compound having a structure according to the formula:

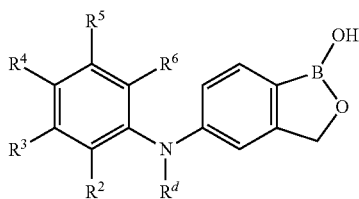

wherein $R^d$ is selected from the group consisting of H, unsubstituted $C_1$-$C_6$ alkyl, $COR^{10}$, and —C(O)$OR^{10}$, wherein $R^{10}$ is selected from the group consisting of H and unsubstituted $C_1$-$C_6$ alkyl, and the possibilities for $R^2$, $R^3$, $R^4$, $R^5$ and $R^6$ are presented in the following table, or a salt thereof.

| $R^2$ | $R^3$ | $R^4$ | $R^5$ | $R^6$ |
|---|---|---|---|---|
| CN | H  | H  | H  | H  |
| H  | CN | H  | H  | H  |
| H  | H  | CN | H  | H  |
| H  | H  | H  | CN | H  |
| H  | H  | H  | H  | CN |
| CN | CN | H  | H  | H  |
| CN | H  | CN | H  | H  |
| CN | H  | H  | CN | H  |
| CN | H  | H  | H  | CN |
| H  | CN | CN | H  | H  |
| H  | CN | H  | CN | H  |
| H  | CN | H  | H  | CN |
| H  | H  | CN | CN | H  |
| H  | H  | CN | H  | CN |
| H  | H  | H  | CN | CN |
| H  | H  | CN | H  | CN |

In an exemplary embodiment, for any of the entries in the above table, $R^d$ is H. In an exemplary embodiment, for any of the entries in the above table, $R^d$ is methyl. In an exemplary embodiment, for any of the entries in the above table, $R^d$ is ethyl. In an exemplary embodiment, for any of the entries in the above table, $R^d$ is propyl. In an exemplary embodiment, for any of the entries in the above table, $R^d$ is isopropyl. In an exemplary embodiment, for any of the entries in the above table, $R^d$ is unsubstituted $C_4$ alkyl. In an exemplary embodiment, for any of the entries in the above table, $R^d$ is selected from the group consisting of butyl, isobutyl, secbutyl and t-butyl. In an exemplary embodiment, for any of the entries in the above table, $R^d$ is unsubstituted $C_5$ alkyl. In an exemplary embodiment, for any of the entries in the above table, $R^d$ is pentyl. In an exemplary embodiment, for any of the entries in the above table, $R^d$ is isopentyl. In an exemplary embodiment, for any of the entries in the above table, $R^d$ is unsubstituted $C_6$ alkyl. In an exemplary embodiment, for any of the entries in the above table, $R^d$ is —C(O)$OR^{10}$, wherein $R^{10}$ is $C_1$-$C_6$ unsubstituted alkyl. In an exemplary embodiment, for any of the entries in the above table, $R^d$ is —C(O)$OCH_3$. In an exemplary embodiment, for any of the entries in the above table, $R^d$ is —C(O)$OCH_2CH_3$. In an exemplary embodiment, for any of the entries in the above table, $R^d$ is —C(O)$OR^{10}$, wherein $R^{10}$ is propyl. In an exemplary embodiment, for any of the entries in the above table, $R^d$ is —C(O)$OR^{10}$, wherein $R^{10}$ is isopropyl. In an exemplary embodiment, for any of the entries in the above table, $R^d$ is —C(O)$OR^{10}$, wherein $R^{10}$ is n-butyl. In an exemplary embodiment, for any of the entries in the above table, $R^d$ is —C(O)$OR^{10}$, wherein $R^{10}$ is isobutyl. In an exemplary embodiment, for any of the entries in the above table, $R^d$ is —C(O)$OR^{10}$, wherein $R^{10}$ is t-butyl. In an exemplary embodiment, for any of the entries in the above table, $R^d$ is —C(O)$OR^{10}$, wherein $R^{10}$ is sec-butyl. In an exemplary embodiment, for any of the entries in the above table, $R^d$ is —C(O)$OR^{10}$, wherein $R^{10}$ is pentyl. In an exemplary embodiment, for any of the entries in the above table, $R^d$ is —C(O)$OR^{10}$, wherein $R^{10}$ is isopentyl. In an exemplary embodiment, for any of the entries in the above table, $R^d$ is —C(O)$OR^{10}$, wherein $R^{10}$ is hexyl. In an exemplary embodiment, for any of the entries in the above table, $R^d$ is —C(O)OH.

In an exemplary embodiment, the invention provides a compound having a structure according to the formula:

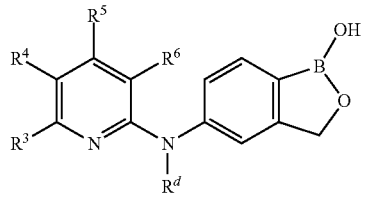

wherein $R^d$ is selected from the group consisting of H, unsubstituted $C_1$-$C_6$ alkyl, $COR^{10}$, and —$C(O)OR^{10}$, wherein $R^{10}$ is H or unsubstituted $C_1$-$C_6$ alkyl as described herein, and the possibilities for $R^3$, $R^4$, $R^5$ and $R^6$ are presented in the following table, or a salt thereof.

| $R^3$ | $R^4$ | $R^5$ | $R^6$ |
|---|---|---|---|
| CN | H | H | H |
| H | CN | H | H |
| H | H | CN | H |
| H | H | H | CN |
| CN | CN | H | H |
| CN | H | CN | H |
| CN | H | H | CN |
| H | CN | CN | H |
| H | CN | H | CN |
| H | H | CN | CN |
| H | CN | H | CN |

In an exemplary embodiment, for any of the entries in the above table, $R^d$ is H. In an exemplary embodiment, for any of the entries in the above table, $R^d$ is methyl. In an exemplary embodiment, for any of the entries in the above table, $R^d$ is ethyl. In an exemplary embodiment, for any of the entries in the above table, $R^d$ is propyl. In an exemplary embodiment, for any of the entries in the above table, $R^d$ is isopropyl. In an exemplary embodiment, for any of the entries in the above table, $R^d$ is unsubstituted $C_4$ alkyl. In an exemplary embodiment, for any of the entries in the above table, $R^d$ is selected from the group consisting of butyl, isobutyl, secbutyl and t-butyl. In an exemplary embodiment, for any of the entries in the above table, $R^d$ is unsubstituted $C_5$ alkyl. In an exemplary embodiment, for any of the entries in the above table, $R^d$ is pentyl. In an exemplary embodiment, for any of the entries in the above table, $R^d$ is isopentyl. In an exemplary embodiment, for any of the entries in the above table, $R^d$ is unsubstituted $C_6$ alkyl. In an exemplary embodiment, for any of the entries in the above table, $R^d$ is —$C(O)OR^{10}$, wherein $R^{10}$ is $C_1$-$C_6$ unsubstituted alkyl. In an exemplary embodiment, for any of the entries in the above table, $R^d$ is —$C(O)OCH_3$. In an exemplary embodiment, for any of the entries in the above table, $R^d$ is —$C(O)OCH_2CH_3$. In an exemplary embodiment, for any of the entries in the above table, $R^d$ is —$C(O)OR^{10}$, wherein $R^{10}$ is propyl. In an exemplary embodiment, for any of the entries in the above table, $R^d$ is —$C(O)OR^{10}$, wherein $R^{10}$ is isopropyl. In an exemplary embodiment, for any of the entries in the above table, $R^d$ is —$C(O)OR^{10}$, wherein $R^{10}$ is n-butyl. In an exemplary embodiment, for any of the entries in the above table, $R^d$ is —$C(O)OR^{10}$, wherein $R^{10}$ is isobutyl. In an exemplary embodiment, for any of the entries in the above table, $R^d$ is —$C(O)OR^{10}$, wherein $R^{10}$ is t-butyl. In an exemplary embodiment, for any of the entries in the above table, $R^d$ is —$C(O)OR^{10}$, wherein $R^{10}$ is sec-butyl. In an exemplary embodiment, for any of the entries in the above table, $R^d$ is —$C(O)OR^{10}$, wherein $R^{10}$ is pentyl. In an exemplary embodiment, for any of the entries in the above table, $R^d$ is —$C(O)OR^{10}$, wherein $R^{10}$ is isopentyl. In an exemplary embodiment, for any of the entries in the above table, $R^d$ is —$C(O)OR^{10}$, wherein $R^{10}$ is hexyl. In an exemplary embodiment, for any of the entries in the above table, $R^d$ is —$C(O)OH$.

In another exemplary embodiment, the invention provides poly- or multi-valent species of the compounds of the invention. In an exemplary embodiment, the invention provides a dimer of a compound of the invention. In an exemplary embodiment, the invention provides a dimer of a compound described herein.

In an exemplary embodiment, the invention provides an anhydride of a compound of the invention. In an exemplary embodiment, the invention provides an anhydride of a compound described herein.

In an exemplary embodiment, the invention provides a trimer of a compound of the invention. In an exemplary embodiment, the invention provides a trimer of a compound described herein.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

In an exemplary embodiment, alkyl is linear alkyl. In an exemplary embodiment, alkyl is branched alkyl. In an exemplary embodiment, heteroalkyl is linear heteroalkyl. In an exemplary embodiment, heteroalkyl is branched heteroalkyl.

IIIe. Methods of Making the Compounds

Compounds of use in the present invention can be prepared using commercially available starting materials or known intermediates. Compounds of use in the present invention can be prepared using synthetic methods known in the art or described herein.

The following exemplary schemes illustrate methods of preparing boron-containing molecules of the present invention. These methods are not limited to producing the compounds shown, but can be used to prepare a variety of molecules such as the compounds and complexes described herein. The compounds of the present invention can also be synthesized by methods not explicitly illustrated in the schemes but are well within the skill of one in the art. The compounds can be prepared using readily available materials of known intermediates.

The compounds of the invention can be produced according to the strategies described herein. Strategy A is described below for the production of 5-(arylamino)benzoxaborole derivatives:

Strategy A:

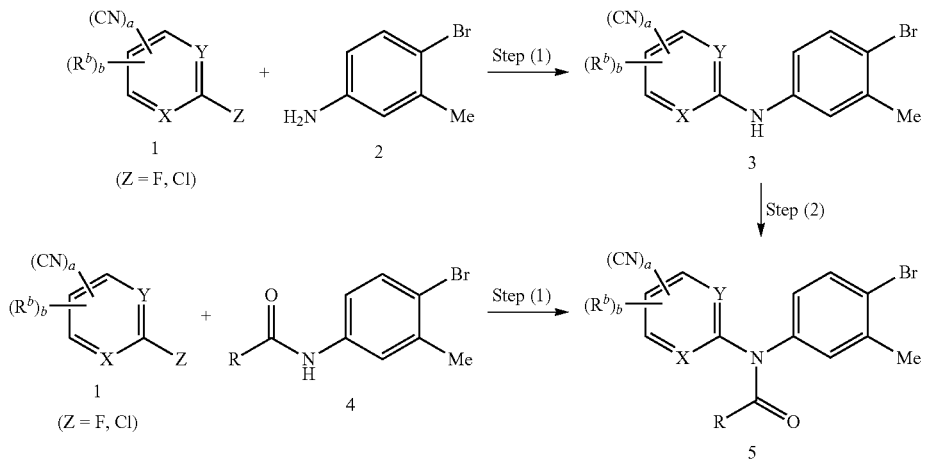

Step 1: Compounds 1 and 2 are reacted ion the presence of a base to give compound 3. The base is typically sodium hydride, potassium tert-butoxide, sodium hydroxide, potassium hydroxide, sodium carbonate, potassium carbonate, and the like. The solvent is typically N,N-dimethylformamide, N,N-dimethylacetamide, tetrahydrofuran, 1,4-dioxane, and the like. The reaction is carried out at between −20° C. to the boiling point of the solvent used, preferably between 0° C. and 60° C., and is complete in from 1 to about 48 hours. Alternatively, N-acylated or alkoxycarbonylated compound 4 can be used for the same reaction. Compounds 1 and 2, or 1 and 4 are typically the same mol amount, but one can also be excess to the other.

Step 2: Compound 2 is reacted with 1 to 10 equivalents of acid chloride, acid anhydride, dialkyl dicarbonate, or alkyl chloroformate to give compound 5. A base, such as triethylamine, diisopropylethylamine, pyridine, 4-N,N-dimethylaminopyridine, sodium carbonate, or potassium carbonate, and the like, may be used. The solvent is typically chosen from acetonitrile, dichloromethane, chloroform, N,N-dimethylformamide, N,N-dimethylacetamide, tetrahydrofuran, 1,4-dioxane, and the like. The reaction is carried out at between −20° C. to the boiling point of the solvent used, preferably between 0° C. and 60° C., and is complete in from 1 to about 48 hours.

Step 3: Compound 5 is treated with 0.9 to 3 equivalents of N-bromosuccinimide in the presence of a radical initiator to give compound 6. A radical initiator is typically chosen from azobisisobutyronitrile or benzoyl peroxide. Tetrachloromethane is typically used as the solvent. The reaction is carried out at room temperature to reflux. The reaction is complete in from about 1 to about 24 hours.

Step 4: Compound 6 is treated with 1 to 10 equivalents of sodium carbonate or potassium carbonate to give compound 7. The solvent is typically chosen from acetonitrile, dichloromethane, chloroform, N,N-dimethylformamide, N,N-dimethylacetamide, tetrahydrofuran, 1,4-dioxane, and the like. The reaction is carried out at between 0° C. to the boiling point of the solvent used, preferably between 50° C. and 80° C., and is complete in from 1 to about 48 hours.

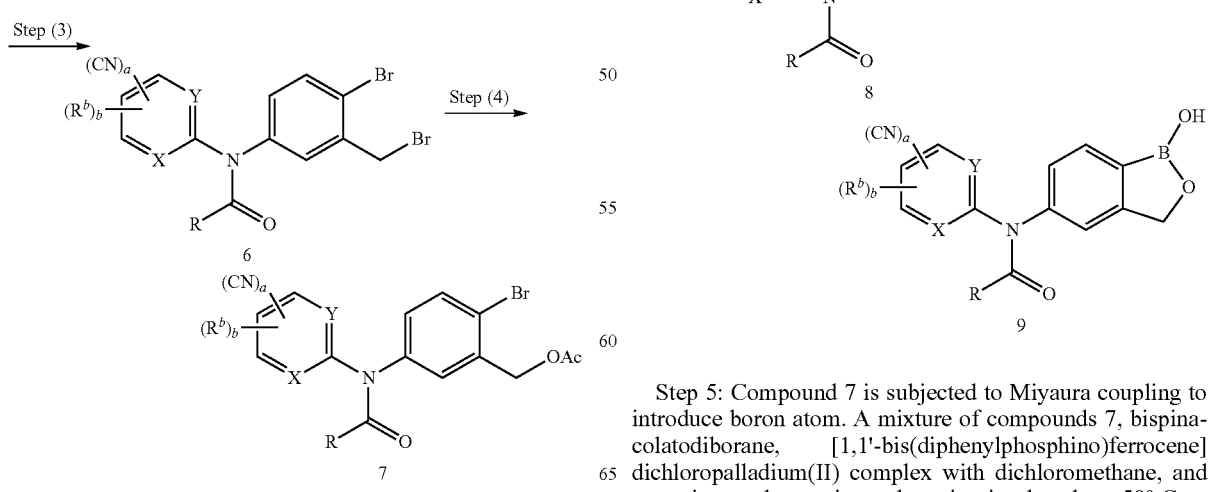

Step 5: Compound 7 is subjected to Miyaura coupling to introduce boron atom. A mixture of compounds 7, bispinacolatodiborane, [1,1'-bis(diphenylphosphino)ferrocene] dichloropalladium(II) complex with dichloromethane, and potassium carbonate in a solvent is stirred at about 50° C. to reflux. The solvent is chosen from 1,4-dioxane, 1,2- dimethoxyethane, tetrahydrofuran, dimethylsulfoxide, N,N-dimethylformamide, toluene, and the like. The palladium catalyst is used at from about 1 to about 5 mol %, and the base is used from about 2 to about 5 equivalents. The reaction is completed in from about 1 to about 24 hours.

Step 6: Compound 8 is treated with a base, such as sodium hydroxide, potassium hydroxide, sodium carbonate, potassium carbonate to give compound 9. The base is used from about 0.5 to about 5 equivalents. The solvent is typically from methanol, ethanol, tetrahydrofuran, 1,2-dimethoxyethane, 1,4-dioxane, and the like. The reaction is carried out at about 0° C. to room temperature, and complete in from about 1 to about 24 hours. Pinacol is removed by washing the organic layer with aqueous boric acid during the extraction, by washing the crude product with water, or by freeze drying the product after purification.

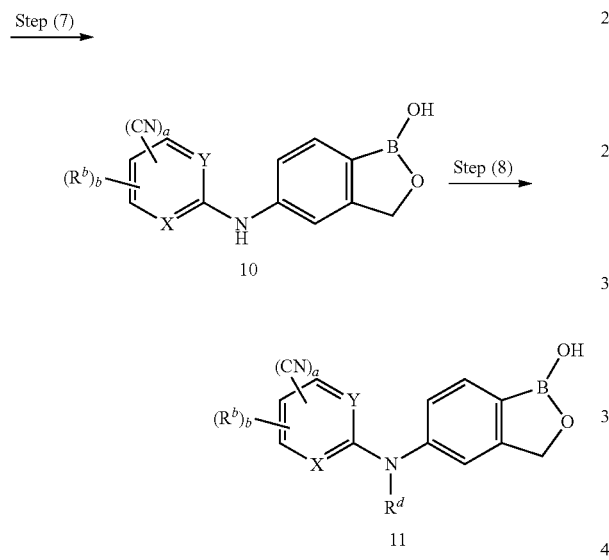

Step 7: The acyl group of compound 9 is removed to give compound 10 by either a base or an acid. In a case of acid, trifluoroacetic acid, hydrochloric acid, hydrobromic acid, and sulfuric acid are used with or without a solvent. In a case of base, sodium hydroxide, potassium hydroxide, sodium carbonate, and potassium carbonate are used in a solvent. The solvent is typically chosen from dichloromethane, methanol, ethanol, 2-propanol, tetrahydrofuran, 1,2-dimethoxyethane, 1,4-dioxane, and the like. The reaction is carried out at about 0° C. to reflux, and complete in from about 1 to about 24 hours.

Step 8: The 5-N position of compound 10 is alkylated with various alkyl halides in the presence of a base to give compound 11. As for the alkyl halides, iodomethane, iodoethane, iodopropane, iodobutane, iodopentane, iodohexane, iodocyclopropane, iodocyclobutane, iodocyclopentane, iodocyclohexane, and the like are used from 1 to 10 equivalents. The base is typically chosen from sodium hydride, potassium tert-butoxide, sodium carbonate, potassium carbonate, sodium hydroxide, potassium hydroxide, and the like. The solvent is typically chosen from tetrahydrofuran, 1,4-dioxane, N,N-dimethylformamide, 1,2-dimethoxyethane, toluene, and the like. The reaction is carried out at about 0° C. to room temperature for from about 1 to about 24 hours.

Strategy B is described below for the alternative production of 5-N-substituted derivatives:
Strategy B:

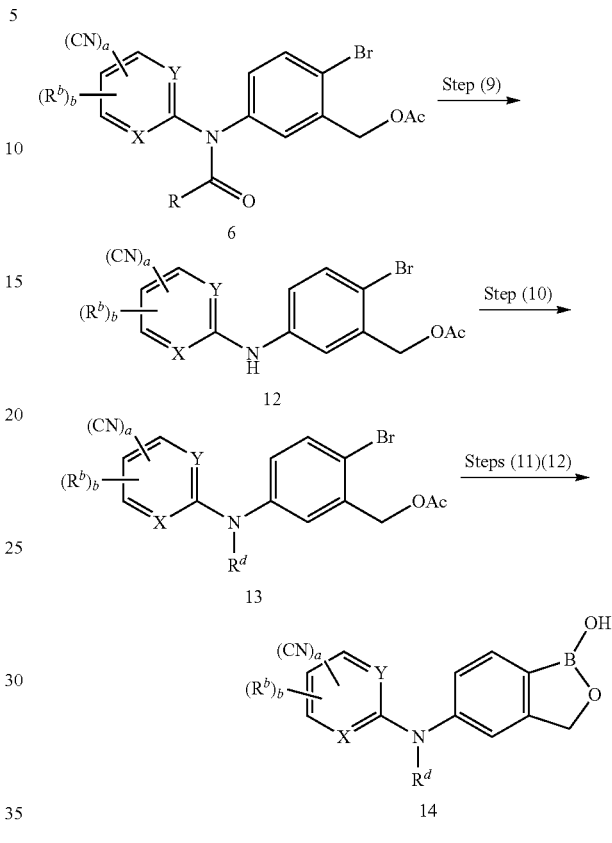

Step 9: The reaction conditions are the same as those described in Step 7.

Step 10: The reaction conditions are the same as those described in Step 8.

Step 11: The reaction conditions are the same as those described in Step 5.

Step 12: The reaction conditions are the same as those described in Step 6.

The compounds of the invention can be converted into hydrates and solvates by methods similar to those described herein.

III.f) Combinations Comprising Additional Therapeutic Agents

The compounds of the invention may also be used in combination with additional therapeutic agents. The invention thus provides, in a further aspect, a combination comprising a compound described herein or a pharmaceutically acceptable salt thereof together with at least one additional therapeutic agent. In an exemplary embodiment, the additional therapeutic agent is a compound of the invention. In an exemplary embodiment, the additional therapeutic agent includes a boron atom. In an exemplary embodiment, the additional therapeutic agent does not contain a boron atom. In an exemplary embodiment, the additional therapeutic agent is a compound described in sections III a)-e).

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. In an exemplary embodiment, the additional therapeutic agent is an antiinflammatory. In an exemplary embodiment, the additional therapeutic agent is a steroid or cyclosporine or psoralen or UVA or retinoid or methotrexete or vitamin $D_3$ analog. In an exemplary embodiment, the steroid is a systemic steroid or a topical steroid. In an exemplary embodiment, the additional therapeutic agent is topical steroid or antihistamine or calcineurin inhibitor. In an exemplary embodiment, the additional therapeutic agent is CC-10004 or AWD-12-281. In an exemplary embodiment, the additional therapeutic agent is a corticosteroid or a NSAIDs. In an exemplary embodiment, the additional therapeutic agent is a PDE4 inhibitor. In an exemplary embodiment, the additional therapeutic agent is rolipram or roflumilast.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the patient ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

IV. The Methods a) Decreasing the Production of a Cytokine and/or Chemokine

In another aspect, the invention provides a method for decreasing the production of a cytokine and/or a chemokine, the method comprising: contacting a cell with a compound of the invention, wherein production of the cytokine and/or chemokine by the cell is decreased. In another aspect, the invention provides a method for decreasing the production of a cytokine and/or a chemokine, the method comprising: contacting a cell with a compound described herein or a pharmaceutically acceptable salt thereof, wherein production of the cytokine and/or chemokine by the cell is decreased. In an exemplary embodiment, the compound of the invention is a compound described herein, or a pharmaceutically acceptable salt thereof. In an exemplary embodiment, the compound of the invention is a compound described herein. In an exemplary embodiment, the cell is contacted with a therapeutically effective amount of the compound. In an exemplary embodiment, the compound is according to a formula described herein. In an exemplary embodiment, the compound is selected from the group consisting of C1, C2, C3, C4 and C5.

In an exemplary embodiment, the method is for decreasing the production of a cytokine, which is a TH1 cytokine. In an exemplary embodiment, the TH1 cytokine is IFN-γ or IL-2.

In an exemplary embodiment, the method is for decreasing the production of a cytokine, which is a TH2 cytokine. In an exemplary embodiment, the TH2 cytokine is selected from the group consisting of IL-4, IL-5 and IL-10. In an exemplary embodiment, the cytokine is IL-4. In an exemplary embodiment, the cytokine is IL-5. In an exemplary embodiment, the cytokine is IL-10.

In an exemplary embodiment, the method is for decreasing the production of a cytokine, which is selected from the group consisting of IL-1α, IL-1β, IL-2, IL-3, IL-6, IL-7, IL-9, IL-12, IL-17, IL-18, IL-23, TNF-α, LT, LIF, Oncostatin, IFNα, IFNβ and IFN-γ. In another exemplary embodiment, the cytokine is selected from the group consisting of IL-1β, IL-2, IL-3, IL-6, IL-7, IL-9, IL-12, IL-23, TNF-α, LT, LIF, Oncostatin, and IFN-γ. In another exemplary embodiment, the cytokine is selected from the group consisting of IL-1β, IL-2, IL-23, TNF-α and IFN-γ. In another exemplary embodiment, the cytokine is TNF-α. In another exemplary embodiment, the cytokine is IL-23. In another exemplary embodiment, the cytokine is IL-2.

In an exemplary embodiment, the method is for decreasing the release of a cytokine, which is selected from the group consisting of IL-1β, IL-2, IL-4, IL-5, IL-6, IL-8, IL-10, IL-12, IL-23, TNF-α and IFN-γ.

In an exemplary embodiment, the method is for decreasing the production of a cytokine, which is selected from the group consisting of IL-4, IL-10, IL-11, W-13 and TGF-β.

In an exemplary embodiment, the method is for decreasing the production of a chemokine, which is selected from the group consisting of IL-8, Gro-α, MIP-1, MCP-1, PGE2, ENA-78, and RANTES. In an exemplary embodiment, the chemokine is selected from the group consisting of MCP-1 and PGE2.

In an exemplary embodiment, for any of the methods described herein, the compound of the invention is present in an amount which will inhibit the production of a cytokine and/or a chemokine by at least about 5 to about 100%, or at least about 30 to about 100%, 40 to about 100%, or at least about 50 to about 100%, or at least about 60 to about 100%, or at least about 70 to about 100%, or at least about 80 to about 100%, or at least about 90 to about 100%, or at least about 30 to about 70%, or at least about 40 to about 90%, or at least about 45 to about 80%, or at least about 55 to about 75%, or at least about 75 to about 98%, or at least about 55 to about 99%, or at least about 5% to about 20% or at least about 10% to about 25%. In an exemplary embodiment, the compound of the invention is a compound described herein.

b) Increasing the Production of a Cytokine and/or a Chemokine

In another aspect, the invention provides a method for increasing the production of a cytokine and/or a chemokine, the method comprising: contacting a cell with a compound of the invention, wherein production of the cytokine and/or chemokine by the cell is increased. In an exemplary embodiment, the compound is described herein or a pharmaceutically acceptable salt thereof. In an exemplary embodiment, the compound of the invention is a compound described herein. In an exemplary embodiment, the cell is contacted with a therapeutically effective amount of the compound. In an exemplary embodiment, the compound is according to a formula described herein. In an exemplary embodiment, the compound is selected from the group consisting of C1, C2, C3, C4 and C5.

In an exemplary embodiment, the method is for increasing the production of a cytokine, which is a TH1 cytokine. In an exemplary embodiment, the TH1 cytokine is IFN-γ or IL-2.

In an exemplary embodiment, the method is for increasing the production of a cytokine, which is a TH2 cytokine. In an exemplary embodiment, the TH2 cytokine is selected from the group consisting of IL-4, IL-5 and IL-10.

In an exemplary embodiment, the method is for increasing the production of a cytokine, which is selected from the group consisting of IL-4, IL-10, IL-11, W-13 and TGF-β.

In an exemplary embodiment, the method is for increasing the production of a chemokine, which is selected from the group consisting of IL-8, Gro-α, MIP-1, MCP-1, PGE2, ENA-78 and RANTES. In an exemplary embodiment, the chemokine is MCP-1 or PGE2.

In an exemplary embodiment, for any of the methods described herein, the compound of the invention is present in an amount which will increase the production of a cytokine and/or a chemokine by at least about 5 to about 100%, or at least about 30 to about 100%, 40 to about 100%, or at least about 50 to about 100%, or at least about 60 to about 100%, or at least about 70 to about 100%, or at least about 80 to about 100%, or at least about 90 to about 100%, or at least about 30 to about 70%, or at least about 40 to about 90%, or at least about 45 to about 80%, or at least about 55 to about 75%, or at least about 75 to about 98%, or at least about 55 to about 99%, or at least about 5% to about 20% or at least about 10% to about 25%. In an exemplary embodiment, the compound of the invention is a compound described herein.

c) Decreasing the Release of a Cytokine and/or Chemokine

In another aspect, the invention provides a method for decreasing the release of a cytokine and/or a chemokine, the method comprising: contacting a cell with a compound of the invention, wherein the release of the cytokine and/or chemokine by the cell is decreased. In an exemplary embodiment, the compound of the invention is a compound described herein or a pharmaceutically acceptable salt thereof. The compound of the invention is a compound described herein. In an exemplary embodiment, the cell is contacted with a therapeutically effective amount of the compound. In an exemplary embodiment, the compound is according to a formula described herein. In an exemplary embodiment, the compound is selected from the group consisting of C1, C2, C3, C4 and C5.

In an exemplary embodiment, the method is for decreasing the release of a cytokine, which is a TH1 cytokine. In an exemplary embodiment, the TH1 cytokine is IFN-γ or IL-2.

In an exemplary embodiment, the method is for decreasing the release of a cytokine, which is a TH2 cytokine. In an exemplary embodiment, the TH2 cytokine is selected from the group consisting of IL-4, IL-5 and IL-10.

In an exemplary embodiment, the method is for decreasing the release of a cytokine, which is selected from the group consisting of IL-1α, IL-1β, IL-2, IL-3, IL-6, IL-7, IL-9, IL-12, IL-17, IL-18, IL-23, TNF-α, LT, LIF, Oncostatin, IFNα, IFNβ and IFN-γ. In another exemplary embodiment, the cytokine is selected from the group consisting of IL-1β, IL-2, IL-3, IL-6, IL-7, IL-9, IL-12, IL-23, TNF-α, LT, LIF, Oncostatin, and IFN-γ. In another exemplary embodiment, the cytokine is selected from the group consisting of IL-1β, IL-2, IL-23, TNF-α and IFN-γ. In another exemplary embodiment, the cytokine is TNF-α.

In an exemplary embodiment, the method is for decreasing the release of a cytokine, which is selected from the group consisting of IL-1β, IL-2, IL-4, IL-5, IL-6, IL-8, IL-10, IL-12, IL-23, TNF-α and IFN-γ.

In an exemplary embodiment, the compound of the invention decreases the release of a cytokine which is selected from the group consisting of IL-1β, IL-2, IL-4, IL-5, IL-6, IL-8, IL-10, IL-12, IL-23, TNF-α and IFN-γ.

In an exemplary embodiment, the method is for decreasing the release of a cytokine, which is selected from the group consisting of IL-4, IL-10, IL-11, W-13 and TGF-β.

In an exemplary embodiment, the method is for decreasing the release of a chemokine, which is selected from the group consisting of IL-8, Gro-α, MIP-1, MCP-1, PGE2, ENA-78, and RANTES. In an exemplary embodiment, the chemokine is MCP-1 or PGE2. In an exemplary embodiment, the compound is C17 and the chemokine is MCP-1 or PGE2.

In an exemplary embodiment, the compound of the invention decreases the release of a cytokine which is selected from the group consisting of TNF-α, IL-2, IFNγ, IL-5, and IL-10, and does not substantially decrease the release of IL-1β, IL-6 and IL-8. In an exemplary embodiment, the compound decreases the release of IL-12 or IL-23.

In an exemplary embodiment, for any of the methods described herein, the compound of the invention is present in an amount which will decrease the release of a cytokine and/or a chemokine by at least about 5 to about 100%, or at least about 30 to about 100%, 40 to about 100%, or at least about 50 to about 100%, or at least about 60 to about 100%, or at least about 70 to about 100%, or at least about 80 to about 100%, or at least about 90 to about 100%, or at least about 30 to about 70%, or at least about 40 to about 90%, or at least about 45 to about 80%, or at least about 55 to about 75%, or at least about 75 to about 98%, or at least about 55 to about 99%, or at least about 5% to about 20% or at least about 10% to about 25%. In another exemplary embodiment, the compound of the invention is a compound described herein or a pharmaceutically acceptable salt thereof d) Increasing the Release of a Cytokine and/or a Chemokine In another aspect, the invention provides a method for increasing the production of a cytokine and/or a chemokine, the method comprising: contacting a cell with a compound of the invention, wherein release of the cytokine and/or chemokine by the cell is increased. In an exemplary embodiment, the compound of the invention is a compound described herein or a pharmaceutically acceptable salt thereof. In an exemplary embodiment, the compound is described herein. In an exemplary embodiment, the cell is contacted with a therapeutically effective amount of the compound. In an exemplary embodiment, the compound is according to a formula described herein. In an exemplary embodiment, the compound is selected from the group consisting of C1, C2, C3, C4 and C5.

In an exemplary embodiment, the method is for increasing the release of a cytokine, which is a TH1 cytokine. In an exemplary embodiment, the TH1 cytokine is IFN-γ or IL-2.

In an exemplary embodiment, the method is for increasing the release of a cytokine, which is a TH2 cytokine. In an exemplary embodiment, the TH2 cytokine is selected from the group consisting of IL-4, IL-5 and IL-10.

In an exemplary embodiment, the method is for increasing the release of a cytokine, which is selected from the group consisting of IL-4, IL-10, IL-11, W-13 and TGF-β.

In an exemplary embodiment, the method is for increasing the release of a chemokine, which is selected from the group consisting of IL-8, Gro-α, MIP-1, MCP-1, PGE2, ENA-78, and RANTES. In an exemplary embodiment, the chemokine is MCP-1 or PGE2.

In an exemplary embodiment, for any of the methods described herein, the compound of the invention is present in an amount which will increase release of a cytokine and/or a chemokine by at least about 5 to about 100%, or at least about 30 to about 100%, 40 to about 100%, or at least about 50 to about 100%, or at least about 60 to about 100%, or at least about 70 to about 100%, or at least about 80 to about 100%, or at least about 90 to about 100%, or at least about 30 to about 70%, or at least about 40 to about 90%, or at least about 45 to about 80%, or at least about 55 to about 75%, or at least about 75 to about 98%, or at least about 55 to about 99%, or at least about 5% to about 20% or at least about 10% to about 25%. In an exemplary embodiment, the compound of the invention is a compound described herein or a pharmaceutically acceptable salt thereof e) Inhibiting a Phosphodiesterase In another aspect, the invention provides a method for inhibiting a phosphodiesterase (PDE), the method comprising: contacting the phosphodiesterase with a compound of the invention, wherein the phosphodiesterase is inhibited. In an exemplary embodiment, the compound of the invention is a compound described herein or a pharmaceutically acceptable salt thereof. In an exemplary embodiment, the compound of the invention is a compound described herein. In an exemplary embodiment, the amount of the compound is a therapeutically effective amount. In an exemplary embodiment, the compound is according to a formula described herein. In an exemplary embodiment, the compound is selected from the group consisting of C1, C2, C3, C4 and C5.

In an exemplary embodiment, the phosphodiesterase is selected from the group consisting of PDE1, PDE2, PDE3, PDE4, PDE5, PDE6, PDE7, PDE8, PDE9, PDE10 and PDE11. In an exemplary embodiment, the phosphodiesterase is PDE4.

In an exemplary embodiment, the PDE4 is selected from the group consisting of PDE4A, PDE4B, PDE4C and PDE4D. In an exemplary embodiment, the PDE4 is PDE4B. In an exemplary embodiment, the phosphodiesterase is PDE7.

In an exemplary embodiment, the invention provides a method for inhibiting a phosphodiesterase4 (PDE4), but not significantly inhibiting at least one PDE which is selected from the group consisting of PDE1, PDE2, PDE3, PDE5 and PDE6, involving contacting a cell with a compound of the invention, thereby providing said inhibition.

In another exemplary embodiment, the invention provides a method for inhibiting a phosphodiesterase4 (PDE4), the method comprising: contacting the phosphodiesterase with a compound which is selected from the group consisting of C1, C2, C3, C4 and C5, or a pharmaceutically acceptable salt thereof, wherein the phosphodiesterase4 (PDE4) is inhibited. In another exemplary embodiment, the invention provides a method for inhibiting a phosphodiesterase7 (PDE7), the method comprising: contacting the phosphodiesterase with a compound which is selected from the group consisting of C1, C2, C3, C4 and C5, or a pharmaceutically acceptable salt thereof, wherein the phosphodiesterase7 (PDE7) is inhibited. In another exemplary embodiment, the invention provides a method for inhibiting a phosphodiesterase4 (PDE4), the method comprising: contacting the phosphodiesterase with a compound which is selected from the group consisting of C1, C2, C3, C4 and C5, or a pharmaceutically acceptable salt thereof, wherein the phosphodiesterase4 (PDE4) is inhibited. In another exemplary embodiment, the invention provides a method for inhibiting a phosphodiesterase7 (PDE7), the method comprising: contacting the phosphodiesterase with a compound which is selected from the group consisting of C1, C2, C3, C4 and C5, or a pharmaceutically acceptable salt thereof, wherein the phosphodiesterase7 (PDE7) is inhibited. In an exemplary embodiment, the amount of the compound is a therapeutically effective amount.

In an exemplary embodiment, for any of the methods described herein, the of the invention, or a compound described by a formula presented herein, is present in an amount which will inhibit a phosphodiesterase described herein by at least about 5 to about 100%, or at least about 30 to about 100%, 40 to about 100%, or at least about 50 to about 100%, or at least about 60 to about 100%, or at least about 70 to about 100%, or at least about 80 to about 100%, or at least about 90 to about 100%, or at least about 30 to about 70%, or at least about 40 to about 90%, or at least about 45 to about 80%, or at least about 55 to about 75%, or at least about 75 to about 98%, or at least about 55 to about 99%, or at least about 5% to about 20% or at least about 10% to about 25%. In an exemplary embodiment, the compound of the invention is a compound described herein or a pharmaceutically acceptable salt thereof f) Conditions and Effects In another aspect, the invention provides a method of treating and/or preventing a condition, or enhancing an effect, in an animal, the method comprising administering to the animal an amount of a compound of the invention, thereby treating or preventing the condition. In an exemplary embodiment, the compound of the invention is a compound described herein or a pharmaceutically acceptable salt thereof. In an exemplary embodiment, the compound of the invention is a compound described herein. In an exemplary embodiment, the amount is a therapeutically effective amount. In an exemplary embodiment, the compound is according to a formula described herein. In an exemplary embodiment, the compound is according to a formula described in the section entitled "Inhibiting a phosphodiesterase". In an exemplary embodiment, the compound is selected from the group consisting of C1, C2, C3, C4 and C5.

In an exemplary embodiment, the condition is a disease. In an exemplary embodiment, the condition is an inflammatory-related condition. In an exemplary embodiment, the condition involves the increase of production of a cytokine and/or a chemokine. In an exemplary embodiment, the condition involves the decrease of production of a cytokine and/or a chemokine. In an exemplary embodiment, the condition involves the increase of release of a cytokine and/or a chemokine. In an exemplary embodiment, the condition involves the decrease of release of a cytokine and/or a chemokine. In an exemplary embodiment, the condition involves the inhibition of a phosphodiesterase. In an exemplary embodiment, the compound is in an amount sufficient to treat the inflammatory-related disease by inhibiting pro-inflammatory cytokine expression or by stimulating anti-inflammatory cytokine expression, but the amount is less than sufficient to substantially inhibit cyclin dependent kinases. In an exemplary embodiment, the condition is mediated by a cytokine. In an exemplary embodiment, the condition is mediated by a chemokine In an exemplary embodiment, the condition is mediated by a neutrophil. In an exemplary embodiment, the condition is mediated by a phosphodiesterase. In an exemplary embodiment, the condition is mediated by a phosphodiesterase4. In an exemplary embodiment, the condition is mediated by a phosphodiesterase7.

In an exemplary embodiment, the condition is selected from the group consisting of periodontitis, dry eye disease, rheumatoid arthritis, osteoarthritis, Crohn's disease, ulcerative colitis, psoriatic arthritis, traumatic arthritis, rubella arthritis, inflammatory bowel disease, multiple sclerosis, psoriasis, graft versus host disease, systemic lupus erythematosus, toxic shock syndrome, irritable bowel syndrome, muscle degeneration, allograft rejections, pancreatitis, insulinitis, glomerulonephritis, diabetic nephropathy, renal fibrosis, chronic renal failure, gout, leprosy, acute synovitis, Reiter's syndrome, gouty arthritis, Behcet's disease, spondylitis, endometriosis, non-articular inflammatory conditions, such as intervertebral disk syndrome conditions, bursitis, tendonitis, tenosynovitis or fibromyalgic syndrome; and acute or chronic pain, including but not limited to neurological pain, neuropathies, polyneuropathies, diabetes-related polyneuropathies, trauma, migraine, tension and cluster headache, Horton's disease, varicose ulcers, neuralgias, musculo-skeletal pain, osteo-traumatic pain, fractures, algodystrophy, spondylarthritis, fibromyalgia, phantom limb pain, back pain, vertebral pain, post-surgery pain, herniated intervertebral disc-induced sciatica, cancer-related pain, vascular pain, visceral pain, childbirth, or HIV-related pain. Another cytokine mediated disease is selected from the group consisting of allergy, a metabolic disease, a chemotherapy/radiation related complication; diabetes type I; diabetes type II; a liver disease; a gastrointestinal disorder; an ophthamological disease; allergic conjunctivitis; diabetic retinopathy; Sjogren's syndrome; uveitis; a pulmonary disorder, a renal disease; dermatitis; HIV-related cachexia; cerebral malaria; ankylosing spondolytis; leprosy; anemia; fibromyalgia, kidney failure, stroke, chronic heart failure, endotoxemia, reperfusion injury, ischemia reperfusion, myocardial ischemia, restenosis, thrombosis, angiogenesis, Coronary Heart Disease, Coronary Artery Disease, acute coronary syndrome, Takayasu arteritis, cardiac failure such as heart failure, aortic valve stenosis, cardiomyopathy, myocarditis, vasculitis, vascular restenosis, valvular disease or coronary artery bypass; hypercholesteremia, diseases or conditions related to blood coagulation or fibrinolysis, such as for example, acute venous thrombosis, pulmonary embolism, thrombosis during pregnancy, hemorrhagic skin necrosis, acute or chronic disseminated intravascular coagulation (DIC), clot formation from surgery, long bed rest or long periods of immobilization, venous thrombosis, fulminant meningococcemia, acute thrombotic strokes, acute coronary occlusion, acute peripheral arterial occlusion, massive pulmonary embolism, axillary vein thrombosis, massive iliofemoral vein thrombosis, occluded arterial or venous cannulae, cardiomyopathy, venoocclusive disease of the liver, hypotension, decreased cardiac output, decreased vascular resistance, pulmonary hypertension, diminished lung compliance, leukopenia or thrombocytopenia; and atherosclerosis.

In an exemplary embodiment, the condition is selected from the group consisting of allergic conjunctivitis, uveitis, glaucoma, optic neuritis, retinal ischemia, diabetic retinopathy, laser induced optic damage, surgery-induced proliferative vitreoretinopathy and trauma-induced proliferative vitreoretinopathy.

In an exemplary embodiment, the condition is selected from the group consisting of allergic rhinitis, asthma, adult respiratory distress syndrome, chronic pulmonary inflammation, chronic obstructive pulmonary disease, emphysema, bronchitis, mucus hypersecretion, silicosis, SARS infection and respiratory tract inflammation.

In an exemplary embodiment, the condition is selected from the group consisting of psoriasis, eczema, atopic dermatitis, contact dermatitis, or acne.

In an exemplary embodiment, the condition is selected from the group consisting of Guillain-Barre syndrome, Parkinson's disease, Huntington's disease, Alzheimer's disease, amyotrophic lateral sclerosis, multiple sclerosis and other demyelinating diseases, viral and bacterial meningitis, CNS trauma, spinal cord injury, seizures, convulsions, olivopontocerebellar atrophy, AIDS dementia complex, MERRF and MELAS syndromes, Leber's disease, Wernicke's encephalopathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia, aneurism, and epilepsy.

In an exemplary embodiment, the condition is selected from the group consisting of bone resorption diseases, osteopetrosis, osteoporosis and osteoarthritis.

In an exemplary embodiment, the condition is selected from the group consisting of diabetes, systemic cachexia, cachexia secondary to infection or malignancy, cachexia secondary to acquired immune deficiency syndrome (AIDS), obesity, anorexia and bulimia nervosa. In an exemplary embodiment, the condition is selected from the group consisting of sepsis, HIV, HCV, malaria, infectious arthritis, leishmaniasis, Lyme disease, cancer, including but not limited to breast cancer, colon cancer, lung cancer, prostatic cancer, multiple myeloma, acute myelogenous leukemia, myelodysplastic syndrome, non-Hodgkins lymphoma, follicular lymphoma, Castleman's disease and drug resistance.

In an exemplary embodiment, the condition is selected from the group consisting of bronchial asthma, rhinitis, influenza, stroke, myocardial infarction, thermal injury, adult respiratory distress syndrome (ARDS), multiple organ injury secondary to trauma, acute glomerulonephritis, dermatoses with acute inflammatory components, acute purulent meningitis, hemodialysis, leukopheresis, granulocyte transfusion associated syndromes and necrotizing enterocolitis.

In an exemplary embodiment, the condition is selected from the group consisting of inflammatory bowel disease (IBD), psoriasis, rheumatoid arthritis (RA), multiple sclerosis (MS), neurodegenerative disorder, cardiovascular disease (CVD) and atherosclerosis, and metabolic disease (the metabolic syndrome and diabetes) as well as infection-related inflammation. In an exemplary embodiment, the condition is a neurodegenerative disorder which is selected from the group consisting of Alzheimer's disease and Parkinson disease. In an exemplary embodiment, the condition is inflammatory bowel disease which is selected from the group consisting of: Crohn's disease or ulcerative colitis. In an exemplary embodiment, the condition is a gastrointestinal complication. In an exemplary embodiment, the condition is diarrhea. In an exemplary embodiment, the condition is selected from the group consisting of celiac disease and non-specific colitis. In an exemplary embodiment, the condition is a liver disease. In an exemplary embodiment, the condition is selected from the group consisting of an autoimmune hepatitis, hepatitis C, primary biliary cirrhosis, primary sclerosing cholangitis, or fulminant liver failure. In an exemplary embodiment, the condition is a bone disease. In an exemplary embodiment, the condition is osteoporosis. In an exemplary embodiment, the condition is a pulmonary disorder. In an exemplary embodiment, the condition is selected from the group consisting of allergic rhinitis, asthma, chronic obstructive pulmonary disease, chronic granulomatous inflammation, cystic fibrosis, and sarcoidosis. In an exemplary embodiment, condition is cardiovascular disease. In an exemplary embodiment, the cardiovascular disease is selected from the group consisting of atheroscleotic cardiac disease, congestive heart failure and restenosis. In an exemplary embodiment, the condition is a renal disease. In an exemplary embodiment, the condition is selected from the group consisting of glomerulp-nephritis and vasculitis. In an exemplary embodiment, the condition is selected from the group consisting of post-radio-therapy related disease and atherosclerosis. In yet another embodiment the condition is atopic dermatitis. In yet another embodiment the condition is actinic keratosis.

In an exemplary embodiment, the PDE4 inhibition is treating and/or preventing a disorder, and the disorder is selected from the group consisting of psoriasis, inflammatory arthritis, rheumatoid arthritis, asthma, chronic bronchitis, inflammatory bowel disease (IBD), chronic obstructive pulmonary disease (COPD), atopic dermatitis, urticaria, allergic rhinitis, allergic conjunctivitis, vernal conjunctivitis, colitis, esoniophilic granuloma, septic shock, reperfusion injury of the myocardium, reperfusion injury of the brain, chronic glomerulonephritis, endotoxic shock, adult respiratory distress syndrome, cystic fibrosis, arterial restenosis, artherosclerosis, keratosis, rheumatoid spondylitis, osteoarthritis, pyresis, diabetes mellitus, pneumoconiosis, chronic obstructive airways disease, toxic contact eczema, allergic contact eczema, atopic eczema, seborrheic eczema, lichen simplex, sunburn, pruritus in the anogenital area, alopecia greata, hypertrophic scars, discoid lupus erythematosus, systemic lupus erythematosus, follicular pyodermias, wide-area pyodermias, endogenous acne, exogenous acne, acne rosacea, Behcet's disease, anaphylactoid purpura nephritis, leukemia, multiple sclerosis, gastrointestinal disease and autoimmune disease. In an exemplary embodiment, the colitis is selected from the group consisting of ulcerative colitis, Crohn's colitis, diversion colitis, ischemic colitis, infectious colitis, fulminant colitis, chemical colitis, microscopic colitis, lymphocytic colitis and atypical colitis. In an exemplary embodiment, the colitis is selected from the group consisting of ulcerative colitis and Crohn's colitis.

In an exemplary embodiment, the condition is psoriasis. In an exemplary embodiment, psoriasis is selected from the group consisting of plaque psoriasis, flexural psoriasis (inverse psoriasis), guttate psoriasis, pustular psoriasis, nail psoriasis, psoriatic arthritis and erythrodermic psoriasis. In an exemplary embodiment, the psoriasis is selected from the group consisting of plaque psoriasis and nail psoriasis. In an exemplary embodiment, the condition is psoriasis and the compound which is selected from the group consisting of C1, C2, C3, C4 and C5, or a pharmaceutically acceptable salt thereof. In an exemplary embodiment, the condition is plaque psoriasis or nail psoriasis and the compound is selected from the group consisting of C1, C2, C3, C4 and C5, or a pharmaceutically acceptable salt thereof.

In an exemplary embodiment, the disorder is selected from the group consisting of cognition impairment or decline and memory impairment. In an exemplary embodiment, the memory impairment is due to dementia. In an exemplary embodiment, the patient is suffering from memory impairment due to Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia, an acute neuronal disease, age-related cognitive decline, HIV or a cardiovascular disease.

In an exemplary embodiment, the PDE4 inhibition is enhancing an effect, wherein the enhanced effect is cognition or memory.

In an exemplary embodiment, the invention provides a method for stimulating ovarian follicular growth in a female, comprising administering to a female a medicament comprising a compound of the invention, whereby ovarian follicular growth is stimulated in the female. In an exemplary embodiment, the compound of the invention is a compound described herein or a pharmaceutically acceptable salt thereof. In an exemplary embodiment, the female is undergoing ovulation induction. In an exemplary embodiment, the female is undergoing controlled ovarian hyperstimulation. In an exemplary embodiment, the medicament is administered simultaneously, separately or sequentially with follicle stimulating hormone (FSH), or an agent having FSH activity, or an agent that stimulates endogenous FSH release.

The invention also provides a method of treating an inflammatory-related disease associated with cytokine expression levels, which comprises administering to an animal in need of such treatment the compound of the invention. In an exemplary embodiment, the compound is according to a formula described herein. In an exemplary embodiment, the compound of the invention is a compound described herein or a pharmaceutically acceptable salt thereof.

In an exemplary embodiment, the invention provides a method of treating or preventing an inflammatory-related disease in an animal, the method comprising administering to the animal a therapeutically effective amount of a compound of the invention, wherein the compound is in an amount sufficient to treat the inflammatory-related disease by inhibiting pro-inflammatory cytokine expression or by stimulating anti-inflammatory cytokine expression, but the amount is less than sufficient to substantially inhibit cyclin dependent kinases. In an exemplary embodiment, the compound of the invention is a compound described herein or a pharmaceutically acceptable salt thereof.

In an exemplary embodiment, the invention provides a method for inhibiting the production of an inflammatory cytokine by cells capable of producing the inflammatory cytokine, the method comprises contacting a cell with a therapeutic amount of compound of the invention, wherein production of the inflammatory cytokine by the cells is inhibited. In an exemplary embodiment, the therapeutic amount is sufficient to inhibit the production of the inflammatory cytokine protein between about 50% and about 99%.

In an exemplary embodiment, the invention provides a method for inhibiting an inflammatory response in an animal, the method comprising: contacting the animal with a therapeutic amount of a compound of the invention, wherein the inflammatory response is inhibited.

In an exemplary embodiment, for any of the methods described herein, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, for any of the methods described herein, the animal is selected from the group consisting of a human, cattle, goat, pig, sheep, horse, cow, bull, dog, guinea pig, gerbil, rabbit, cat, chicken and turkey. In another exemplary embodiment, for any of the methods described herein, the animal is a human.

In an exemplary embodiment, for any of the methods described herein, a compound of the invention and/or a pharmaceutical formulation described herein can be used.

In another exemplary embodiment, in any of the methods of treating/preventing a condition or enhancing an effect described herein, the animal being administered the compound of the invention is not otherwise in need of treatment with a compound of the invention.

In another exemplary embodiment, the method involves treating psoriasis by administering a compound of the invention to an animal not otherwise in need of treatment with the compounds of the invention.

In another exemplary embodiment, the method involves treating atopic dermatitis by administering a compound of the invention to an animal not otherwise in need of treatment with the compounds of the invention.

g)

In another aspect, the invention provides a method of inhibiting or activating a receptor, comprising contacting said receptor with a compound described herein, wherein said receptor is selected from the group consisting of epidermal growth factor receptor (EGFR or ErbB-1 or HER1); HM74A (GPR109A); Histamine1; Histamine2; Histamine3; Histamine4; β-adrenergic-receptor kinase (β2AR); $K_{ATP}$ (ATP-sensitive potassium channel); protein kinase C; protein kinase A (PKA or cAMP-dependent protein kinase); PAR1 (F2R); and TLR3 (CD283).

In another aspect, the invention provides method of treating and/or preventing a disease which implicates a receptor, comprising administering to an animal a therapeutically effective amount of a compound described herein, wherein said receptor is selected from the group consisting of epidermal growth factor receptor (EGFR or ErbB-1 or HER1); HM74A (GPR109A); Histamine1; Histamine2; Histamine3; Histamine4; β-adrenergic-receptor kinase (β2AR); $K_{ATP}$ (ATP-sensitive potassium channel); protein kinase C; protein kinase A (PKA or cAMP-dependent protein kinase); PAR1 (F2R); and TLR3 (CD283). In an exemplary embodiment, the disease is caused by the overexpression, underexpression or malfunction of said receptor.

In another aspect, the invention provides a method of inhibiting or activating a downstream target of a receptor, comprising contacting said downstream target with a compound described herein, wherein said receptor is selected from the group consisting of m epidermal growth factor receptor (EGFR or ErbB-1 or HER1); HM74A (GPR109A); Histamine1; Histamine2; Histamine3; Histamine4; β-adrenergic-receptor kinase (β2AR); $K_{ATP}$ (ATP-sensitive potassium channel); protein kinase C; protein kinase A (PKA or cAMP-dependent protein kinase); PAR1 (F2R); and TLR3 (CD283).

In another aspect, the invention provides a method of treating and/or preventing a disease which implicates a downstream target of a receptor, comprising administering to an animal in need of such treatment a therapeutically effective amount of a compound described herein, wherein said receptor is selected from the group consisting of epidermal growth factor receptor (EGFR or ErbB-1 or HER1); HM74A (GPR109A); Histamine1; Histamine2; Histamine3; Histamine4; β-adrenergic-receptor kinase (β2AR); $K_{ATP}$ (ATP-sensitive potassium channel); protein kinase C; protein kinase A (PKA or cAMP-dependent protein kinase); PAR1 (F2R); and TLR3 (CD283). In an exemplary embodiment, the disease is caused by the overexpression, underexpression or malfunction of said receptor. In another exemplary embodiment, the compound is selected from the group consisting of C1, C2, C3, C4 and C5. In another exemplary embodiment, the compound is part of a pharmaceutical formulation described herein which is administered to said animal. In another exemplary embodiment, the animal is a human. In another exemplary embodiment, there is a proviso that the animal is not otherwise in need of treatment with a compound of the invention.

V. Pharmaceutical Formulations

In another aspect, the invention provides a pharmaceutical formulation comprising: (a) a compound of the invention and (b) a pharmaceutically acceptable excipient. In an exemplary embodiment, the compound of the invention is a compound described herein or a pharmaceutically acceptable salt thereof. In an exemplary embodiment, the compound of the invention is a compound described herein or a pharmaceutically acceptable salt thereof. In an exemplary embodiment, the compound is according to a formula described herein. In an exemplary embodiment, the compound is selected from the group consisting of C1, C2, C3, C4 and C5. In an exemplary embodiment, the formulation is a unit dosage form. In an exemplary embodiment, the formulation is an oral unit dosage form or a topical unit dosage form. In an exemplary embodiment, the topical unit dosage form is selected from the group consisting of a lotion, an ointment and a cream. In an exemplary embodiment, the formulation is for topical use. In an exemplary embodiment, the pharmaceutical formulations described herein can be used in a method described herein As described in detail herein, the pharmaceutical compositions of the present invention may be specially formulated for administration in solid or liquid form, including those adapted for oral administration, e.g., tablets, drenches (aqueous or non-aqueous solutions or suspensions), parenteral administration (including intravenous and intramuscular), or epidural injection as, for example, a sterile solution or suspension, or sustained release formulation. The pharmaceutical compositions of the present invention may also be specifically formulated for administration transdermally.

The pharmaceutical compositions of the invention may be administered orally, parenterally, subcutaneously, transdermally, nasally, or by anal suppository. The pharmaceutical compositions of the invention may also be administered using controlled delivery devices.

Formulations of the present invention include those suitable for oral and parenteral administration, particularly intramuscular, intravenous and subcutaneous administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect, without being toxic to the patient. Generally, out of one hundred percent, this amount will range from about 1 percent to about ninety-nine percent of active ingredient.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, caplets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a compound of the present invention as an active ingredient. A compound of the present invention may also be administered as a bolus, electuary or paste.

In solid dosage forms of the invention for oral administration (capsules, tablets, caplets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue. Pharmaceutical compositions or unit dosage forms of the present invention in the form of prolonged-action tablets may comprise compressed tablets formulated to release the drug substance in a manner to provide medication over a period of time. There are a number of tablet types that include delayed-action tablets in which the release of the drug substance is prevented for an interval of time after administration or until certain physiological conditions exist. Repeat action tablets may be formed that periodically release a complete dose of the drug substance to the gastrointestinal fluids. Also, extended release tablets that continuously release increments of the contained drug substance to the gastrointestinal fluids may be formed.

Compounds of the invention can be also administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the compounds of this invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Compounds of the present invention may also be formulated as transdermal, topical, and mucosal dosage forms, which forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers can be used to assist in delivering the active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

When the compounds of the present invention are administered as pharmaceuticals, to humans and animals, they can be given per se or as a pharmaceutical composition containing, for example, 0.1 to 99.5% of active ingredient in combination with a pharmaceutically acceptable carrier.

The preparations of the present invention may be given orally and parenterally. They are of course given in forms suitable for each administration route. For example, they are administered in tablets or capsule form, by injection, and by intravenous administration. In one embodiment, oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.005 mg per kilogram to about 5 mg per kilogram of body weight per day.

The terms "treatment" or "treating" is intended to encompass therapy, preventing (prophylaxis), preventing relapse, and amelioration of acute symptoms. Note that "treating" refers to either or both of the amelioration of symptoms and the resolution of the underlying condition. In many of the conditions of the invention, the administration of a compound or composition of the invention may act not directly on the disease state, but rather on some pernicious symptom, and the improvement of that symptom leads to a general and desirable amelioration of the disease state The patient receiving this treatment is any animal in need, including primates, in particular humans, and other mammals such as equines, cattle, swine and sheep; and poultry and pets in general.

The compounds and pharmaceutical compositions of the invention can be administered in conjunction with other pharmaceutical agents, for instance antimicrobial agents, such as penicillins, cephalosporins, aminoglycosides and glycopeptides. Conjunctive therapy thus includes sequential, simultaneous and separate administration of the active compound in a way that the therapeutic effects of the first administered agent have not entirely disappeared when the subsequent agent is administered.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention.

Exemplary embodiments are summarized herein below.

In an exemplary embodiment, the invention is a compound having a structure according to the following formula:

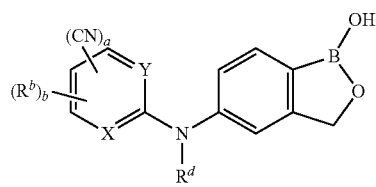

wherein X is selected from the group consisting of CH, C(CN), CR$^b$ and N; Y is selected from the group consisting of CH, C(CN), CR$^b$ and N; a is 0 or 1; b is 0 or 1; R$^d$ is selected from the group consisting of H, unsubstituted $C_1$-$C_6$ alkyl, COR$^{10}$, and —C(O)OR$^{10}$, wherein R$^{10}$ is H or unsubstituted $C_1$-$C_6$ alkyl; with the proviso that when X or Y is C(CN), then a is 0; with the proviso that when X or Y is CR$^b$, then b is 0; with the proviso that X and Y cannot both be C(CN); with the proviso that X and Y cannot both be CR$^b$; R$^b$ is selected from the group consisting of OR$^4$, NR$^4$R$^5$, SR$^4$, —S(O)R$^4$, —S(O)$_2$R$^4$, —S(O)$_2$NR$^4$R$^5$, —C(O)R$^4$, —C(O)OR$^4$, —C(O)NR$^4$R$^5$, nitro, cyano, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein R$^4$ and R$^5$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, with the proviso that that R$^4$ and R$^5$, together with the atoms to which they are attached, are optionally combined to form a 5- to 7-membered substituted or unsubstituted heterocycloalkyl ring, or a salt thereof.

In an exemplary embodiment, according to the above paragraph, the compound has a structure which is:

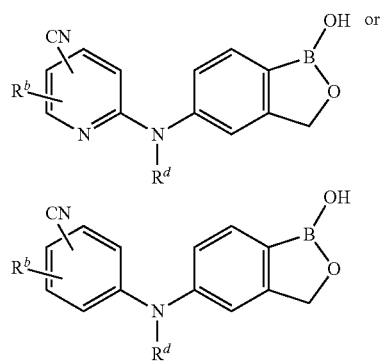

wherein R$^b$ and R$^d$ are as described herein.

In an exemplary embodiment, according to the above paragraph, the compound has a structure which is:

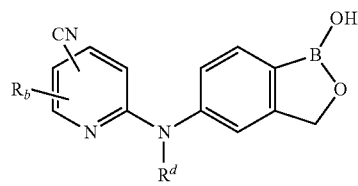

wherein R$^b$ and R$^d$ are as described herein.

In an exemplary embodiment, according to the above paragraph, the compound has a structure which is:

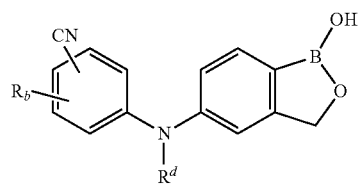

wherein R$^b$ and R$^d$ are as described herein.

In an exemplary embodiment, according to any of the above paragraphs, the compound has a structure which is:

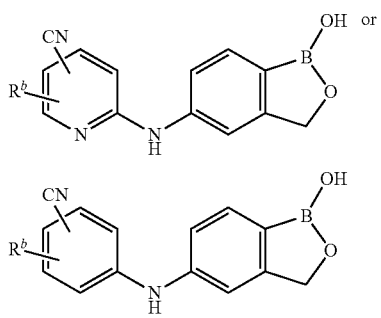

wherein $R^b$ is as described herein.

In an exemplary embodiment, according to any of the above paragraphs, the compound has a structure which is:

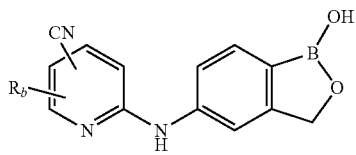

wherein $R^b$ is as described herein.

In an exemplary embodiment, according to any of the above paragraphs, the compound has a structure which is:

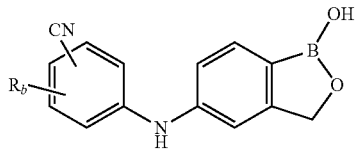

wherein $R^b$ is as described herein.

In an exemplary embodiment, according to any of the above paragraphs, the compound has a structure which is:

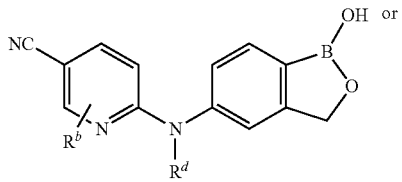

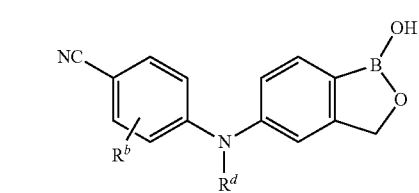

wherein $R^b$ and $R^d$ are as described herein.

In an exemplary embodiment, according to any of the above paragraphs, the compound has a structure which is:

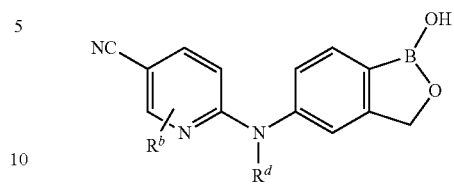

wherein $R^b$ and $R^d$ are as described herein.

In an exemplary embodiment, according to any of the above paragraphs, the compound has a structure which is:

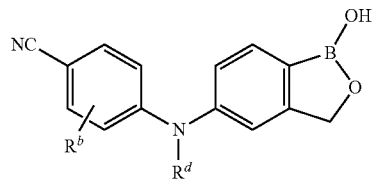

wherein $R^b$ and $R^d$ are as described herein.

In an exemplary embodiment, according to any of the above paragraphs, the compound has a structure which is

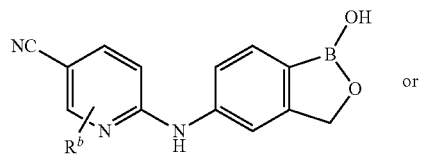

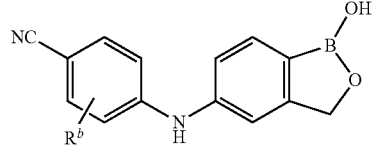

wherein $R^b$ is as described herein.

In an exemplary embodiment, according to any of the above paragraphs, the compound has a structure which is

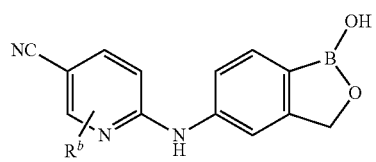

wherein $R^b$ is as described herein.

In an exemplary embodiment, according to any of the above paragraphs, the compound has a structure which is

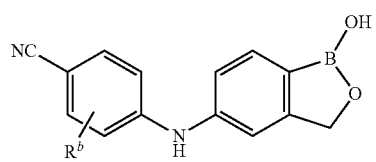

wherein $R^b$ is as described herein.

In an exemplary embodiment, according to any of the above paragraphs, the compound has a structure which is:

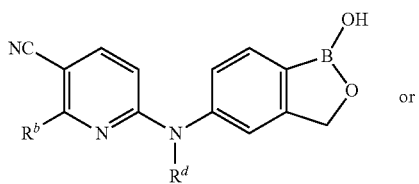

or

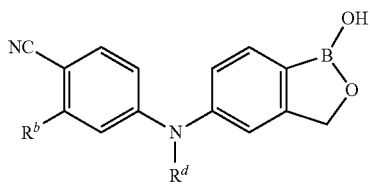

wherein $R^b$ and $R^d$ are as described herein.

In an exemplary embodiment, according to any of the above paragraphs, the compound has a structure which is:

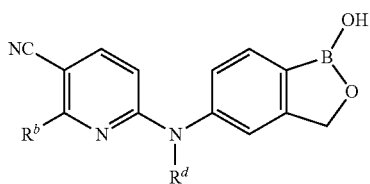

wherein $R^b$ and $R^d$ are as described herein.

In an exemplary embodiment, according to any of the above paragraphs, the compound has a structure which is:

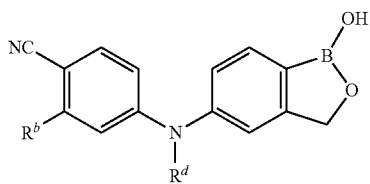

wherein $R^b$ and $R^d$ are as described herein.

In an exemplary embodiment, according to any of the above paragraphs, the compound has a structure which is:

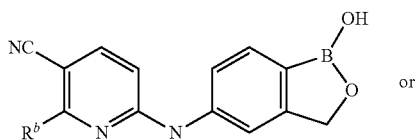

or

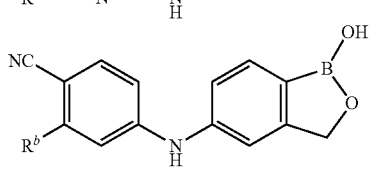

wherein $R^b$ is as described herein.

In an exemplary embodiment, according to any of the above paragraphs, the compound has a structure which is:

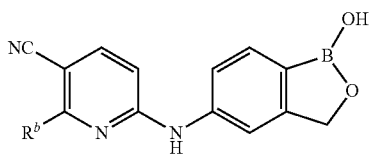

wherein $R^b$ is as described herein.

In an exemplary embodiment, according to any of the above paragraphs, the compound has a structure which is:

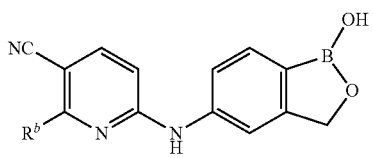

wherein $R^b$ is as described herein.

In an exemplary embodiment, according to any of the above paragraphs, $R^b$ is $OR^4$, and $R^4$ is selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, $R^b$ is $OR^4$, and $R^4$ is substituted or unsubstituted alkyl.

In an exemplary embodiment, according to any of the above paragraphs, the compound has a structure which is selected from the group consisting of:

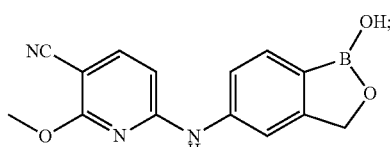

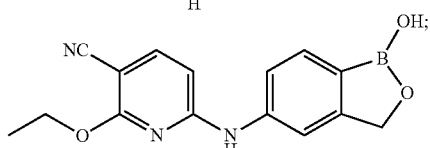

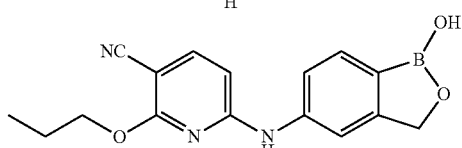

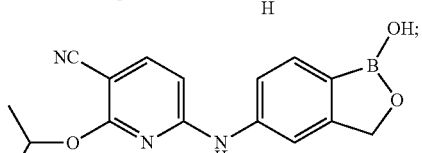

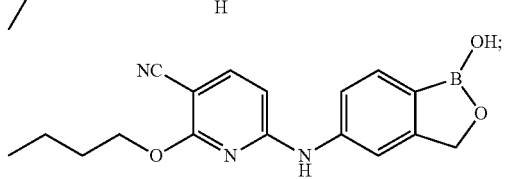

-continued

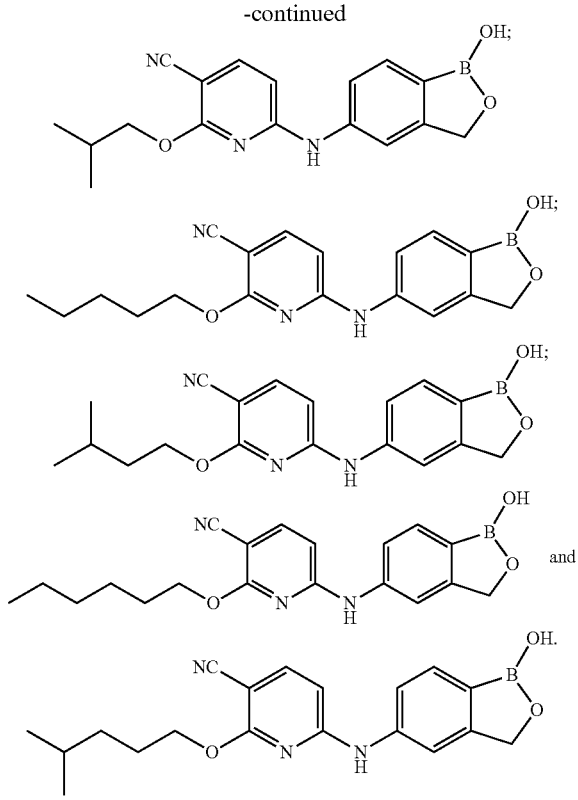

In an exemplary embodiment, according to any of the above paragraphs, $R^b$ is $OR^4$, and $R^4$ is cycloalkylsubstituted alkyl.

In an exemplary embodiment, according to any of the above paragraphs, $R^b$ is $OR^4$, and $R^4$ is cycloalkylsubstituted methyl.

In an exemplary embodiment, according to any of the above paragraphs, the compound has a structure which is selected from the group consisting of:

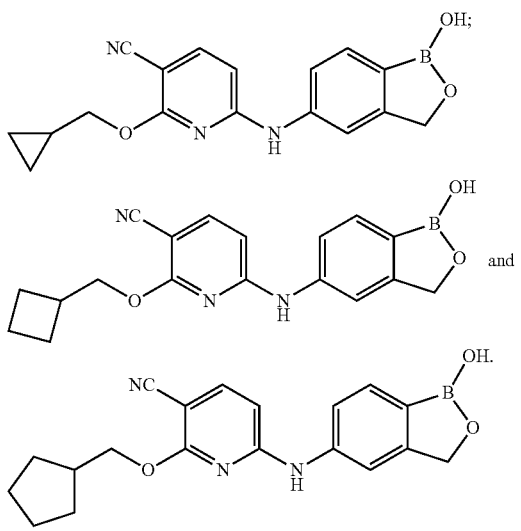

In an exemplary embodiment, according to any of the above paragraphs, $R^b$ is $OR^4$, and $R^4$ is substituted or unsubstituted heteroalkyl.

In an exemplary embodiment, according to any of the above paragraphs, the compound has a structure which is selected from the group consisting of:

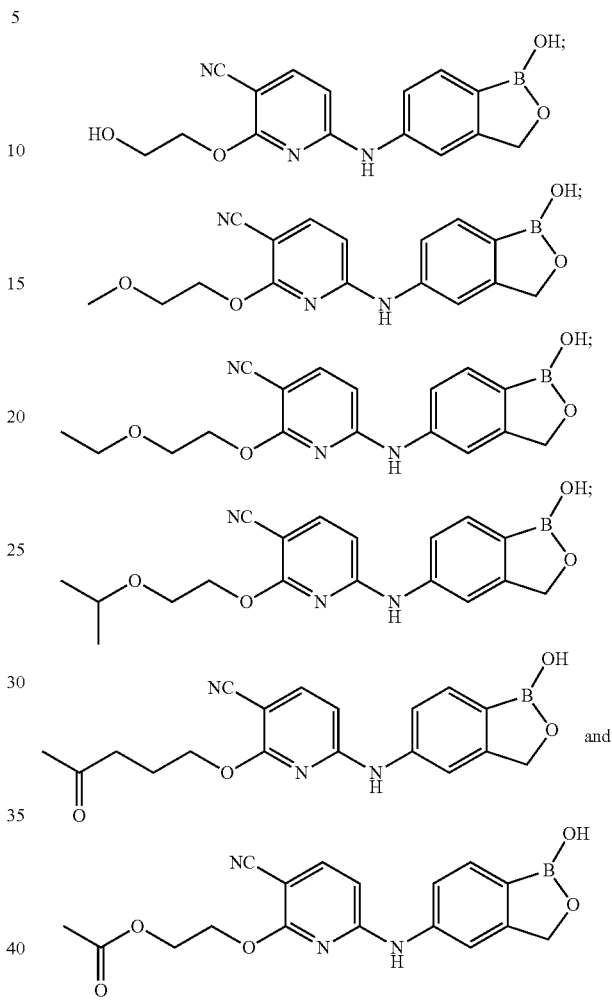

In an exemplary embodiment, according to any of the above paragraphs, $R^b$ is $NR^4R^5$, and $R^4$ and $R^5$ are each independently selected from the group consisting from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, $R^b$ is $NHR^5$, and $R^5$ is selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, $R^b$ is $NHR^5$, and $R^5$ is substituted or unsubstituted alkyl.

In an exemplary embodiment, according to any of the above paragraphs, $R^b$ is $NHR^5$, and $R^5$ is hydroxysubstituted alkyl.

In an exemplary embodiment, according to any of the above paragraphs, $R^b$ is $NHR^5$, and $R^5$ is hydroxyethyl.

In an exemplary embodiment, according to any of the above paragraphs, $R^b$ is $NHR^5$, and $R^5$ is alkoxysubstituted alkyl.

In an exemplary embodiment, according to any of the above paragraphs, $R^b$ is $NHR^5$, and $R^5$ is alkoxyethyl.

In an exemplary embodiment, according to any of the above paragraphs, $R^b$ is $NHR^5$, and $R^5$ is methoxysubstituted alkyl.

In an exemplary embodiment, according to any of the above paragraphs, $R^b$ is $NHR^5$, and $R^5$ is substituted or unsubstituted heteroalkyl.

In an exemplary embodiment, according to any of the above paragraphs, the compound has a structure which is selected from the group consisting of:

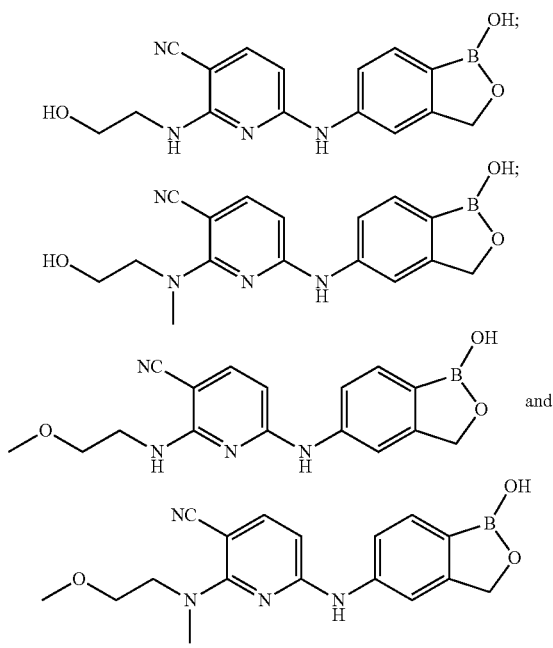

and

In an exemplary embodiment, the invention provides a pharmaceutical formulation comprising: a) the compound according to any of the above paragraphs, or a salt thereof; and b) a pharmaceutically acceptable excipient.

In an exemplary embodiment, according to the above paragraph, the pharmaceutical formulation is a unit dosage form.

In an exemplary embodiment, according to any of the above paragraphs, the salt of the compound in the pharmaceutical formulation is a pharmaceutically acceptable salt.

In an exemplary embodiment, according to any of the above paragraphs, the pharmaceutical formulation is for oral or topical use.

In an exemplary embodiment, the invention provides a method of decreasing the release of a cytokine or a chemokine, the method comprising: contacting a cell with the compound of the invention, wherein the release of the cytokine or chemokine by the cell is decreased.

In an exemplary embodiment, according to any of the above paragraphs, the compound has a structure described herein.

In an exemplary embodiment, according to any of the above paragraphs, the cytokine is selected from the group consisting of IL-1α, IL-1β, IL-2, IL-3, IL-6, IL-7, IL-9, IL-12, IL-17, IL-18, IL-23, TNF-α, LT, LIF, Oncostatin, IFNα, IFNβ and IFN-γ.

In an exemplary embodiment, according to any of the above paragraphs, the cytokine is selected from the group consisting of IL-1β, IL-2, IL-4, IL-5, IL-6, IL-8, IL-10, IL-12, IL-23, TNF-α and IFN-γ.

In an exemplary embodiment, according to any of the above paragraphs, the cytokine is selected from the group consisting of IL-2, IL-5, IL-10, IL-12, IL-23, TNF-α and IFN-γ.

In an exemplary embodiment, according to any of the above paragraphs, the chemokine is selected from the group consisting of IL-8, Gro-α, MIP-1, MCP-1, PGE2, ENA-78, and RANTES.

In an exemplary embodiment, the invention provides a method of treating a condition in an animal, the method comprising administering to the animal a therapeutically effective amount of the compound of the invention, thereby treating the condition.

In an exemplary embodiment, according to any of the above paragraphs, the compound has a structure described herein.

In an exemplary embodiment, the condition is selected from the group consisting of arthritis, rheumatoid arthritis, an inflammatory bowel disease, psoriasis, a pulmonary disease, multiple sclerosis, a neurodegenerative disorder, congestive heart failure, stroke, aortic valve stenosis, kidney failure, lupus, pancreatitis, allergy, fibrosis, anemia, atherosclerosis, a metabolic disease, a bone disease, a cardiovascular disease, a chemotherapy/radiation related complication, diabetes type I, diabetes type II, a liver disease, a gastrointestinal disorder, an ophthamological disease, allergic conjunctivitis, diabetic retinopathy, Sjogren's syndrome, uveitis, a pulmonary disorder, a renal disease, dermatitis, HIV-related cachexia, cerebral malaria, ankylosing spondolytis, leprosy, anemia and fibromyalgia.

In an exemplary embodiment, the condition is selected from the group consisting of psoriasis, atopic dermatitis, rheumatoid arthritis, an inflammatory bowel disease, asthma and chronic obstructive pulmonary disease.

In an exemplary embodiment, the condition is psoriasis, said psoriasis is selected from the group consisting of plaque psoriasis, flexural psoriasis, Guttate psoriasis, pustular psoriasis, nail psoriasis and erythrodermic psoriasis.

In an exemplary embodiment, the psoriasis is selected from the group consisting of plaque psoriasis and nail psoriasis.

In an exemplary embodiment, the invention provides a method of inhibiting a phosphodiesterase (PDE), the method comprising: contacting the phosphodiesterase with a compound of the invention, thereby inhibiting the phosphodiesterase.

In an exemplary embodiment, the phosphodiesterase is selected from the group consisting of phosphodiesterase4 (PDE4) and phosphodiesterase7 (PDE7).

In an exemplary embodiment, according to any of the above paragraphs, the invention is a use of a compound of the invention in the manufacture of a medicament for the treatment and/or prophylaxis of protozoal infection.

In an exemplary embodiment, according to any of the above paragraphs, the invention is a use of a combination of the invention in the manufacture of a medicament for the treatment and/or prophylaxis of protozoal infection.

The invention is further illustrated by the Examples that follow. The Examples are not intended to define or limit the scope of the invention.

EXAMPLES

Proton NMR are recorded on Varian Mercury 300 (300 MHz) or 400-MR (400 MHz) spectrometer and chemical shifts are reported as δ (ppm) down field from tetramethylsilane. Mass spectra are determined on Agilent 1200 and 6120 LC/MS system. The mass spectrometer was equipped with an electrospray ion source (ES) operated in a positive or negative mode.

All solvents used were commercially available and were used without further purification. Reactions were typically run using anhydrous solvents under an inert atmosphere of nitrogen.

Compounds are named using ChemDraw Ultra 11.0, or using their catalogue name if commercially available.

Thin layer chromatography (TLC) was performed on Alugram (Silica gel 60 $F_{254}$) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), vanillin (generated by dissolving about 1 g vanillin in 100 mL 10% $H_2SO_4$), ninhydrin (available commercially from Aldrich), or Magic Stain (generated by thoroughly mixing 25 g $(NH_4)_6Mo_7O_{24}\cdot 4H_2O$, 5 g $(NH_4)_2Ce(IV)(NO_3)_6$ in 450 mL water and 50 mL concentrated $H_2SO_4$) to visualize the compound. Flash chromatography was preformed using typically 40-63 μm (230-400 mesh) silica gel from Silicycle following analogous techniques to those disclosed in Still, W. C.; Kahn, M.; and Mitra, M. Journal of Organic Chemistry, 1978, 43, 2923-2925. Typical solvents used for flash chromatography or thin layer chromatography were mixtures of chloroform/methanol, dichloromethane/methanol, ethyl acetate/methanol and hexanes/ethyl acetate. Reverse phase column chromatography were performed on a Biotage® using a Biotage $C_{18}$ cartridges and a water/methanol gradient (typically eluting from 5% MeOH/$H_2O$ to 90% MeOH/$H_2O$).

Preparative liquid chromatography was performed on Agilent 1200 series system. The column used was a SunFire Prep C18, 5 μm, 30×50 mm. Narrow gradients with acetonitrile/water, with the water containing either 0.1% trifluoroacetic acid or 0.1% acetic acid, were used to elute the compound at a flow rate of approximately 20 mL/min and a total run time between 20-30 min.

Example 1

C1. 5-[N-tert-Butoxycarbonyl-(4-cyanophenylamino)]-1,3-dihydro-1-hydroxybenzoxaborole

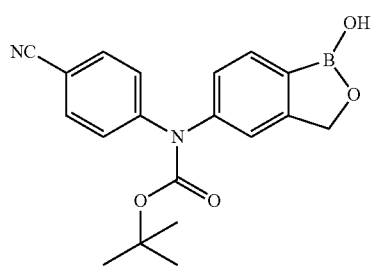 [SMILES: CC(C)(C)OC(=O)N(c1ccc(C#N)cc1)c1ccc2c(c1)COB2O]

To a mixture of 4-fluorobenzonitrile (12.61 g, 104 mmol) and 4-bromo-3-methylaniline (15.36 g, 82.56 mmol) in N,N-dimethylformamide (160 mL) on an ice water bath under a nitrogen balloon was added potassium tert-butyloxide (18.53 g, 165.12 mmol) portionwise. The reaction was stirred at room temperature overnight. Then water was added, and the mixture was extracted with ethyl acetate. The organic layer was washed with water, brine and dried on anhydrous sodium sulfate. The solvent was removed under reduced pressure to get crude product. The crude was then recrystallized from ethyl acetate to give 4-(4-bromo-3-methylphenylamino)benzonitrile (5.675 g, 24%).

To a solution of 4-(4-bromo-3-methylphenylamino)benzonitrile (5.35 g, 18.63 mmol) in tetrahydrofuran (200 mL) was added di-tert-butyl dicarbonate (6.1 g, 27.95 mmol) followed by 4-N,N-dimethylaminopyridine (2.28 g, 18.63 mmol). The reaction mixture was stirred at room temperature for 30 minutes. Then most of the solvent was removed under reduced pressure. Water was added and the mixture was extracted with ethyl acetate. The organic layer was washed with water, brine and dried on anhydrous sodium sulfate. The solvent was removed under reduced pressure, and the residue was purified by silica gel column (9:1 hexane/ethyl acetate) to give tert-butyl N-(4-bromo-3-methylphenyl)-N-(4-cyanophenyl)carbamate (6.79 g, 94%).

A mixture of tert-butyl N-(4-bromo-3-methylphenyl)-N-(4-cyanophenyl)carbamate (6.18 g, 15.9 mmol), N-bromosuccinimide (2.84 g, 15.96 mmol) and 2,2-azobisisobutyronitrile (0.13 g, 0.798 mmol) in carbon tetrachloride (160 mL) was stirred under nitrogen atmosphere at 95° C. overnight. Then more N-bromosuccinimide (0.566 g, 3.18 mmol) and 2,2-azobisisobutyronitrile was added and the reaction was stirred under nitrogen atmosphere at 95° C. overnight. The reaction mixture was then washed with water, brine, dried over anhydrous sodium sulfate, filtered and evaporated under reduced pressure. The residue was purified by silica gel column (9:1 hexane/ethyl acetate) to give tert-butyl N-[4-bromo-3-(bromomethyl)phenyl]-N-(4-cyanophenyl)carbamate.

A mixture of tert-butyl tert-butyl N-[4-bromo-3-(bromomethyl)phenyl]-N-(4-cyanophenyl)carbamate (8.68 g, 18.62 mmol) and sodium acetate (7.64 g, 93.1 mmol) in N,N-dimethylformamide was stirred at 50° C. overnight. Then water was added and the mixture was extracted with ethyl acetate. The organic layer was washed with water, brine and dried on anhydrous sodium sulfate. The solvent was removed under reduced pressure to give crude product. The crude was purified by silica gel column (8:2 to 7:3 hexane/ethyl acetate) to give 2-bromo-5-[N-tert-butoxycarbonyl-(4-cyanophenyl)amino]benzyl acetate (3.93 g, 47%).

A mixture of 2-bromo-5-[N-tert-butoxycarbonyl-(4-cyanophenyl)amino]benzyl acetate (2.93 g, 6.58 mmol), bis(pinacolato)diboron (1.84 g, 7.24 mmol), [1,1'-bis(diphenylphosphino)ferrocene]dichloropalladium(II) (0.16 g, 0.197 mmol) and potassium acetate (1.94 g, 19.74 mmol) in 1,4-dioxane (120 mL) was purged with nitrogen for 15 minutes and then stirred under nitrogen atmosphere at 80° C. overnight.

The mixture was filtered through a Celite pad, and the solvent was removed under reduced pressure. Silica gel column (8:2 hexane/ethyl acetate) gave 5-[N-tert-butoxycarbonyl(4-cyanophenyl)amino]-2-(4,4,5,5-tetramethyl-1,3,2-dioxaborolan-2-yl)benzyl acetate (3.334 g, quantitative).

To a solution of 5-[N-tert-butoxycarbonyl(4-cyanophenyl)amino]-2-(4,4,5,5-tetramethyl-1,3,2-dioxaborolan-2-yl)benzyl acetate (3.334 g, 6.77 mmol) in methanol (68 mL) was added 1M sodium hydroxide solution (20.3 mL, 20.3 mmol). The mixture was stirred at room temperature overnight and then neutralized with 1 mol/L hydrochloric acid until pH=6 to 7. This was then extracted with ethyl acetate. The organic layer was washed with boric acid (0.5 mol/L solution in water) and brine, and dried on anhydrous sodium sulfate. The solvent was removed under reduced pressure, and the residue was purified by silica gel column (8:2 hexane/ethyl acetate) to give 5-[N-tert-Butoxycarbonyl-(4-cyanophenylamino)]-1,3-dihydro-1-hydroxybenzoxaborole (1.43 g, 60%). ES(−)MS m/e=349 (M−1). $^1$H NMR (300 MHz, DMSO-d$^6$) δ ppm 1.37 (s, 9H) 4.94 (s, 2H) 7.18 (d, J=7.6 Hz, 1H) 7.25 (s, 1H) 7.34 (d, J=8.2 Hz, 2H) 7.72 (d, J=7.9 Hz, 1H) 7.80 (d, J=8.5 Hz, 2H) 9.22 (s, 1H).

C2. 5-(4-Cyanophenylamino)-1,3-dihydro-1-hydroxybenzoxaborole

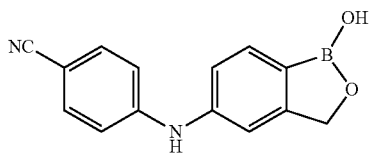 [SMILES: N#Cc1ccc(Nc2ccc3c(c2)COB3O)cc1]

tert-butyl 5-[N-tert-Butoxycarbonyl-(4-cyanophenylamino)]-1,3-dihydro-1-hydroxybenzoxaborole (1.43 g, 4.08 mmol) was treated with 4 mol/L hydrogen chloride in dioxane (60 mL) at room temperature overnight. The mixture was then neutralized with 1 mol/L sodium hydroxide to PH=6 to 7, and extracted with ethyl acetate. The organic layer was washed with brine, dried over anhydrous sodium sulfate. The solvent was removed under reduced pressure, and the residue was purified by silica gel column (3:7 hexane/ethyl acetate) and preparative HPLC to give 5-(4-Cyanophenylamino)-1,3-dihydro-1-hydroxybenzoxaborole. ES(−)MS m/e=249 (M−1). $^1$H NMR (300 MHz, DMSO-d$_6$) δ ppm 4.9 (s, 2H) 7.2 (m, 4H) 7.6 (m, 3H) 9.0 (s, 1H) 9.1 (s, 1H)

C3. 5-[N-(4-Cyanophenyl)-N-methylamino]-1,3-dihydro-1-hydroxybenzoxaborole

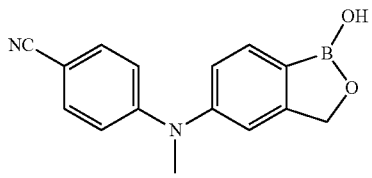 [SMILES: CN(c1ccc(C#N)cc1)c1ccc2c(c1)COB2O]

2-bromo-5-[N-(tert-butoxycarbonyl)-4-cyanophenylamino]benzyl acetate (3.02 g, 6.78 mmol) was treated with 4 mol/L hydrogen chloride in dioxane (20 mL) at room temperature for two hours. This was neutralized with 1 mol/L sodium hydroxide to PH=6 to 7 in ice-water bath and then extracted with ethyl acetate. The organic layer was washed with brine, dried over anhydrous sodium sulfate. The solvent was removed under reduced pressure to give 2-bromo-5-(4-cyanophenylamino)benzyl acetate, which was used for the next step without purification.

To a solution of 2-bromo-5-(4-cyanophenylamino)benzyl acetate (1.0 g, 2.9 mmol) in N,N-dimethylformamide (11 mL) under nitrogen atmosphere was added iodomethane (0.543 mL, 8.7 mmol), and the mixture was stirred in ice-water bath for five minutes. Then sodium hydride (0.174 g, 4.35 mmol) was added, and the reaction was stirred at room temperature for 24 hours. Water was added, and the mixture was extracted with ethyl acetate. The organic layer was washed with brine and dried on anhydrous sodium sulfate. The solvent was removed under reduced pressure to give crude 2-bromo-5-[N-(4-cyanophenyl)-N-methylamino]benzyl acetate.

A mixture of 2-bromo-5-[N-(4-cyanophenyl)-N-methylamino]benzyl acetate (0.597 g, 1.66 mmol), bis(pinacolato)diboron (0.464 g, 1.83 mmol), [1,1'-bis(diphenylphosphino)ferrocene]dichloropalladium(II) (0.041 g, 0.05 mmol) and potassium acetate (0.489 g, 4.98 mmol) in 1,4-dioxane (6.7 mL) was purged with nitrogen for 15 minutes and then stirred under nitrogen atmosphere at 80° C. overnight.

The mixture was filtered through a Celite pad, and the solvent was removed under reduced pressure. Silica gel column (7:3 hexane/ethyl acetate) gave 5-[N-(4-cyanophenyl)-N-methylamino)-2-(4,4,5,5-tetramethyl-1,3,2-dioxaborolan-2-yl)benzyl acetate (0.733 g, quantitative).

To a solution of 5-[N-(4-cyanophenyl)-N-methylamino)-2-(4,4,5,5-tetramethyl-1,3,2-dioxaborolan-2-yl)benzyl acetate (0.7134 g, 1.76 mmol) in methanol (17 mL) was added 1M sodium hydroxide solution (5.28 mL, 5.28 mmol). The mixture was stirred at room temperature overnight and then neutralized with 1 mol/L hydrochloric acid until pH=6 to 7. This was then extracted with ethyl acetate. The organic layer was washed with brine, dried over anhydrous sodium sulfate. The solvent was removed under reduced pressure, and the residue was purified by reversed-phase HPLC to get 5-[N-(4-Cyanophenyl)-N-methylamino]-1,3-dihydro-1-hydroxybenzoxaborole. ES(−)MS m/e=263 (M−1). $^1$H NMR (300 MHz, DMSO-d$_6$) δ ppm 3.33 (s, 3H) 4.96 (s, 2H) 6.87 (d, J=7.9 Hz, 2H) 7.19 (d, J=7.9 Hz, 1H) 7.28 (s, 1H) 7.56 (d, J=7.9 Hz, 2H) 7.74 (d, J=8.2 Hz, 1H) 9.18 (s, 1H).

C4. tert-Butyl 5-cyano-6-methoxypyridin-2-yl(1-hydroxy-1,3-dihydrobenzo[c][1,2]oxaborol-5-yl)carbamate

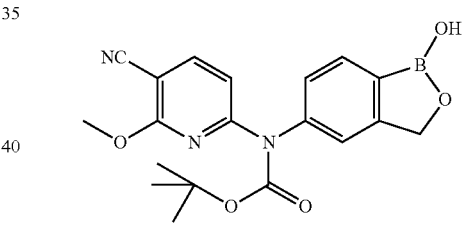

To a solution of 4-bromo-3-methylaniline (5 g, 26.88 mmol) in N,N-dimethylformamide (50 mL) were added di-tert-butyl dicarbonate (11.73 g, 53.75 mmol) and triethylamine (7.5 mL, 53.75 mmol). The reaction was stirred at room temperature for three days. Water (100 mL) was added and product precipitated out of solution, which was filtered and dried under reduced pressure. Precipitates were washed by adding hexanes and sonicated for 5 minutes. The solid was filtered to give tert-butyl 4-bromo-3-methylphenylcarbamate (3.863 g, 50%). $^1$H NMR (400 MHz, DMSO-d$_6$) δ ppm 1.42 (s, 9H), 2.23 (s, 3H), 7.16 (dd, J=2.4, 8.6 Hz, 1H), 7.38 (d, J=8.6 Hz, 1H), 7.43 (s, 1H), 9.41 (s, 1H).

To a solution of tert-butyl 4-bromo-3-methylphenylcarbamate (4.36 g, 15.24 mmol) in N,N-dimethylformamide (60 mL) on an ice bath under a nitrogen balloon was added sodium hydride (0.610 g, 15.24 mmol). The reaction was stirred on an ice-water bath for 10 min. The ice bath was removed and to the solution was added a solution of 6-chloro-2-methoxynicotinonitrile (3.85 g, 22.86 mmol) in N,N-dimethylformamide (40 mL) dropwise. After addition completed, the mixture was stirred overnight at 50° C. Water was added and the mixture was extracted with ethyl acetate. The organic layer was washed with water and brine, and dried on anhydrous sodium sulfate. The solvent was removed under reduced pressure to obtain the crude product. The crude was then purified by silica gel column (100% hexanes to 8:2 hexanes/ethyl acetate) to give tert-butyl 4-bromo-3-methylphenyl(5-cyano-6-methoxypyridin-2-yl)carbamate (3.15 g, 49%). $^1$H NMR (400 MHz, DMSO-$d_6$) δ ppm 1.37 (s, 9H), 2.30 (s, 3H), 3.55 (s, 3H), 7.00 (dd, J=2.6, 8.4 Hz, 1H), 7.22 (d, J=2.5 Hz, 1H), 7.40 (d, J=8.5 Hz, 1H), 7.58 (d, J=8.4 Hz, 1H), 8.17 (d, J=8.4 Hz, 1H), 8.30 (d, J=8.0 Hz, 1H).

To a solution of tert-butyl 4-bromo-3-methylphenyl(5-cyano-6-methoxypyridin-2-yl)carbamate (2.85 g, 6.81 mmol) in carbon tetrachloride (50 mL) was added N-bromosuccinimide (0.909 g, 5.11 mmol) and azobisisobutyronitrile (0.042 g, 0.26 mmol). The mixture was refluxed under nitrogen at 95° C. for two hours. The reaction was cooled to room temperature, water was added and the mixture was extracted with dichloromethane. The organic layer was washed with water and brine, and dried on anhydrous sodium sulfate. The solvent was removed under reduced pressure to give crude tert-butyl 4-bromo-3-(bromomethyl)phenyl(5-cyano-6-methoxypyridin-2-yl)carbamate (4.12 g). The product was used in the next step without further purification.

To a solution of tert-butyl 4-bromo-3-(bromomethyl)phenyl(5-cyano-6-methoxypyridin-2-yl)carbamate (4.46 g, 8.98 mmol) in N,N-dimethylformamide (60 mL) was added sodium acetate (3.68 g, 44.9 mmol). The reaction was stirred at 50° C. for two hours. The mixture was cooled to room temperature and extracted with ethyl acetate and water in portions. The organic layer of each portion was washed three times with water and brine, and dried over sodium sulfate, and filtered. The portions were combined and the solvent was removed under reduced pressure. The residue was purified by Combiflash to give 2-bromo-5-(tert-butoxycarbonyl(5-cyano-6-methoxypyridin-2-yl)amino)benzyl acetate (1.99 g, 2 steps 46%).

To a solution of 2-bromo-5-(tert-butoxycarbonyl(5-cyano-6-methoxypyridin-2-yl)amino)benzyl acetate (1.99 g, 4.18 mmol) in 1,4-dioxane (17 mL) was added potassium acetate (1.23 g, 12.54 mmol), bis(pinacolato)diboron (1.17 g, 4.60 mmol), and 1,1'-Bis(diphenylphosphino)ferrocene]dichloropalladium(II) (0.102 g, 0.125 mmol). The mixture was stirred under nitrogen at 80° C. for five hours. The reaction was cooled to room temperature, filtered through a Celite pad, and the solvent was removed under reduced pressure. The residue was purified by Combiflash to give 5-(tert-butoxycarbonyl(5-cyano-6-methoxypyridin-2-yl)amino)-2-(4,4,5,5-tetramethyl-1,3,2-dioxaborolan-2-yl)benzyl acetate (2.20 g, 91%).

To a solution of 5-(tert-butoxycarbonyl(5-cyano-6-methoxypyridin-2-yl)amino)-2-(4,4,5,5-tetramethyl-1,3,2-dioxaborolan-2-yl)benzyl acetate (2.20 g, 3.82 mmol) in methanol (38 mL) was added 1 mol/L sodium hydroxide (11.5 mL, 11.5 mmol). The reaction was stirred at room temperature for three hours and was then neutralized with 1 mol/L hydrochloric acid until pH=6 to 7. The solvent was removed under reduced pressure and the mixture was extracted with ethyl acetate and the organic layer was washed with an aqueous boric acid solution (0.5 M) five times. The organic layer was washed with brine, dried over anhydrous sodium sulfate, and filtered. The solvent was removed under reduced pressure. The residue was purified by column using Combiflash to give tert-butyl 5-cyano-6-methoxypyridin-2-yl(1-hydroxy-1,3-dihydrobenzo[c][1,2]oxaborol-5-yl)carbamate (1.302 g, 89%). $^1$H NMR (400 MHz, DMSO-$d_6$) δ ppm 1.36 (s, 9H), 3.50 (s, 2H), 4.94 (s, 2H), 7.14 (dd, J=1.8, 7.8 Hz, 1H), 7.22 (s, 1H), 7.38 (d, J=8.4 Hz, 1H), 7.71 (d, J=7.8 Hz, 1H), 8.17 (d, J=8.4 Hz, 1H), 9.19 (s, 1H).

C5. 6-(1-hydroxy-1,3-dihydrobenzo[c][1,2]oxaborol-5-ylamino)-2-methoxynicotinonitrile

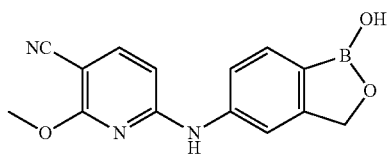 [SMILES: COc1nc(Nc2ccc3c(c2)COB3O)ccc1C#N]

A solution of tert-butyl 5-cyano-6-methoxypyridin-2-yl(1-hydroxy-1,3-dihydrobenzo[c][1,2]oxaborol-5-yl)carbamate (0.944 g, 2.48 mmol) in 4 mol/L hydrogen chloride in dioxane (20 mL) was stirred at room temperature for three hours. The solution was then neutralized with 6 mol/L sodium hydroxide until pH=6 to 7. Water was added and the solution was extracted with ethyl acetate. The organic layer was washed with water, brine, dried over anhydrous sodium sulfate, and filtered. The solvent was removed under reduced pressure. The aqueous layer contained precipitate, which was collected by filtration and dried under reduced pressure. The residue was purified by Combiflash to give 6-(1-hydroxy-1,3-dihydrobenzo[c][1,2]oxaborol-5-ylamino)-2-methoxynicotinonitrile (0.086 g, 9.1%). $^1$H NMR (400 MHz, DMSO-$d_6$) δ ppm 4.95 (s, 2H), 6.50 (d, J=8.4 Hz, 1H), 7.52 (d, J=1.4 Hz, 1H), 7.64 (d, J=8.1 Hz, 1H), 7.83 (d, J=8.4 Hz, 1H), 9.00 (s, 1H), 9.94 (s, 1H).

Example 2

In Vitro Assays

The ability of the compounds described herein to inhibit pro-inflammatory cytokines or phosophodiesterases were tested.

Cytokine Assay

Frozen human peripheral blood mononucleocytes (PBMC) were thawed and centrifuged. Cryopreservation media was aspirated off of the cell pellet, and the cells were resuspended in fresh culture media (CM) comprising RPMI 1640 and 10% FBS in 96 well plates. Test article was dissolved in DMSO to form a 10 mM sample (DMSO, 100%). The 10 mM samples were diluted to 100 μM in CM (DMSO, 1%), then further diluted to 10, 1, 0.1, 0.01 μM in 200 μL of CM (n=3). Inducer (1 μg/mL) LPS for TNF-α or 20 ug/mL PHA for IFNγ, IL-2, IL-4, IL-5 and IL-10. IL-23 was induced with 100 ng/ml IFN-g+1 mg/ml LPS, using THP-1 cells. Vehicle (1% DMSO) was used as a control for this experiment. Vehicle without inducer was used as a negative control. Cells were incubated at 37° C., 5% $CO_2$. Supernatants were extracted at 24 hours (for TNF-α, IL-2 and IFNγ) and 48 hours (for IL-4, IL-5, IL-10 and IL-23), and stored at −20° C. Supernatants were thawed and assayed for cytokine expression using the fluorochrome-labeled cytokine-specific beads and a BD FACSArray™. IL-23 was assayed using a commercial ELISA kit (R&D Systems).

IC50 Results (μM):
TNF-α: (C1): 1.10; (C2): 1.08; (C3): 1.30; (C4): 0.36; (C5): 0.26
IL-23: (C2): 7.35; (C4): 5.77; (C5): 2.74
IL-2: (C1): 0.96; (C2): 0.13; (C3): 0.88; (C4): 0.22; (C5): 0.21
IL-γ: (C1): 0.62; (C2): 1.51; (C3): 2.00; (C4): 0.37; (C5): 0.30

IL-4: (C1): >10; (C2): >10; (C3): >10; (C4): 33; (C5): 23
IL-5: (C1): 2.42; (C2): 6.83; (C3): 3.50; (C4): 0.4; (C5): 0.70
IL-10: (C1): 5.59; (C2): >10; (C3): 3.10; (C4): 6.0; (C5): 3.7

Cytokine Assay

Frozen human peripheral blood mononucleocytes (PBMC) can be thawed and centrifuged. Cryopreservation media can be aspirated off of the cell pellet, and the cells can be resuspended in fresh culture media (CM) comprising RPMI 1640 and 10% FBS in 96 well plates. Test article can be dissolved in DMSO to form a 10 mM sample (DMSO, 100%). The 10 mM samples can be diluted to 100 µM in CM (DMSO, 1%), then further diluted to 10, 1, 0.1, 0.01 µM in 200 µL of CM (n=3). Inducer (1 µg/mL) LPS for a cytokine such as IL-1β or IL-6. Vehicle (1% DMSO) can be used as a control for this experiment. Vehicle without inducer can be used as a negative control. Cells can be incubated at 37° C., 5% $CO_2$. Supernatants can be extracted at 24 hours (for IL-1β or IL-6), and stored at –20° C. Supernatants can be thawed and assayed for cytokine expression using the fluorochrome-labeled cytokine-specific beads and a BD FACSArray™.

PDE Isoform Profiling

Recombinant human PDE enzymes were expressed in a baculoviral system. The assay is a modification of the 2-step method of Thompson & Appleman (Biochem. 10:311-316, 1971), which was adapted for 96-well plate format. Stock solutions were prepared at 40 mM in 100% DMSO. Final [DMSO] was 5%. Each compound was tested by performing 1 in 4 serial dilutions at starting concentration of 100 mM. Each concentration was tested in duplicate. IC50s were generated from 11-point curves and analyzed using Prism software (GraphPad Inc.). PDE isoforms tested include PDE1A3 (cAMP), PDE1A3 (cGMP), PDE2A3, PDE3Cat, PDE4Cat, PDE4A4, PDE4B2, PDE4C2, PDE4D3, PDE5Cat, PDE6AB, PDE7A1, PDE8A1, PDE9A1, PDE10A1 (cAMP), PDE10A1 (cGMP), PDE11A1 (cAMP) and PDE11A1 (cGMP).

PDE4 Assay

PDE4 partially purified from human U-937 myeloid leukemia cells was used. Test article and/or vehicle was incubated with 0.2 mg enzyme and 1 mM cAMP containing 0.01 mM [3H]cAMP in Tris buffer pH 7.5 for 20 minutes at 25° C. The reaction was terminated by boiling for 2 minutes and the resulting AMP is converted to adenosine by addition of 10 mg/ml snake venom nucleotidase and further incubation at 37° C. for 10 minutes. Unhydrolyzed cAMP is bound to AG1-X2 resin, and remaining [3H]Adenosine in the aqueous phase is quantitated by scintillation counting. Test articles were tested at 10, 3, 1, 0.3, 0.1, 0.03, 0.01, 0.003, and 0.001 µM for $IC_{50}$ determination.

IC50 Results (µM):
PDE4: (C1): 2.75; (C2): 0.414; (C3): 0.387; (C4): 0.180; (C5): 0.34

Example 3

In Vivo Assays

1. In Vivo Anti-Inflammation Activity in Phorbol Ester Induced Mouse Ear Edema Model Phorbol 12-myristate 13-acetate (PMA, 5 µg in 20 µL of acetone) can be applied topically to the anterior and posterior surfaces of the right ear to eight groups of CD-1 (Crl.) derived male mice of 5 each (weighing 22±2 g). Test substances and vehicle (acetone:ethanol/1:1, 20 µL/ear) can be each applied to both ears topically 30 minutes before and 15 minutes after PMA challenge. Dexamethasone (1 mg/ear×2) can be used as the positive control and can be administered topically to test animals using the same application schedule. Ear swelling can be then measured by a Dyer model micrometer gauge at 6 hours after PMA application as an index of inflammation. Percent inhibition can be calculated according to the formula: [(Ic−It)/Ic]×100%, where Ic and It refer to increase of ear thickness (mm) in control and treated mice, respectively. Percent inhibition of 30 percent or more in ear swelling can be considered significant anti-inflammatory activity.

2. In Vivo Anti-Inflammation Activity in Oxazolone Induced Mouse Ear Edema Model Groups of 5 BALB/c male mice weighing 23±2 g can be used. The preshaved abdomens of test animals can be sensitized by application of 100 µL of 1.5% oxazolone solution dissolved in acetone. Seven days after the initial sensitization, test substances, as well as vehicle (acetone:ethanol/1:1, 20 µL/ear) can be each administered topically to the anterior and posterior surfaces of the right ear 30 minutes before, and 15 minutes after, challenge by a second application of oxazolone (1% in acetone, 20 ml/ear) via topical route. As a positive control, indomethacin (0.3 mg/ear×2) can be administered topically using the same treatment regime as for the test compounds. Twenty-four hours after the second application of oxazolone, the ear thickness of each mouse can be measured with a Dyer model micrometer gauge. A 30 percent or more inhibition in ear swelling relative to the vehicle control can be considered significant and indicated possible anti-inflammatory activity.

Example 4

As stated hereinbefore the compounds of the invention possess biological activity against a variety of receptors and downstream targets of those receptors. These properties may be assessed, for example, using one or more of the procedures set out below:

EGFR Testing (a) An In Vitro Assay which Determines the Ability of a Test Compound to Inhibit EGFR Kinase.

The ability of compounds to inhibit receptor kinase (EGFR) activity can be assayed using HTScan™ EGF Receptor Kinase Assay Kits (Cell Signaling Technologies, Danvers, Mass.). EGFR tyrosine kinase can be obtained as GST-kinase fusion protein which can be produced using a baculovirus expression system with a construct expressing human EGFR (His672-Ala1210) (GenBank Accession No. NM-005228) with an amino-terminal GST tag. The protein can be purified by one-step affinity chromatography using glutathione-agarose. An anti-phosphotyrosine monoclonal antibody, P-Tyr-100, can be used to detect phosphorylation of biotinylated substrate peptides (EGFR, Biotin-PTP1B (Tyr66). Enzymatic activity can be tested in 60 mM HEPES, 5 mM $MgCl_2$ 5 mM $MnCl_2$ 200 µM ATP, 1.25 mM DTT, 3 µM $Na_3VO_4$, 1.5 mM peptide, and 50 ng EGF Recpetor Kinase. Bound antibody can be detected using the DELFIA system (PerkinElmer, Wellesley, Mass.) consisting of DELFIA™. Europium-labeled Anti-mouse IgG (PerkinElmer, #AD0124), DELFIA™. Enhancement Solution (PerkinElmer, #1244-105), and a DELFIA™. Streptavidin coated, 96-well Plate (PerkinElmer, AAAND-0005). Fluorescence can be measured on a WALLAC Victor 2 plate reader and reported as relative fluorescence units (RFU). Data can be plotted using GraphPad Prism (v4.0a) and IC50s calculated using a sigmoidal dose response curve fitting algorithm.

Test compounds can be dissolved in dimethylsulphoxide (DMSO) to give a 20 mM working stock concentration. Each assay can be setup as follows: Added 100 µl of 10 mM ATP to 1.25 ml 6 mM substrate peptide. Diluted the mixture with dH₂O to 2.5 ml to make 2×ATP/substrate cocktail ([ATP]=400 mM, [substrate]=3 mM). Immediately transfer enzyme from −80° C. to ice. Allowed enzyme to thaw on ice. Microcentrifuged briefly at 4° C. to bring liquid to the bottom of the vial. Returned immediately to ice. Added 10 µl of DTT (1.25 mM) to 2.5 ml of 4×HTScan™ Tyrosine Kinase Buffer (240 mM HEPES pH 7.5, 20 mM MgCl₂, 20 mM MnCl, 12 mM NaVO₃) to make DTT/Kinase buffer. Transfer 1.25 ml of DTT/Kinase buffer to enzyme tube to make 4× reaction cocktail ([enzyme]=4 ng/µL in 4× reaction cocktail). Incubated 12.5 µl of the 4× reaction cocktail with 12.5 µl/well of prediluted compound of interest (usually around 10 µM) for 5 minutes at room temperature. Added 25 µA of 2×ATP/substrate cocktail to 25 µl/well preincubated reaction cocktail/compound. Incubated reaction plate at room temperature for 30 minutes. Added 50 µl/well Stop Buffer (50 mM EDTA, pH 8) to stop the reaction. Transferred 25 µl of each reaction and 75 µl dH₂O/well to a 96-well streptavidin-coated plate and incubated at room temperature for 60 minutes. Washed three times with 200 µl/well PBS/T (PBS, 0.05% Tween-20). Diluted primary antibody, Phospho-Tyrosine mAb (P-Tyr-100), 1:1000 in PBS/T with 1% bovine serum albumin (BSA). Added 100 µl/well primary antibody. Incubated at room temperature for 60 minutes. Washed three times with 200 µl/well PBS/T. Diluted Europium labeled anti-mouse IgG 1:500 in PBS/T with 1% BSA. Added 100 µl/well diluted antibody. Incubated at room temperature for 30 minutes. Washed five times with 200 µl/well PBS/T. Added 100 µl/well DELFIA™ Enhancement Solution. Incubated at room temperature for 5 minutes. Detected 615 nm fluorescence emission with appropriate Time-Resolved Plate Reader.

(b) An In Vitro Assay Which Determines the Ability of a Test Compound to Inhibit the EGF-Stimulated EGFR Phosphorylation.

Allowed A431 cell growth in a T75 flask using standard tissue culture procedures until cells reach near confluency (about 1.5×10⁷) cells; D-MEM, 10% FBS). Under sterile conditions dispensed 100 µl of the cell suspension per well in 96-well microplates (× cells plated per well). Incubated cells and monitor cell density until confluency is achieved with well-to-well consistency; approximately three days. Removed complete media from plate wells by aspiration or manual displacement. Replaced media with 50 µl of pre-warmed serum free media per well and incubated 4 to 16 hours. Made two fold serial dilutions of inhibitor using pre-warmed D-MEM so that the final concentration of inhibitor range from 10 µM to 90 µM. Removed media from A431 cell plate. Added 100 µl of serial diluted inhibitor into cells and incubate 1 to 2 hours. Removed inhibitor from plate wells by aspiration or manual displacement. Added either serum free media for resting cells (mock) or serum free media with 100 ng/ml EGF. Used 100 µl of resting/activation media per well. Allowed incubation at 37° C. for 7.5 minutes. Removed activation or stimulation media manually or by aspiration. Immediately fixed cells with 4% formaldehyde in 1×PBS. Allowed incubation on bench top for 20 minutes at RT with no shaking Washed five times with 1×PBS containing 0.1% Triton X-100 for 5 minutes per Wash. Removed Fixing Solution. Using a multi-channel pipettor, added 200 µl of Triton Washing Solution (1×PBS+0.1% Triton X-100). Allowed wash to shake on a rotator for 5 minutes at room temperature. Repeated washing steps 4 more times after removing wash manually. Using a multi-channel pipettor, blocked cells/wells by adding 100 µl of LI-COR Odyssey Blocking Buffer to each well. Allowed blocking for 90 minutes at RT with moderate shaking on a rotator. Added the two primary antibodies into a tube containing Odyssey Blocking Buffer. Mixed the primary antibody solution well before addition to wells (Phospho-EGFR Tyr1045, (Rabbit; 1:100 dilution; Cell Signaling Technology, 2237; Total EGFR, Mouse; 1:500 dilution; Biosource International, AHR5062). Removed blocking buffer from the blocking step and added 40 µl of the desired primary antibody or antibodies in Odyssey Blocking Buffer to cover the bottom of each well. Added 100 µl of Odyssey Blocking Buffer only to control wells. Incubated with primary antibody overnight with gentle shaking at RT. Washed the plate five times with 1×PBS+0.1% Tween-20 for 5 minutes at RT with gentle shaking, using a generous amount of buffer. Using a multi-channel pipettor added 200 µl of Tween Washing Solution. Allowed wash to shake on a rotator for 5 minutes at RT. Repeated washing steps 4 more times. Diluted the fluorescently labeled secondary antibody in Odyssey Blocking Buffer (Goat anti-mouse IRDye™ 680 (1:200 dilution; LI-COR Cat.#926-32220) Goat anti-rabbit IRDye™ 800CW (1:800 dilution; LI-COR Cat.#926-32211). Mixed the antibody solutions well and added 40 µl of the secondary antibody solution to each well. Incubated for 60 minutes with gentle shaking at RT. Protected plate from light during incubation. Washed the plate five times with 1×PBS+0.1% Tween-20 for 5 minutes at RT with gentle shaking, using a generous amount of buffer. Using a multi-channel pipettor added 200 µl of Tween Washing Solution. Allowed wash to shake on a rotator for 5 minutes at RT. Repeated washing steps 4 more times. After final wash, removed wash solution completely from wells. Turned the plate upside down and tap or blot gently on paper towels to remove traces of wash buffer. Scanned the plate with detection in both the 700 and 800 channels using the Odyssey Infrared Imaging System (700 nm detection for IRDye™ 680 antibody and 800 nm detection for IRDye™ 800CW antibody). Determined the ratio of total to phosphorylated protein (700/800) using Odyssey software and plot the results in Graphpad Prism (V4.0a). Data can be plotted using GraphPad Prism (v4.0a) and IC50s calculated using a sigmoidal dose response curve fitting algorithm.

(c) An In Vitro Assay which Determines the Ability of a Test Compound to Inhibit HDAC Enzymatic Activity.

HDAC inhibitors can be screened using an HDAC fluorimetric assay kit (AK-500, Biomol, Plymouth Meeting, Pa.). Test compounds can be dissolved in dimethylsulphoxide (DMSO) to give a 20 mM working stock concentration. Fluorescence can be measured on a WALLAC Victor 2 plate reader and reported as relative fluorescence units (RFU). Data can be plotted using GraphPad Prism (v4.0a) and IC50s calculated using a sigmoidal dose response curve fitting algorithm.

Each assay can be setup as follows: Defrosted all kit components and kept on ice until use. Diluted HeLa nuclear extract 1:29 in Assay Buffer (50 mM Tris/Cl, pH 8.0, 137 mM NaCl, 2.7 mM KCl, 1 mM MgCl₂). Prepared dilutions of Trichostatin A (TSA, positive control) and tested compounds in assay buffer (5× of final concentration). Diluted Fluor de Lys™. Substrate in assay buffer to 100 uM (50 fold=2× final). Diluted Fluor de Lys™ developer concentrate 20-fold (e.g. 50 µl plus 950 µl Assay Buffer) in cold assay buffer. Second, diluted the 0.2 mM Trichostatin A 100-fold in the 1× Developer (e.g. 10 µl in 1 ml; final Trichostatin A concentration in the 1× Developer=2 µM; final concentration after addition to HDAC/Substrate reaction=1 µM). Added Assay buffer, diluted trichostatin A or test inhibitor to appropriate wells of the microtiter plate. Added diluted HeLa extract or other HDAC sample to all wells except for negative controls. Allowed diluted Fluor de Lys™ Substrate and the samples in the microtiter plate to equilibrate to assay temperature (e.g. 25 or 37° C.). Initiated HDAC reactions by adding diluted substrate (25 µl) to each well and mixing thoroughly. Allowed HDAC reactions to proceed for 1 hour and then stopped them by addition of Fluor de Lys™ Developer (50 µl). Incubated plate at room temperature (25° C.) for 10-15 min. Read samples in a microtiter-plate reading fluorimeter capable of excitation at a wavelength in the range 350-380 nm and detection of emitted light in the range 440-460 nm.

HM74A

The ability of compounds to activate HM74A may be demonstrated, for example, using the following in vitro and in vivo assays:

In-Vitro Testing

For transient transfections, HEK293T cells (HEK293 cells stably expressing the SV40 large T-antigen) are maintained in DMEM containing 10% foetal calf serum and 2 mM glutamine. Cells are seeded in 90 mm culture dishes and grown to 60-80% confluence (18-24 h) prior to transfection. Human HM74A (GenBank™ accession number AY148884) is subcloned in to a mammalian expression vector (pcDNA3; Invitrogen) and transfected using Lipofectamine reagent. For transfection, 9 µg of DNA is mixed with 30 µl Lipofectamine in 0.6 ml of Opti-MEM (Life Technologies Inc.) and incubated at room temperature for 30 min prior to the addition of 1.6 ml of Opti-MEM. Cells are exposed to the Lipofectamine/DNA mixture for 5 h and 6 ml of 20% (v/v) foetal calf serum in DMEM is then added. Cells are harvested 48 h after transfection. Pertussis toxin treatment is carried out by supplementation into media at 50 ngml$^{-1}$ for 16 h. All transient transfection studies involve co-transfection of receptor together with the $G_{i/o}G$ protein, $G_{oi}$alpha.

For generation of stable cell lines the above method is used to transfect CHO-K1 cells seeded in six well dishes grown to 30% confluence. These cells are maintained in DMEM F-12 HAM media containing 10% foetal calf serum and 2 mM glutamine. 48 h post-transfection the media is supplemented with 400 µg/ml Geneticin (G418, Gibco) for selection of antibiotic resistant cells. Clonal CHO-K1 cell lines stably expressing HM74A are confirmed by [$^{35}$S]-GTPγS binding measurements, following the addition of nicotinic acid.

P2 membrane preparation—Plasma membrane-containing P2 particulate fractions are prepared from cell pastes frozen at −80° C. after harvest. All procedures are carried out at 4° C. Cell pellets are resuspended in 1 ml of 10 mM Tris-HCl and 0.1 mM EDTA, pH 7.5 (buffer A) and by homogenization for 20s with a Ultra Turrax followed by passage (5 times) through a 25-gauge needle. Cell lysates are centrifuged at 1,000 g for 10 min in a microcentrifuge to pellet the nuclei and unbroken cells and P2 particulate fractions are recovered by microcentrifugation at 16,000 g for 30 min. P2 particulate fractions are resuspended in buffer A and stored at −80° C. until required.

[$^{35}$S]-GTPγS binding—Assays are performed at room temperature either in 96-well format as described previously (Wieland, T. and Jakobs, K. H. (1994) Methods Enzymol. 237, 3-13) or in an adapted protocol carried out in 384-well format.

96-well format: Briefly, membranes (10 µg per point) are diluted to 0.083 mg/ml in assay buffer (20 mM HEPES, 100 mM NaCl, 10 mM MgCl$_2$, pH 7.4) supplemented with saponin (10 mg/l) and pre-incubated with 10 µM GDP. Various concentrations of nicotinic acid or related molecules are added, followed by [$^{35}$S]-GTPγS (1170 Ci/mmol, Amersham) at 0.3 nM (total vol. of 100 µl) and binding is allowed to proceed at room temperature for 30 min. Non-specific binding is determined by the inclusion of 0.6 mM GTP. Wheatgerm agglutinin SPA beads (Amersham) (0.5 mg) in 25 µl assay buffer are added and the whole is incubated at room temperature for 30 min with agitation. Plates are centrifuged at 1500 g for 5 min and bound [$^{35}$S]-GTPγS is determined by scintillation counting on a Wallac 1450 microbeta Trilux scintillation counter.

384-well format: Briefly, the dilution of standard or test compounds are prepared and added to a 384-well plate in a volume of 10 µl. Membranes (HM74A or HM74) are diluted in assay buffer (20 mM HEPES, 100 mM NaCl, 10 mM MgCl$_2$, pH7.4) supplemented with saponin (60 µg/ml), Leadseeker WGA beads (Amersham; 250 µg/well) and 10 µM GDP, so that the 20 µl volume added to each well contains 5 µg of membranes. [$^{35}$S]-GTPγS (1170 Ci/mmol, Amersham) is diluted (1:1500) in assay buffer and 20 µl added to each well. Following the addition of the radioligand, the plates are sealed, pulse spun and incubated for 4 hours at room temperature. At the end of the incubation period the plates are read on a Leadseeker machine (VIEWLUX PLUS; Perkin-Elmer) to determine the levels of specific binding.

In-Vivo Testing

HM74A agonists are tested in male Spague-Dawley rats (200-250 grams) which have been fasted for at least 12 hours prior to the study. The compounds are dosed intravenously (5 ml/kg) or by oral gavage (10 ml/kg). Blood samples (0.3 ml tail vein bleed) are taken pre-dose and at three times post-dose (times ranging from 15 minutes to 8 hours post-dose). Each blood sample is transferred to a heparin tube (Becton Dickinson Microtainer, PST LH) and centrifuged (10,000 g for 5 minutes) to produce a plasma sample. The plasma samples are assayed for levels of non-esterified fatty acids (NEFA) using a commercially available kit (Randox). Inhibition of plasma NEFA levels, relative to pre-dose levels, is used as a surrogate for HM74A agonist activity.

In order to determine whether compounds of the invention exhibit the flushing response associated with nicotinic acid, they are dosed to anaesthetized guinea-pigs. Nicotinic acid is used as positive control. Male Dunkin Hartley guinea pigs (300-800 g) are fasted for 12 hours prior to being anaesthetized with a mixture of Ketamine hydrochloride (Vetalar, 40 mg/kg i.m.), Xylazine (Rompun, 8 mg/kg i.m.) and sodium pentobarbitone (Sagatal, 30 mg/kg i.p.). Following anaesthesia a tracheostomy is performed and the animals are mechanically ventilated with room air (10-12 mL/kg, 60 breaths/min). A jugular vein, and a carotid artery, are cannulated for intravenous administration of test compound and collection of blood respectively. An infra-red temperature probe (Extech Instruments) is placed 3-5 mm from the tip of the left ear. Temperature measurements are recorded every minute from 5 minutes prior to test compound or nicotinic acid and up to 40 minutes post-administration of test compound or nicotinic acid. Data is automatically collected on a Psion computer before being transferred for data analysis within an Excel spreadsheet. Prior to, and at frequent time points after compound administration, blood samples (0.3 ml) are taken via the carotid arterial cannula and transferred to Microtainer (BD) tubes containing lithium heparin. The samples are mixed thoroughly on a blood roller and then stored on ice prior to centrifugation at 1200 g for 5 minutes.

Histamine

Compounds of the invention may be tested for in vitro biological activity in accordance with the following or similar assays:

H1 Receptor Cell Line Generation and FLIPR Assay Protocol

1. Generation of Histamine H1 Cell Line

The human H1 receptor can be cloned using known procedures described in the literature [Biochem. Biophys. Res. Commun., 201 (2):894, (1994)]. Chinese hamster ovary cells stably expressing the human H1 receptor can be generated according to known procedures described in the literature [Br. J. Pharmacol., 117 (6):1071, (1996)].

Histamine H1 Functional Antagonist Assay

The histamine H1 cell line can be seeded into non-coated black-walled clear bottom 384-well tissue culture plates in alpha minimum essential medium (Gibco/Invitrogen, cat. no. 22561-021), supplemented with 10% dialyzed foetal calf serum (Gibco/Invitrogen cat. no. 12480-021) and 2 mM L-glutamine (Gibco/Invitrogen cat. No. 25030-024) and maintained overnight at 5% $CO_2$, 37° C.

Excess medium can be removed from each well to leave 10 µl. 30 µl loading dye (250 µM Brilliant Black, 2 µM Fluo-4 diluted in Tyrodes buffer+probenecid (145 mM NaCl, 2.5 mM KCl, 10 mM HEPES, 10 mM D-glucose, 1.2 mM $MgCl_2$, 1.5 mM $CaCl_2$, 2.5 mM probenecid, pH adjusted to 7.40 with NaOH 1.0 M)) can be added to each well and the plates can be incubated for 60 min at 5% $CO_2$, 37° C.

10 µl of test compound, diluted to the required concentration in Tyrodes buffer+probenecid (or 10 µA Tyrodes buffer+probenecid as a control) can be added to each well and the plate incubated for 30 min at 37° C., 5% $CO_2$. The plates can be then placed into a FLIPR™ (Molecular Devices, UK) to monitor cell fluorescence ($\lambda$ex=488 nm, $\lambda$EM=540 nm) in the manner described in Sullivan et al. (In: Lambert D G (ed.), Calcium Signaling Protocols, New Jersey: Humana Press, 1999, pp. 125-136) before and after the addition of 10 µl histamine at a concentration that results in the final assay concentration of histamine being EC80.

Functional antagonism is indicated by a suppression of histamine induced increase in fluorescence, as measured by the FLIPR™ system (Molecular Devices). By means of concentration effect curves, functional affinities are determined using standard pharmacological mathematical analysis.

2. H3 Receptor Cell Line Generation, Membrane Preparation And Functional GTPγS Assay Protocols Generation of Histamine H3 Cell Line The histamine H3 cDNA can be isolated from its holding vector, pcDNA3.1 TOPO (InVitrogen), by restriction digestion of plasmid DNA with the enzymes BamH1 and Not-1 and ligated into the inducible expression vector pGene (InVitrogen) digested with the same enzymes. The GeneSwitch™ system (a system where in transgene expression is switched off in the absence of an inducer and switched on in the presence of an inducer) can be performed as described in U.S. Pat. Nos. 5,364,791; 5,874,534; and 5,935,934. Ligated DNA can be transformed into competent DH5α E. coli host bacterial cells and plated onto Luria Broth (LB) agar containing Zeocin™. (an antibiotic which allows the selection of cells expressing the sh ble gene which is present on pGene and pSwitch) at 50 µgml$^{-1}$. Colonies containing the re-ligated plasmid can be identified by restriction analysis. DNA for transfection into mammalian cells can be prepared from 250 ml cultures of the host bacterium containing the pGeneH3 plasmid and isolated using a DNA preparation kit (Qiagen Midi-Prep) as per manufacturers guidelines (Qiagen).

CHO K1 cells previously transfected with the pSwitch regulatory plasmid (InVitrogen) can be seeded at 2×10$^6$ cells per T75 flask in Complete Medium, containing Hams F12 (GIBCOBRL, Life Technologies) medium supplemented with 10% v/v dialysed foetal bovine serum, L-glutamine, and hygromycin (100 µgml$^{-1}$), 24 hours prior to use. Plasmid DNA can be transfected into the cells using Lipofectamine plus according to the manufacturers guidelines (InVitrogen). 48 hours post transfection cells can be placed into complete medium supplemented with 500 µgml$^{-1}$ Zeocin™.

10-14 days post selection 10 nM Mifepristone (InVitrogen), can be added to the culture medium to induce the expression of the receptor. 18 hours post induction cells can be detached from the flask using ethylenediamine tetra-acetic acid (EDTA; 1:5000; InVitrogen), following several washes with phosphate buffered saline pH 7.4 and resuspended in Sorting Medium containing Minimum Essential Medium (MEM), without phenol red, and supplemented with Earles salts and 3% Foetal Clone II (Hyclone). Approximately 1×10$^7$ cells can be examined for receptor expression by staining with a rabbit polyclonal antibody, 4a, raised against the N-terminal domain of the histamine H3 receptor, incubated on ice for 60 min, followed by two washes in sorting medium. Receptor bound antibody can be detected by incubation of the cells for 60 min on ice with a goat anti rabbit antibody, conjugated with Alexa 488 fluorescence marker (Molecular Probes). Following two further washes with Sorting Medium, cells can be filtered through a 50 µm Filcon™ (BD Biosciences) and then analyzed on a FACS Vantage SE Flow Cytometer fitted with an Automatic Cell Deposition Unit. Control cells can be non-induced cells treated in a similar manner. Positively stained cells can be sorted as single cells into 96-well plates, containing Complete Medium containing 500 µgml$^{-1}$ Zeocin™ and allowed to expand before reanalysis for receptor expression via antibody and ligand binding studies. One clone, 3H3, can be selected for membrane preparation.

Membrane Preparation From Cultured Cells

All steps of the protocol are carried out at 4° C. and with pre-cooled reagents. The cell pellet is resuspended in 10 volumes of homogenization buffer (50 mM N-2-hydroxyethylpiperazine-N'-2-ethanesulfonic acid (HEPES), 1 mM ethylenediamine tetraacetic acid (EDTA), pH 7.4 with KOH, supplemented with 10$^{-6}$ M leupeptin (acetyl-leucyl-leucyl-arginal; Sigma L2884), 25 µgml$^{-1}$ bacitracin (Sigma B0125), 1 mM phenylmethylsulfonyl fluoride (PMSF) and 2×10$^{-6}$ M pepstain A (Sigma)). The cells are then homogenised by 2×15 second bursts in a 1 litre glass Waring blender, followed by centrifugation at 500 g for 20 min. The supernatant is then spun at 48,000 g for 30 min. The pellet is resuspended in homogenization buffer (4× the volume of the original cell pellet) by vortexing for 5 seconds, followed by homogenization in a Dounce homogenizer (10-15 strokes). At this point the preparation is aliquoted into polypropylene tubes and stored at −80° C.

Histamine H3 Functional Antagonist Assay

For each compound being assayed, in a solid white 384 well plate, is added:—

(a) 0.5 µl of test compound diluted to the required concentration in DMSO (or 0.5 µl DMSO as a control);

(b) 30 µl bead/membrane/GDP mix prepared by mixing Wheat Germ Agglutinin Polystyrene LeadSeeker™ (WGA PS LS) scintillation proximity assay (SPA) beads with membrane (prepared in accordance with the methodology described above) and diluting in assay buffer (20 mM N-2-Hydroxyethylpiperazine-N'-2-ethanesulfonic acid (HEPES)+100 mM NaCl+10 mM $MgCl_2$, pH 7.4 NaOH) to give a final volume of 30 µl which contains 5 µg protein and 0.25 mg bead per well, incubating at room temperature for 60 min on a roller and, just prior to addition to the plate, adding 10 µM final concentration of guanosine 5' diphosphate (GDP) (Sigma; diluted in assay buffer);

(c) 15 µl 0.38 nM [$^{35}$S]-GTPγS (Amersham; Radioactivity concentration=37 MBqml$^{-1}$; Specific activity=1160 Cimmol$^{-1}$), histamine (at a concentration that results in the final assay concentration of histamine being EC80).

After 2-6 hours, the plate is centrifuged for 5 min at 1500 rpm and counted on a Viewlux counter using a 613/55 filter for 5 minplate$^{-1}$. Data is analyzed using a 4-parameter logistical equation. Basal activity used as minimum i.e. histamine not added to well.

Bioavailability and CNS penetration of compounds of the invention may be assayed in the following, or similar, assays.

1. CNS Penetration Method

Compounds can be dosed intravenously at a nominal dose level of 1 mgkg–1 to male CD Sprague Dawley rats. Compounds can be formulated in 5% DMSO/45% PEG200/50% water. Blood samples can be taken under terminal anaesthesia with isoflurane at 5 min post-dose and the brains can be also removed for assessment of brain penetration. Blood samples can be taken directly into heparinised tubes. Blood samples can be prepared for analysis using protein precipitation and brain samples can be prepared using extraction of drug from brain by homogenization and subsequent protein precipitation. The concentration of parent drug in blood and brain extracts can be determined by quantitative LC-MS/MS analysis using compound-specific mass transitions.

2. Rat Pharmacokinetics Method

Compounds can be dosed to male CD Sprague Dawley rats by single intravenous or oral administration at a nominal dose level of 1 mgkg$^{-1}$ and 3 mgkg$^{-1}$ respectively. Compounds can be formulated in 5% DMSO/45% PEG200/50% water. An intravenous profile can be obtained by taking serial or terminal blood samples at 0.083, 0.25, 0.5, 1, 2, 4, and 7 h post-dose. An oral profile can be obtained by taking serial or terminal blood samples at 0.25, 0.5, 1, 2, 4, 7 and 12 h post-dose. Blood samples can be taken directly into heparinised tubes. Blood samples can be prepared by protein precipitation and subjected to quantitative analysis by LC-MS/MS using compound-specific mass transitions. Drug concentration-time profiles can be generated and non-compartmental PK analysis used to generate estimates of half-life, clearance, volume of distribution and oral bioavailability.

3. Dog Pharmacokinetics Method

Compounds can be dosed to male Beagle dogs by single intravenous or oral administration at a nominal dose level of 1 mgkg$^{-1}$ and 2 mgkg$^{-1}$ respectively. The study can be carried out according to a crossover design such that the same dog can be used for both dosing events and the dosing events occurred 1 week apart. Compounds can be formulated in 5% DMSO/ 45% Peg200/50% water. An intravenous profile can be obtained by taking serial blood samples at 0.083, 0.25, 0.5, 0.75, 1, 2, 4, 6 & 12 h post-dose. An oral profile can be obtained by taking serial blood samples at 0.25, 0.5, 0.75, 1, 2, 4, 6, 12 & 24 h post-dose. Blood samples can be taken directly into heparinised tubes. Blood samples can be prepared by protein precipitation and subjected to quantitative analysis by LC-MS/MS using compound-specific mass transitions. Drug concentration-time profiles can be generated and non-compartmental PK analysis used to generate estimates of half-life, clearance, volume of distribution and oral bioavailability.

Beta-Adrenergic Receptor Kinase
Beta-2-Adrenergic Receptor In Vitro Functional Assay The beta-2-adrenergic receptor functional activity of compounds of the invention can be tested follows.

Cell Seeding and Growth:

Primary bronchial smooth muscle cells from a 21 yr. old male (Clonetics, San Diego Calif.) can be seeded at 50,000 cells/well in 24-well tissue culture plates. The media used can be Clonetic's SmBM-2 supplemented with hEGF, Insulin, hFGF, and Fetal Bovine Serum. Cells can be grown two days at 37° C., 5% CO, until confluent monolayers can be seen.

Agonist Stimulation of Cells

The media can be aspirated from each well and replaced with 250 ml fresh media containing 1 mM IBMX, a phosphodiesterase inhibitor (Sigma, St Louis, Mo.). Cells can be incubated for 15 minutes at 37° C., and then 250 ml of agonist at appropriate concentration can be added. Cells can be then incubated for an additional 10 minutes. Media can be aspirated and 500 ml cold 70% EtOH can be added to cells, and then removed to an empty 96-well deep-well plate after about 5 minutes. This step can be then repeated. The deep-well plate can be then spun in a speed-vac until all EtOH dried off, leaving dry pellets. cAMP (pmol/well) can be quantitated using a cAMP ELISA kit from Stratagene (La Jolla, Calif.). EC50 curves can be generated using the 4-parameter fit equation:

$$y=(a-d)/(1+(x/c)^b)+d, \text{ where,}$$

y=cpm a=total binding c=IC$_{50}$
x=[compound] d=NS binding b=slope
Fix NS binding and allow all other parameters to float.
Beta-2-Adrenergic Receptor In Vitro Radioligand Binding Assay The beta-1/2-adrenergic receptor binding activity of compounds of the invention can be tested follows. SF9 cell membranes containing either beta-1 or beta-2-adrenergic receptor (NEN, Boston, Mass.) can be incubated with 0.07 nM $^{121}$I-iodocyanopindolol (NEN, Boston, Mass.) in binding buffer containing 75 mM Tris-HCl (pH 7.4), 12.5 mM MgCl, and 2 mM EDTA and varying concentrations of test compounds or buffer only (control) in 96-well plates. The plates can be incubated at room temperature with shaking for 1 hour. The receptor bound radioligand can be harvested by filtration over 96-well GF/B filter plates (Packard, Meriden, Conn.) pre-blocked with 0.3% polyethylenimine and washed twice with 200 μl PBS using cell harvester. The filters can be washed thrice with 200 μl PBS using cell harvester and then resuspended in 40 μl scintillation cocktail. The filter-bound radioactivity can be measured with a scintillation counter and IC50 curves are generated using the standard 4-parameter fit equation described above.

In Vivo Inhalation Guinea Pig Salivation Assay

Guinea pigs (Charles River, Wilmington, Mass.) weighing 200-350 g are acclimated to the in-house guinea pig colony for at least 3 days following arrival. Test compound or vehicle are dosed via inhalation (1H) over a 10 minute time period in a pie shaped dosing chamber (R+S Molds, San Carlos, Calif.). Test solutions are dissolved in sterile water and delivered using a nebulizer filled with 5.0 mL of dosing solution. Guinea pigs are restrained in the inhalation chamber for 30 minutes. During this time, guinea pigs are restricted to an area of approximately 110 sq. cm. This space is adequate for the animals to turn freely, reposition themselves, and allow for grooming. Following 20 minutes of acclimation, guinea pigs are exposed to an aerosol generated from a LS Star Nebulizer Set (Model 22F51, PARI Respiratory Equipment, Inc. Midlothian, Va.) driven by house air at a pressure of 22 psi. Upon completion of nebulization, guinea pigs are evaluated at 1.5, 6, 12, 24, 48, or 72 hrs after treatment.

Guinea pigs are anesthetized one hour before testing with an intramuscular (IM) injection of a mixture of ketamine 43.75 mg/kg, xylazine 3.5 mg/kg, and acepromazine 1.05 mg/kg at an 0.88 mL/kg volume. Animals are placed ventral side up on a heated (37° C.) blanket at a 20 degree incline with their head in a downward slope. A 4-ply 2×2 inch gauze pad (Nu-Gauze General-use sponges, Johnson and Johnson, Arlington, Tex.) is inserted in the guinea pig's mouth. Five minutes later, the muscarinic agonist pilocarpine (3.0 mg/kg, s.c.) is administered and the gauze pad is immediately discarded and replaced by a new pre-weighed gauze pad. Saliva is collected for 10 minutes, at which point the gauze pad is weighed and the difference in weight recorded to determine the amount of accumulated saliva (in mg). The mean amount of saliva collected for animals receiving the vehicle and each dose of test compound is calculated. The vehicle group mean is considered to be 100% salivation. Results are calculated using result means (n=3 or greater). Confidence intervals (95%) are calculated for each dose at each time point using two-way ANOVA. This model is a modified version of the procedure described in Rechter, "Estimation of anticholinergic drug effects in mice by antagonism against pilocarpine-induced salivation" Ata Pharmacol Toxicol, 1996, 24:243-254.

The mean weight of saliva in vehicle-treated animals, at each pre-treatment time, is calculated and used to compute % inhibition of salivation, at the corresponding pre-treatment time, at each dose. The inhibition dose-response data are fitted to a four parameter logistic equation using GraphPad Prism, version 3.00 for Windows (GraphPad Software, San Diego, Calif.) to estimate anti-sialagogue ID50 (dose required to inhibit 50% of pilocarpine-evoked salivation). The equation used is as follows: $Y=Min+(Max-Min)/(1+10^{(log\ ID50-X)*Hillslope})$ where X is the logarithm of dose, Y is the response (% inhibition of salivation). Y starts at Min and approaches asymptotically to Max with a sigmoidal shape.

The ratio of the anti-sialagogue ID50 to bronchoprotective ID50 is used to compute the apparent lung-selectivity index of the test compound. Generally, compounds having an apparent lung-selectivity index greater than about 5 are preferred.

Protein Kinase C
In Vitro Protein Kinase C (PKC) Assay

The assay components are in a total of 100 μA, including 45 mM Tris-HCl buffer pH 7.5 (Life Technologies), 0.75 mM calcium acetate (Wako), 3.6 mM magnesium chloride (Wako), 1.875 mM DL-dithiothreitol (Sigma), 18.75 μg/ml L-(α-phosphatidyl-L-serine (Sigma), 1.5 μg/ml phorbol 12-myristate 13-acetate (Sigma), 2.5 μM biotinylated peptide (neurogranin 28-43, Asahi Techno Glass), 10 μl of 1.0% aqueous DMSO or DMSO/inhibitor and 0.3 μM (gamma 33P) ATP (NEN). The reaction can be initiated by the addition of human recombinant PKCα (Calbiochem), PKCβ2 (Calbiochem) or PKCγ (Calbiochem or in-house preparation), incubated at room temperature for 15 minutes and stopped by adding 100 μl of 5 mg/ml streptavidin SPA beads (Amersham Pharmacia Biotech) including 50 μM ATP (Sigma), 5 mM EDTA (Dojindo) and 0.1% Triton X-100 (Wako) in phosphate-buffered saline (Nissui). The reaction mixture can be further incubated for 15 minutes, centrifuged at 1000 rpm for 1 minute and the radioactivity can be quantified by TopCount (Packard).

In Vivo Assay: Neuropathic Pain Model

Chronic constriction injury (CCI) model (Bennett et al., Pain 33 87 1988) can be used to investigate the effect of compounds on rat neuropathic pain model. SD rats (male, 8 weeks, Nippon SLC) can be used in this assay. CCI of sciatic nerve can be made by tying loose ligature with 4-0 chromic gut around aciatic nerve four times with 1 mm spacing. In sham-operated mice, the nerve can be exposed without ligation.

Detection of Mechanical Allodynia

Efficacy of drugs on rat neurophatic pain model can be examined by using von Frey Hair test (Semmes-Weinstein Monofilaments; North Coast Medical, Inc.). (Mechanical allodynia can be examined by using von Frey Hair (Semmes-Weinstein Monofilaments; North Coast Medical, Inc.). Rats can be placed on a mesh floor, so that the plantar surface of the hindpaw can be stimulated from below. Each hair can be applied to the midplantar of hindpaw 10 times in order of increasing stiffness. The first hair in the series that evoked at least 1 response can be designated the threshold.) This test can be performed 14 days after the surgery.

Protein Kinase A
In Vitro Assay: Inhibition of Protein Kinase A Activity

The PKA kinase activity assay utilizes a radioactivity-based format in a 96-well PCR plate with radioactive readout. The PKA activity can be assayed in a 25 μL assay mixture containing 25 mM HEPES (pH 7.0), 250 μM ATP, 10 mM $MgCl_2$, 1 mM DTT, 1 mM EDTA (pH 8). 2% DMSO. 250 ng/mL Histone $H_2B$ (Roche 223 514), and 2 ng/mL PKA (catalytic subunit, bovine heart, Calbiochem 539486, specific activity=1170 pmol/min*μg). Compounds can be screened for inhibition of the PKA kinase activity at a concentration of 10 μM. The kinase reaction can be allowed to proceed at 37° C. for 30 minutes, then the reaction can be stopped by addition of 5 μL of 0.5M EDTA (pH 8). 5 μL of each solution can be then spotted onto the corresponding square of a filtermat (8×12 glassfibre mat 90×120 mm, PE-Wallac 1450-421). The filtermat can be allowed to dry and washed once with 10% TCA, 2% PPA, 500 mM NaCl each for 30 minutes at rt. Two further washings in 10% TCA and 2% PPA for 30 minutes can be performed, then a final 30 minute wash in 99% EtOH at rt can be done and the filtermat can be air dried. The dry filtermat can be then placed in a sample bag with a Meltilex sheet (Melt-on scintillator sheets 73×109 mm, PE-Wallac 1450-441 for filtermat A) over the filtermat. The bag can be trimmed to fit into the microplate heatsealer (PE-Wallac 1495-021). The heatsealer is used to melt the Meltilex on the filtermat. The bag containing the filtermat and the melted Meltilex can be then placed into a filter cassette and counted using the Microbeta Jet Scintillation and Luminescence Counter PE-Wallac 1450.

$K_{ATP}$
In Vitro Binding Affinity of the Test Compounds to Rodent $K_{ATP}$ Channels Competitive binding experiments can be performed to characterize the affinity of the test compounds for the binding sites for sulfonylureas and $K_{ATP}$ channel openers (=KCOs) on hamster SUR1. To assess the affinity for the sulfonylurea site membranes from COS-cells transiently expressing hamster SUR1 can be incubated in the presence of [$^3$H] glibenclamide with increasing concentrations of test compounds. The affinity for binding to the KCO site can be assessed by incubations in the additional presence of 100 μM MgATP (see Schwanstecher M., et al. Naunyn-Schmiedeberg's Arch. Pharmacol. 343 (1991) 83-89 and Schwanstecher M. et al., EMBO J. 17 (1998) 5529-5535 (=Schwanstecher et al., 1998)). For each test compound 4 displacement curves can be measured (+−MgATP from the human and hamster isoform). Per curve 9-15 distinct concentrations can be tested covering the relevant range. All measurements can be repeated at least 5 times in independent experiments.

Similar to SUR1 (see above) competitive binding experiments can be performed to characterize the affinity of the test compounds for the binding sites for sulfonylureas and KCOs on rat SUR2A. The affinity for the KCO site on SUR2A can be assessed by displacement of [$^3$H]P1075 (see Schwanstecher et al., 1998; Dorschner H. et al. Mol. Pharmacol. 55 (1999) 1060-1066 (=Dorschner et al., 1999)). The affinity of [$^3$H]glibenclamide for the human SUR2 isoforms, however, is too weak to allow direct detection of binding using filtration assays. Therefore, two strategies can be used to detect binding to the sulfonylurea site on SUR2A. First, binding can be detected indirectly through allosteric displacement of [$^3$H] P1075 (Dorschner et al., 1999). Second, a mutated SUR2A (SUR2A$_{Y1205S}$, see above) with increased affinity for [$^3$H] glibenclamide allowing direct displacement of this tracer can be used. This second approach can be chosen to enable discrimination between allosteric and competitive interaction with the KCO site and make sure that binding of ligands which do not induce allosteric displacement are not missed.

Membranes from COS-cells transiently expressing rat SUR2A can be incubated in the presence of the radioligands with increasing concentrations of test compounds as described above. The affinity for binding to the KCO site can be assessed by incubations in the additional presence of 100 µM MgATP (Schwanstecher et al., 1991 and 1998). For each test compound 4 displacement curves can be measured (displacement of [$^3$H]P1075 from the rat isoform of the wild type receptor and displacement of [$^3$H]glibenclamide from the rat isoform of SUR2A$_{Y1205S}$). Per curve 9-15 distinct concentrations can be tested covering the relevant range. All measurements can be repeated at least 5 times in independent experiments.

[$^3$H]P1075 (specific activity 116 Ci mmol$^{-1}$) can be purchased from Amersham Buchler (Braunschweig, Germany). [$^3$H]glibenclamide (specific activity 51 Ci mmol$^{-1}$) can be obtained from NEN (Dreieich, Germany). If suitable, stock solutions can be prepared in dimethylsulfoxide with a final solvent concentration in the media below 1%.

SUR- or Kir6.x isoforms can be used either subcloned in the pcDNA (hamster SUR1, mouse Kir6.2) or pCMV vector (rat SUR2A, SUR2B).

Rodent SUR-isoforms and K$_{ATP}$ channels can be transiently expressed in COS-1 cells as described (see Schwanstecher et al., 1998); Dorschner et al., 1999); Uhde I. et al. J Biol Chem 274 (1999) 28079-28082; Gross I. et al. Mol. Pharmacol. 56 (1999) 1370-1373; Markworth E., Diabetes 49 (2000) 1413-1418). A mutated form of the SUR2 isoforms with the phenylalanine residue in position 1205 substituted with a serine (SUR2$_{Y1205S}$) can be used to allow detection of binding to the sulfonylurea site of these isoforms by displacement of [$^3$H]glibenclamide (Uhde I., Dissertation 2001). Briefly, COS-1 cells cultured in DMEM HG (10 mM glucose), supplemented with 10% fetal calf serum (FCS), can be plated at a density of 5×10$^5$ cells per dish (94 mm) and allowed to attach overnight. For transfection the cells can be incubated 4 hours in a Tris-buffered salt solution containing DNA (5-10 µg/ml) plus DEAE-dextran (1 mg/ml), 2 min in HEPES-buffered salt solution plus dimethylsulfoxide (10%) and 4 hours in DMEM-HG plus chloroquine (100 µM). Cells can be then returned to DMEM-HG plus 10% FCS. Membranes can be prepared 60-72 h post transfection as described (Schwanstecher M. et al., Br. J. Pharmacol. 106 (1992) 295-301 (=Schwanstecher et al., 1992)). For binding experiments resuspended membranes (final protein concentration 5-50 µg/ml) can be incubated in "Tris-buffer" (50 mM, pH 7.4) containing either [$^3$H]glibenclamide (final concentration 0.3 nM or 3 nM and nonspecific binding defined by 100 nM or 1 µM glibenclamide for SUR1 or SUR2$_{Y1205S}$-isoforms, respectively) or [$^3$H]P1075 (final concentration 3 nM, nonspecific binding defined by 100 µM pinacidil) and increasing concentrations of the test compounds. The free Mg$^{2+}$ concentration can be kept close to 0.7 mM. ATP (0.1 mM) can be added to incubation media to enable KCO (e.g. diazoxide, [$^3$H]P1075) binding (see Schwanstecher et al., 1998). Incubations can be carried out for 1 h at room temperature and can be terminated by rapid filtration through Whatman GF/B filters.

The inhibition constant (Ki value) of the test substances can be calculated from the respective IC50 value, and can be stated as the negative logarithmised value thereof (pK$_i$).

The binding affinity and selectivity of a given compound towards SUR1 and SUR2 can be used as criteria to reflect the modulation of the K-ATP channel (e.g. N,N-414, with a pKi 6.2, is 100 times more potent than diazoxide, with a pKi 3.8, to inhibit glucose-stimulated insulin release). The binding data can be used as first estimate of the potential of a given compound to preserve beta cell function and to prevent or delay the progression of diabetes.

2. In Vitro Binding Affinity of the Test Compounds to Rodent CB$_1$ Receptors (Radioligand: Antagonist [$^3$H]-SR141716A)

The affinity of the compounds of the invention for cannabinoid CB$_1$ receptors can be determined using membrane preparations of Chinese hamster ovary (CHO) cells in which the human cannabinoid CB$_1$ receptor is stably transfected in conjunction with [$^3$H]-SR141716A as radioligand. After incubation of a freshly prepared cell membrane preparation with the [$^3$H]-ligand, with or without addition of compounds of the invention, separation of bound and free ligand is performed by filtration over glassfiber filters. Radioactivity on the filter is measured by liquid scintillation counting.

3. In Vitro Binding Affinity of the Test Compounds to Rodent CB$_1$ Receptors (Radioligand: Agonist CP-55.940)

The affinity of the compounds of the invention for cannabinoid CB$_1$ receptors can be determined using membrane preparations of Chinese hamster ovary (CHO) cells in which the human cannabinoid CB$_1$ receptor is stably transfected in conjunction with [$^3$H]CP-55,940 as radioligand. After incubation of a freshly prepared cell membrane preparation with the [$^3$H]-ligand, with or without addition of compounds of the invention, separation of bound and free ligand is performed by filtration over glassfiber filters. Radioactivity on the filter is measured by liquid scintillation counting.

4. Functional Activity of the Test Compounds at Human Cannabinoid CB$_1$ Receptors In vitro CB$_1$ receptor antagonism can be assessed with the human CB$_1$ receptor cloned in CHO cells. CHO cells can be grown in a Dulbecco's Modified Eagle's culture medium (=DMEM) and supplemented with 10% heat-inactivated fetal calf serum. The medium can be aspirated and replaced by DMEM, without fetal calf serum, but containing [$^3$H]-arachidonic acid and incubated overnight in a cell culture stove (5% CO$_2$/95% air; 37° C.; water-saturated atmosphere). During this period [$^3$H]-arachidonic acid can be incorporated in membrane phospholipids. On the test day, medium can be aspirated and cells can be washed three times using 0.5 mL DMEM, containing 0.2% bovine serum albumin (BSA). Stimulation of the CB$_1$ receptor by WIN 55,212-2 led to activation of PLA$_2$ followed by release of [$^3$H]-arachidonic acid into the medium. This WIN 55,212-2-induced release can be concentration-dependently antagonized by CB$_1$ receptor antagonists. The CB$_1$ antagonistic potencies of the test compounds are expressed as pA$_2$ values.

5. Determination of the Antagonist Effects of Compounds on Insulin Secretion in Rat Perifused Pancreatic Islets—Simple Screen for Antagonist Activity Animals: Male Wistar rats in the weight range 175-200 g can be group housed in standard animal cages at a temperature of 21+−2° C. and humidity of 55+−10%. Animals can be maintained on a 12 h light-dark cycle (lights on 06.00-18.00 h) with free access to standard rodent diet (B&K Universal Ltd standard rat and mouse diet (BK 001P), Beekay Feeds, B&K Universal Ltd, Hull, East Riding of Yorkshire) and tap water. The rats should be accustomed to these conditions for at least one week before experimentation.

Experimental procedures: After the rats are sacrificed, the branch of the bile duct leading to the liver and the duodenal end of the duct in the pancreas can be clamped and the pancreas distended by injection of ice-cold 0.9 mg/ml collagenase solution into the bile duct. The pancreas can be then removed and incubated statically for 10-12 min at 37° C. Following the incubation, 10 ml of cold buffer can be added and the suspension shaken vigorously by hand for 1 min. The islets can be allowed to settle for 5 min on ice and washed three times using ice-cold buffer. Well formed and good sized islets from 3 rats can be hand-picked (under a low power microscope) and pooled and a final selection of islet transferred to the perifusion apparatus. Oxygenated (95% $O_2$/5% $CO_2$) Gey & Gey buffer containing 1 mg/ml bovine serum albumin and 4 mM glucose can be used throughout the experiment unless otherwise stated (see Dickinson et al. Eur J Pharmacol 1997; 339:69-76 for further details).

Compounds can be either tested at an advised concentration or the solubility can be determined in the experimental conditions and a maximum soluble drug concentration used for experiments (DMSO or ethanol will be used as the solvents at a maximum 0.1% in the assay buffer).

On each day, two experiments can be performed in parallel in 2 identical, independent sets of perifusion apparatus each consisting of sufficient number of chambers. Each chamber can be loaded with 20 hand-picked islets. Islets can be perifused for an initial 30 min period in media containing 4 mM glucose. Perifusate can be then collected at 2 min intervals for the remainder of the experiment. After the first 10 min of the experiment (to collect baseline insulin values), the media in each chamber can be switched to one containing 11 mM glucose and the relevant drug concentration/vehicle/diazoxide concentration and perifusate collected for a further 62 min to produce a total of 36 fractions for each chamber.

Perifusate samples can be then pooled to create 3 samples per chamber as follows: Baseline (4 mM): Samples 1-5 (first 10 minutes); 0-30 minutes (11 mM glucose): Samples 6-21; 30-60 minutes (11 mM glucose): Samples 22-36

Perifusate fractions can be stored at −75° C. until required for insulin assay. Insulin content of fractions can be assayed using a 96-well ELISA assay (Mercodia). Initial insulin assays can be performed in triplicate on three pooled fractions from each chamber (18 samples per experiment, 108 samples in total for 6 experiments).

Protease Activated Receptor (PAR1)
In Vitro Testing Procedure for Thrombin Receptor Antagonists:

Preparation of [$^3$H]haTRAP: A(pF-F)R(ChA)(hR)(I$_2$-Y)-NH$_2$ (1.03 mg) and 10% Pd/C (5.07 mg) can be suspended in DMF (250 µl) and diisopropylethylamine (10 µl). The vessel can be attached to the tritium line, frozen in liquid nitrogen and evacuated. Tritium gas (342 mCi) can be then added to the flask, which can be stirred at room temperature for 2 hours. At the completion of the reaction, the excess tritium can be removed and the reacted peptide solution can be diluted with DMF (0.5 ml) and filtered to remove the catalyst. The collected DMF solution of the crude peptide can be diluted with water and freeze dried to remove the labile tritium. The solid peptide can be redissolved in water and the freeze drying process repeated. The tritiated peptide ([$^3$H]haTRAP) can be dissolved in 0.5 ml of 0.1% aqueous TFA and purified by HPLC using the following conditions: column, Vydac C18, 25 cm×9.4 mm I.D.; mobile phase, (A) 0.1% TFA in water, (B) 0.1% TFA in CH$_3$CN; gradient, (A/B) from 100/0 to 40/60 over 30 min; flow rate, 5 ml/min; detection, UV at 215 nm. The radiochemical purity of [$^3$H]haTRAP can be 99% as analyzed by HPLC. A batch of 14.9 mCi at a specific activity of 18.4 Ci/mmol can be obtained.

Preparation of Platelet Membranes: Platelet Membranes can be Prepared using a modification of the method of Natarajan et al (Natarajan et al, Int. J. Petide Protein Res., vol. 45, pp. 145-151 (1995) from 20 units of platelet concentrates obtained from the North Jersey Blood Center (East Orange, N.J.) within 48 hours of collection. All steps can be carried out at 40° C. under approved biohazard safety conditions. Platelets can be centrifuged at 100×g for 20 minutes at 40° C. to remove red cells. The supernatants can be decanted and centrifuged at 3000×g for 15 minutes to pellet platelets. Platelets can be resuspended in 10 mM Tris-HCl, pH 7.5, 150 mM NaCl, 5 mM EDTA, to a total volume of 200 ml and centrifuged at 4400×g for 10 minutes. This step can be repeated two additional times. Platelets can be resuspended in 5 mM Tris-HCl, pH 7.5, 5 mM EDTA to a final volume of approximately 30 ml and can be homogenized with 20 strokes in a Dounce homogenizer. Membranes can be pelleted at 41,000×g, resuspended in 40-50 ml 20 mM Tris-HCl, pH 7.5, 1 mM EDTA, 0.1 mM dithiothreitol, and 10 ml aliquots can be frozen in liquid $N_2$ and stored at −80° C. To complete membrane preparation, aliquots can be thawed, pooled, and homogenized with 5 strokes of a Dounce homogenizer. Membranes can be pelleted and washed 3 times in 10 mM triethanolamine-HCl, pH 7.4, 5 mM EDTA, and resuspended in 20-25 ml 50 mM Tris-HCl, pH 7.5, 10 mM MgCl$_2$, 1 mM EGTA, and 1% DMSO. Aliquots of membranes can be frozen in liquid $N_2$ and stored at −80° C. Membranes can be stable for at least 3 months. 20 units of platelet concentrates typically yielded 250 mg of membrane protein. Protein concentration can be determined by a Lowry assay (Lowry et al, J. Biol. Chem., vol. 193, pp. 265-275 (1951).

High Throughput Thrombin Receptor Radioligand Binding Assay: Thrombin receptor antagonists can be screened using a modification of the thrombin receptor radioligand binding assay of Ahn et al. (Ahn et al, Mol Pharmacol., vol. 51, p. 350-356 (1997). The assay can be performed in 96 well Nunc plates (Cat. No. 269620) at a final assay volume of 200 µl. Platelet membranes and [$^3$H]haTRAP can be diluted to 0.4 mg/ml and 22.2 nM, respectively, in binding buffer (50 mM Tris-HCl, pH 7.5, 10 mM MgCl$_2$, 1 mM EGTA, 0.1% BSA). Stock solutions (10 mM in 100% DMSO) of test compounds can be further diluted in 100% DMSO. Unless otherwise indicated, 10 µl of diluted compound solutions and 90 µl of radioligand (a final concentration of 10 nM in 5% DMSO) can be added to each well, and the reaction can be started by the addition of 100 µl of membranes (40 µg protein/well). Compounds can be tested at three concentrations (0.1, 1 and 10 µM). The plates can be covered and vortex-mixed gently on a Lab-Line Titer Plate Shaker for 1 hour at room temperature. Packard UniFilter GF/C filter plates can be soaked for at least 1 hour in 0.1% polyethyleneimine. The incubated membranes can be harvested using a Packard FilterMate Universal Harvester and can be rapidly washed four times with 300 µl ice cold 50 mM Tris-HCl, pH 7.5, 10 mM MgCl$_2$, 1 mM EGTA. MicroScint 20 scintillation cocktail (25 µl) can be added to each well, and the plates can be counted in a Packard TopCount Microplate Scintillation Counter. The specific binding can be defined as the total binding minus the nonspecific binding observed in the presence of excess (50 µM) unlabeled haTRAP. The % Inhibition by a compound of [$^3$H]haTRAP binding to thrombin receptors can be calculated from the following relationship: % Inhibition=Total xx binding−Binding xx in xx the xx presence xx of xx a xx test xx compound Total xx binding−Nonspecific xx binding 100

Affinity values ($K_i$) can be then determined using the following formula: K i=IC 50 1+[concentration xx of xx radioligand affinity xx (KD) xx of xx radioligand] Hence, a lower value of $K_i$ indicates greater binding affinity.

A(pF-F)R(ChA)(hR)Y-$NH_2$ and A(pF-F)R(ChA)(hR)($I_{hd}$ 2-Y)-$NH_2$, can be custom synthesized by AnaSpec Inc. (San Jose, Calif.). The purity of these peptides can be >95%. Tritium gas (97%) can be purchased from EG&G Mound, Miamisburg Ohio. The gas can be subsequently loaded and stored on an IN/US Systems Inc. Trisorber. MicroScint 20 scintillation cocktail can be obtained from Packard Instrument Co.

Protocol for Ex-Vivo Platelet Aggregation in Cynomolgus Whole Blood Drug Administration and Blood Collection.

Conscious chaired cynomolgus monkeys are allowed to equilibrate for 30 min. A needle catheter is inserted into a brachial vein for infusion of test drugs. Another needle catheter is inserted into the other brachial or saphenous vein and used for blood sampling. In those experiments where the compound is administered orally only one catheter is used. A baseline blood sample (1-2 ml) is collected in vacutainer tubes containing a thrombin inhibitor CVS 2139 (100 μg/0.1 ml saline) as an anticoagulant. The drug is then infused intravenously over a period of 30 min. Blood samples (1 ml) are collected at 5, 10, 20, 30 min during and 30, 60, 90 min after termination of the drug infusion. In PO experiments the animals are dosed with the drug using a gavage cannula. Blood samples are collected at 0, 30, 60, 90, 120, 180, 240, 300, 360 min after dosing. 0.5 ml of the blood is used for whole blood aggregation and the other 0.5 ml is used for determining the plasma concentration of the drug or its metabolites. Aggregation is performed immediately after collection of the blood sample as described below.

Whole Blood Aggregation

A 0.5 ml blood sample is added to 0.5 ml of saline and warmed to 37° C. in a Chronolog whole blood aggregometer. Simultaneously, the impedance electrode is warmed in saline to 37° C. The blood sample with a stir bar is placed in the heating block well, the impedance electrode is placed in the blood sample and the collection software is started. The software is allowed to run until the baseline is stabilized and then a 20 .OMEGA. calibration check is performed. 20 .OMEGA. is equal to 4 blocks on the graphic produced by the computer software. The agonist (haTRAP) is added by an adjustable volume pipette (5-25 μl) and the aggregation curve is recorded for 10 minutes. Maximum aggregation in 6 minutes following agonist addition is the value recorded.

In Vitro Platelet Aggregation Procedure:

Platelet aggregation studies can be performed according to the method of Bednar et al. (Bednar, B., Condra, C., Gould, R. J., and Connolly, T. M., Throm. Res., vol. 77, pp. 453-463 (1995)). Blood can be obtained from healthy human subjects who are aspirin free for at least 7 days by venipuncture using ACD as anticoagulant.

Platelet rich plasma can be prepared by centrifugation at 100×g for 15 minutes at 15° C. Platelets can be pelleted at 3000×g and washed twice in buffered saline containing 1 mM EGTA and 20 μg/ml apyrase to inhibit aggregation. Aggregation can be performed at room temperature in buffered saline supplemented with 0.2 mg/ml human fibrinogen. Test compound and platelets can be preincubated in 96-well flat-bottom plates for 60 minutes. Aggregation can be initiated by adding 0.3 μM haTRAP or 0.1 U/ml thrombin and rapidly vortexing the mixture using a Lab Line Titer Plate Shaker (speed 7). Percent aggregation can be monitored as increasing light transmittance at 405 nm in a Spectromax Plate Reader.

In Vivo Antitumor Procedure:

Tests in the human breast carcinoma model in nude mouse are conducted according to the procedure reported in S. Even-Ram et. al., Nature Medicine, 4, 8, pp. 909-914 (1988).

Toll-Like Receptor

In Vitro Screening of a Library of Small Molecules for Inhibitors of Human TLR9 (and Similarly for TLR3)

Candidate small molecules for initial screening can be obtained from a commercially available library of 880 off-patent small molecules selected for structural diversity and proven bioavailability in humans (Prestwick Chemical Library). Human embryonic kidney HEK293 cells stably transfected with a human TLR9 (hTLR9) expression vector can be incubated overnight in the presence of 50 nM CpG ODN 2006 (i.e., the EC50 concentration of ODN 2006) and selected small molecule candidate compounds at different concentrations ranging from $5\times10^{-7}$ M to $5\times10^{-5}$ M. TLR9 activity can be assayed in terms of induction of a 6×NF-.kappa.B-luciferase reporter construct cotransfected in the cells. Results can be measured as fold induction over baseline luciferase activity measured in the absence of ODN 2006 and compared to fold induction over baseline in the presence of the EC50 concentration of ODN 2006 alone. From this initial screening a number of small molecules can be identified as lead compounds and can be categorized by structure and activity. Additional screening can be performed in like manner using additional small molecules selected from another library or specifically prepared for this purpose.

The method is described in greater detail as follows. The cells for each individual cell clone (hTLR3-NF.kappa.B-293, hTLR7-NF.kappa.B-293, hTLR8-NF.kappa.B-293 and hTLR9-NF.kappa.B-293) can be counted and seeded one day before the stimulation at $1.5\times10^4$ cells per well in 96-well cell culture plates. To become adherent the cells can be incubated after seeding overnight at 37° C. in 5% $CO_2$ humidified air.

The screen for each compound can be performed at the same time for all of the receptors TLR3, TLR7, TLR8 and TLR9. Up to fifteen test compounds, each assayed in duplicate at each of three different final concentrations (0.5 μg/ml, 5 μg/ml, and 50 μg/ml), can be used for 16 h cell stimulation on a single multiwell culture plate. A 4× final concentration master plate can be created to prepare the different test compounds before they can be added to the cells.

For TLR3, candidate small molecules for initial screening can be identified in an assay except HEK293 cells can be stably transfected with a human TLR3 (hTLR3) expression vector and incubated overnight in the presence of 2.5 μg/ml poly(I:C) (EC50 of poly(I:C) for TLR3) and selected small molecule candidate compounds at different concentrations ranging from $5\times10^{-7}$ M to $5\times10^{-5}$ M. TLR3 activity can be assayed in terms of induction of a 6×NF-.kappa.B-luciferase reporter construct cotransfected in the cells. Results can be expressed as fold induction over baseline luciferase activity measured in the absence of poly(I:C). From this initial screening a number of small molecules can be identified as lead compounds and can be categorized by structure and activity. Additional screening can be performed in like manner using additional small molecules selected from another library or specifically prepared for this purpose. Scoring is reported as above but as applied to TLR3.

Controls can be added as duplicates individually for each cell clone on the cell culture plate. Positive controls can be used as follows (final concentrations): 50 μg/ml poly(I:C) for hTLR3-NF.kappa.B-293; 8 μM resiquimod (R848) for hTLR7-NF.kappa.B-293; 30 μM R848 for hTLR8-NF.kappa.B-293; and 2.5 µM CpG-ODN 2006 for hTLR9-NF.kappa.B-293. Media alone can be used as negative control. After addition of controls and small molecules, the cell clones can be additionally stimulated with the EC50 concentration of the appropriate receptor-specific ligand.

To calculate the baseline response to the EC50 concentration of the appropriate receptor-specific ligand, wells H3 and H6 did not receive receptor-specific ligand. The mean value of wells H2 and H5 (each with cells and EC50 concentration of the appropriate receptor-specific ligand) divided by the mean of wells H3 and H6 (each with cells alone) yielded the baseline response (i.e., fold induction of luciferase activity) to EC50 concentration of the appropriate receptor-specific ligand.

After 16 h stimulation the supernatant can be removed and the cells treated with lysis buffer and stored at −80° C. before measuring.

In Vivo Screening of Selected Small Molecules

Experimental mice are administered known amounts of candidate small molecules and a source of PAMP or other suitable TLR ligand, e.g., CpG nucleic acid. Negative control mice receive the source of PAMP or other suitable TLR ligand, e.g., CpG nucleic acid, alone. After an appropriate period, blood samples are obtained from control and experimental mice and evaluated for serum concentration of cytokine using a suitable method, e.g., enzyme-linked immunosorbent assay (ELISA). Alternatively or in addition, peripheral blood mononuclear cells (PBMC) are isolated from both groups of animals and assessed for expression of activation marker using a suitable technique such as fluorescence activated cell sorting (FACS). Control and experimental results are compared in pairwise fashion. Reduced expression of activation marker or reduced concentration of cytokine in an experimental animal compared to a negative control animal indicates the small molecule inhibits TLR-mediated signaling in response to a ligand for the TLR. Increased expression of activation marker or increased concentration of cytokine in an experimental animal compared to a negative control animal indicates the small molecule promotes TLR-mediated signaling in response to a ligand for the TLR.

In Vivo Screening of Selected Small Molecules

Experimental mice are administered candidate small molecules. Negative control mice are administered carrier alone. After administration or small molecule or carrier alone, PBMC are isolated and then exposed in vitro to CpG nucleic acid under conditions in which the PBMC, in the absence of small molecule, are stimulated to express an activation marker such as CD86 or secrete a product such as cytokine (e.g., IFN-α, IL-6, TNF-α) or chemokine (e.g., IP-10). The expression of the activation marker or the secretion of the product is quantified using FACS, ELISA, or other suitable method, and comparison is made between results obtained with and without the small molecule. Reduced expression of activation marker or reduced concentration of cytokine in an experimental animal compared to a negative control animal indicates the small molecule inhibits TLR-mediated signaling in response to a ligand for the TLR. Increased expression of activation marker or increased concentration of cytokine in an experimental animal compared to a negative control animal indicates the small molecule promotes TLR-mediated signaling in response to a ligand for the TLR.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having a structure according to the formula:

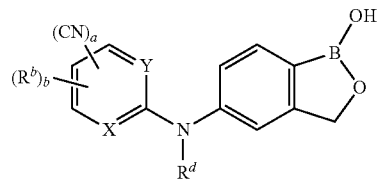

wherein

X is selected from the group consisting of CH, C(CN), $CR^b$ and N;

Y is selected from the group consisting of CH, C(CN), $CR^b$ and N;

a is 0 or 1;

b is 0 or 1;

$R^4$ is selected from the group consisting of H, unsubstituted $C_1$-$C_6$ alkyl, $COR^{10}$, and —C(O)O$R^{10}$, wherein $R^{10}$ is H or unsubstituted $C_1$-$C_6$ alkyl;

with the proviso that when X or Y is C(CN), then a is 0;

with the proviso that when X or Y is $CR^b$, then b is 0;

with the proviso that X and Y cannot both be C(CN);

with the proviso that X and Y cannot both be $CR^b$;

$R^b$ is selected from the group consisting of $OR^4$, $NR^4R^5$, $SR^4$, —S(O)$R^4$, —S(O)$_2R^4$, —S(O)$_2NR^4R^5$, —C(O)$R^4$, —C(O)O$R^4$, —C(O)N$R^4R^5$, nitro, cyano, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein $R^4$ and $R^5$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl with the proviso that $R^4$ and $R^5$, together with the atoms to which they are attached, are optionally combined to form a 5- to 7-membered substituted or unsubstituted heterocycloalkyl ring or a salt thereof.

2. The compound of claim 1, or a salt thereof, having a structure which is

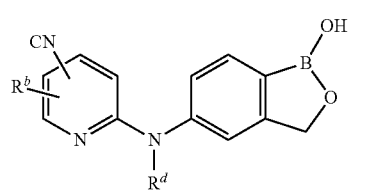

or

-continued

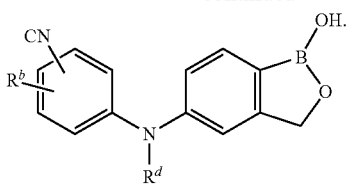

3. The compound of claim 1, or a salt thereof, having a structure which is

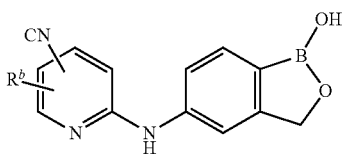

or

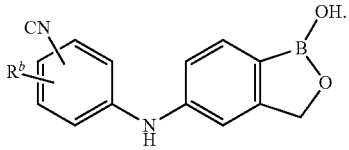

4. The compound of claim 1, or a salt thereof, having a structure which is

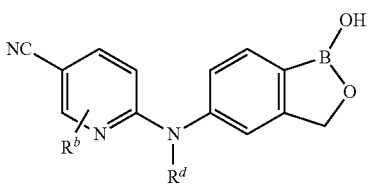

or

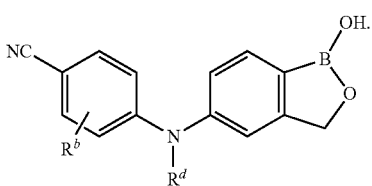

5. The compound of claim 1, or a salt thereof, having a structure which is

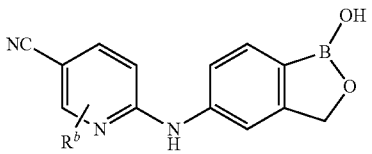

or

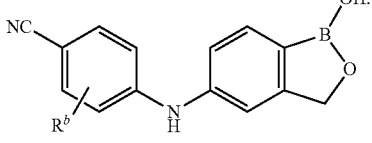

6. The compound of claim 1, or a salt thereof, having a structure which is

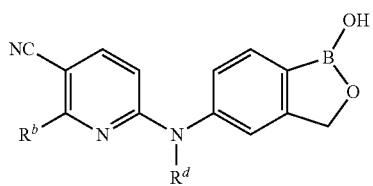

or

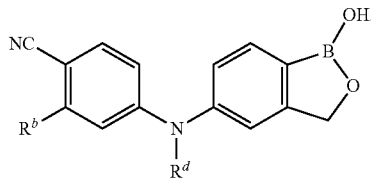

7. The compound of claim 1, or a salt thereof, having a structure which is

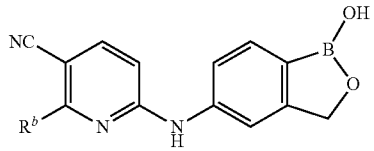

or

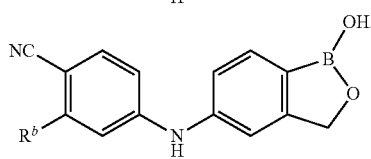

8. The compound of claim 1, or a salt thereof, wherein $R^b$ is $OR^4$, and $R^4$ is selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

9. The compound of claim 1, or a salt thereof, wherein $R^b$ is $OR^4$, and $R^4$ is substituted or unsubstituted alkyl.

10. The compound of claim 1, or a salt thereof, having a structure which is selected from the group consisting of

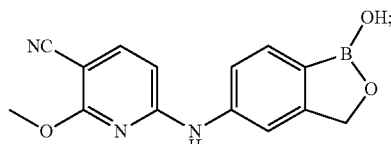

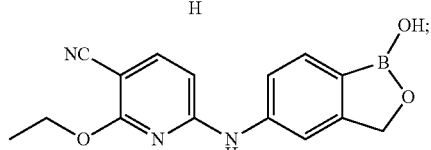

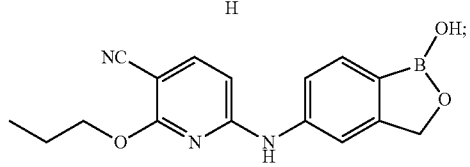

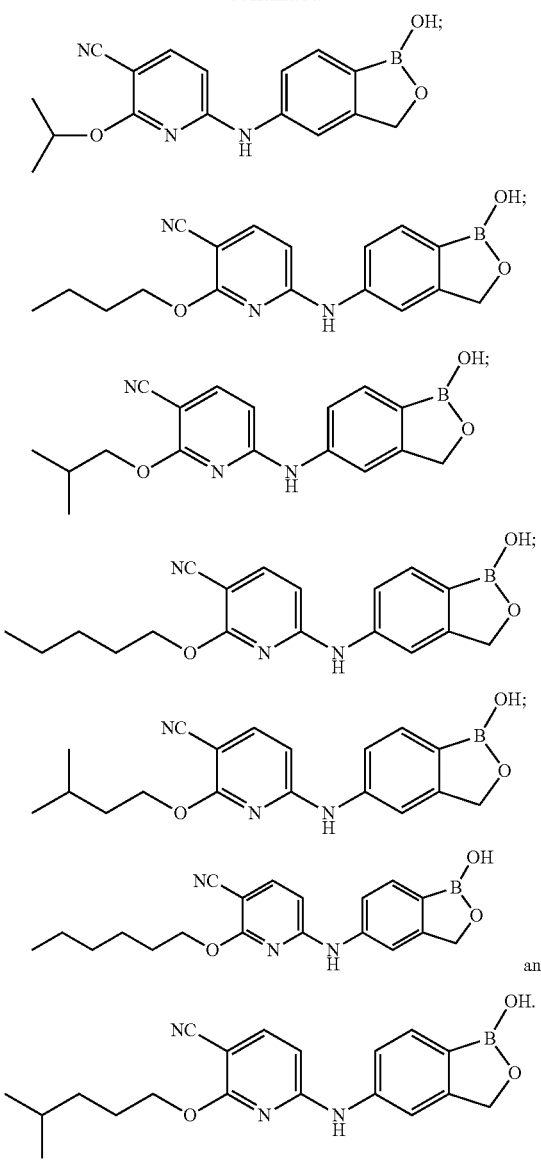

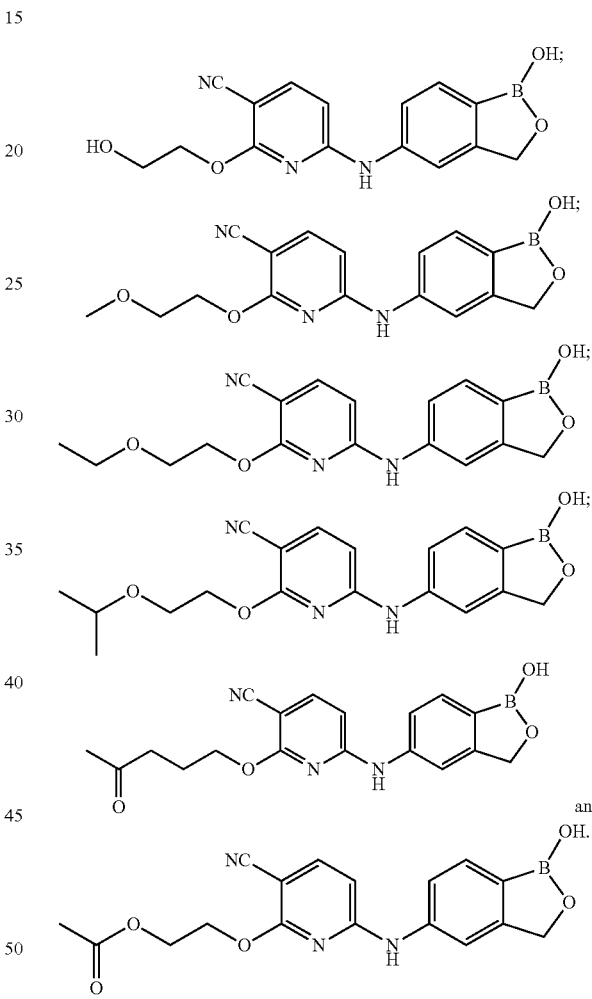

13. The compound of claim 1, or a salt thereof, wherein $R^b$ is $OR^4$, and $R^4$ is substituted or unsubstituted heteroalkyl.

14. The compound of claim 1, or a salt thereof, having a structure which is selected from the group consisting of

11. The compound of claim 1, or a salt thereof, wherein $R^b$ is $OR^4$, and $R^4$ is cycloalkylsubstituted alkyl.

12. The compound of claim 1, or a salt thereof, having a structure which is selected from the group consisting of

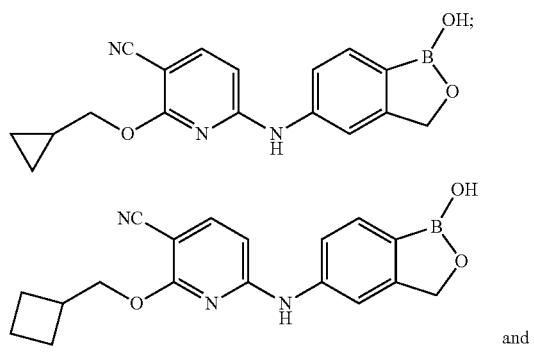

15. The compound of claim 1, or a salt thereof, wherein $R^b$ is $NR^4R^5$, and $R^4$ and $R^5$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

16. The compound of claim 1, or a salt thereof, wherein $R^b$ is $NHR^5$, and $R^5$ is selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

17. The compound of claim 1, or a salt thereof, wherein $R^b$ is $NHR^5$, and $R^5$ is substituted or unsubstituted heteroalkyl.

18. The compound of claim 1, or a salt thereof, having a structure which is selected from the group consisting of

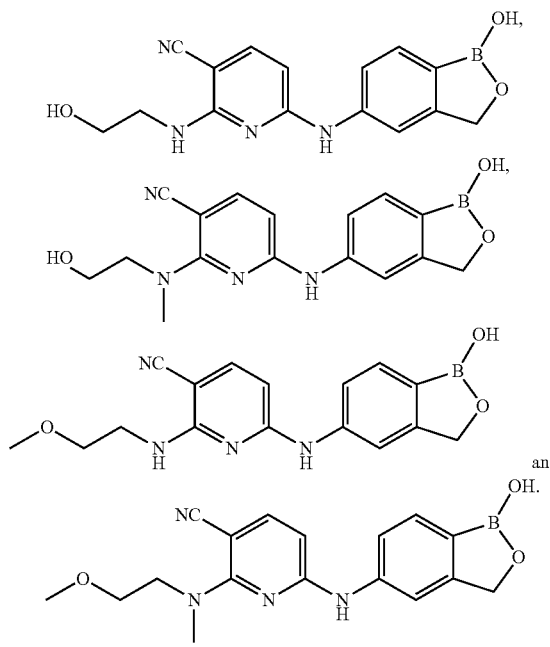

and

19. A pharmaceutical formulation comprising:
(a) the compound of claim 1, or a pharmaceutically acceptable salt thereof;
(b) a pharmaceutically acceptable excipient.

20. The formulation of claim 19, wherein the formulation is in a unit dosage form.

21. The formulation of claim 19, wherein the formulation is for oral or topical use.

22. The compound of claim 1, or a salt thereof, having a structure which is selected from the group consisting of

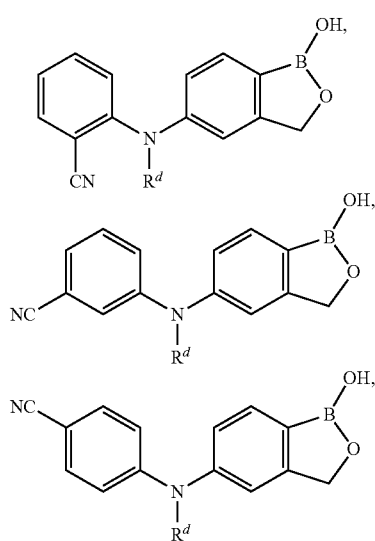

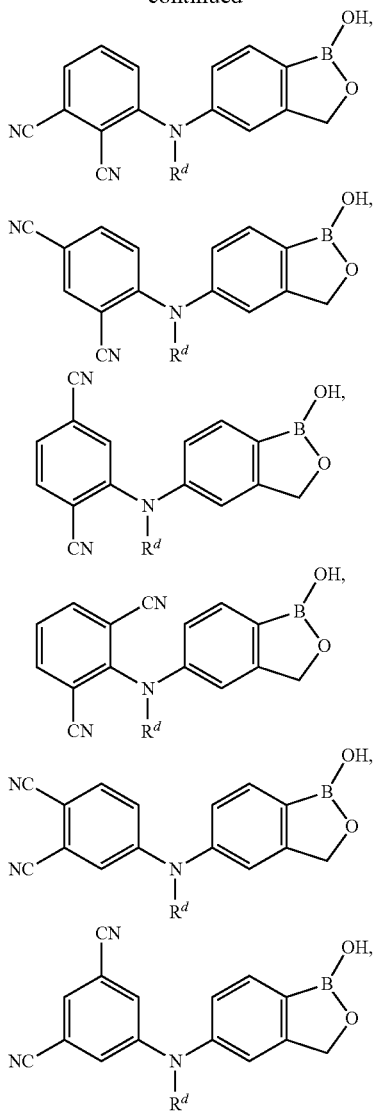

wherein $R^d$ is selected from the group consisting of H, unsubstituted $C_1$-$C_6$ alkyl, $COR^{10}$, and —$C(O)OR^{10}$,
wherein $R^{10}$ is selected from the group consisting of H and unsubstituted $C_1$-$C_6$ alkyl.

23. The compound of claim 1, or a salt thereof, wherein $R^d$ is H or methyl or ethyl or propyl or isopropyl or butyl or isobutyl or secbutyl or t-butyl.

24. The compound of claim 1, or a salt thereof, wherein $R^d$ is H.

25. The compound of claim 1, or a salt thereof, having a structure which is selected from the group consisting of

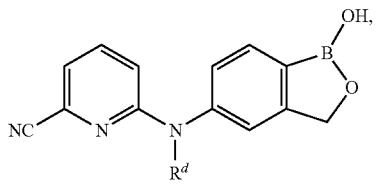

-continued

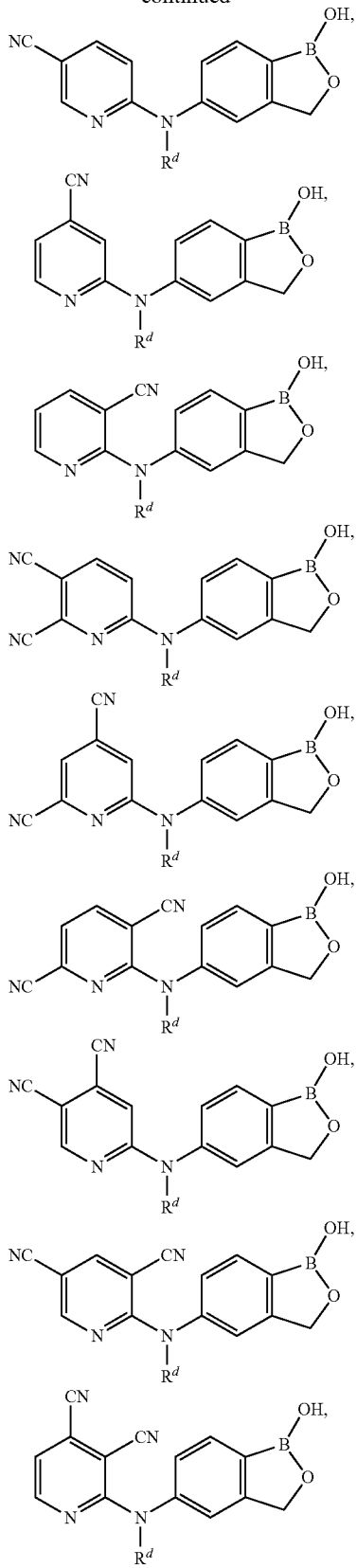

wherein R$^d$ is selected from the group consisting of H, unsubstituted C$_1$-C$_6$ alkyl, COR$^{10}$, and —C(O)OR$^{10}$.

26. The compound of claim 1, or a salt thereof, wherein R$^d$ is H or methyl or ethyl or propyl or isopropyl or butyl or isobutyl or secbutyl or t-butyl.

27. The compound of claim 1, or a salt thereof, wherein R$^d$ is H.

28. The compound of claim 1, or a salt thereof, having a structure which is

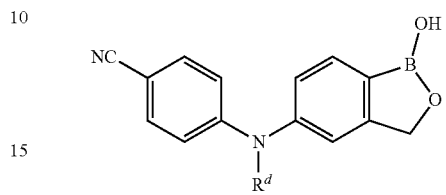

wherein
  R$^d$ is selected from the group consisting of H, unsubstituted C$_1$-C$_6$ alkyl and —C(O)OR$^{10}$,
    wherein R$^{10}$ is H or unsubstituted C$_1$-C$_6$ alkyl.

29. The compound of claim 1, or a salt thereof, having a structure which is

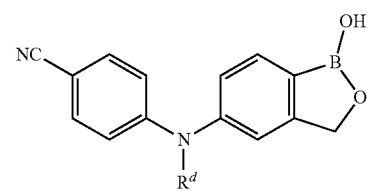

wherein
  R$^{10}$ is selected from the group consisting of methyl, ethyl, propyl, isopropyl, butyl, isobutyl, sec-butyl, pentyl, isopentyl, cyclopentyl, hexyl, isohexyl and cyclohexyl.

30. The compound of claim 1, or a salt thereof, having a structure which is

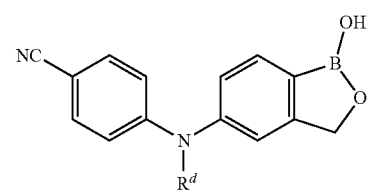

wherein
  R$^d$ is selected from the group consisting of methyl, ethyl, propyl, isopropyl, butyl, pentyl and hexyl.

31. The compound of claim 1, or a salt thereof, having a structure which is

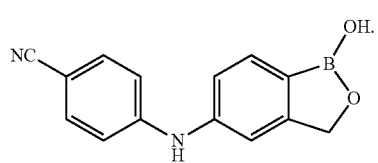 [SMILES: N#Cc1ccc(Nc2ccc3c(c2)COB3O)cc1]

32. The compound of claim 1, or a salt thereof, having a structure which is

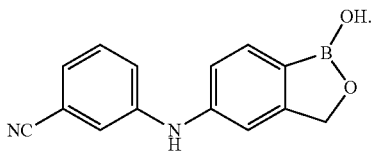

33. The compound of claim 1, or a salt thereof, having a structure which is

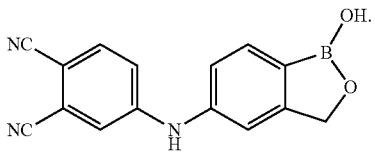 [SMILES: N#Cc1ccc(Nc2ccc3c(c2)COB3O)cc1C#N]

34. The compound of claim 1, or a salt thereof, having a structure which is

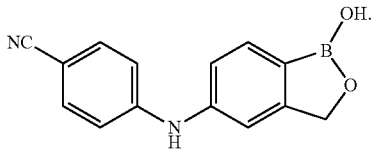 [SMILES: N#Cc1ccc(Nc2ccc3c(c2)COB3O)cc1]

35. The compound of claim 1, or a salt thereof, having a structure which is

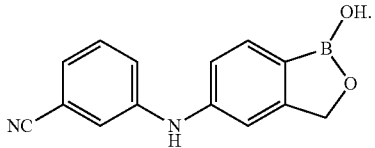 [SMILES: N#Cc1cccc(Nc2ccc3c(c2)COB3O)c1]

36. The compound of claim 1, or a salt thereof, having a structure which is

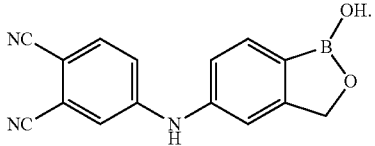 [SMILES: N#Cc1ccc(Nc2ccc3c(c2)COB3O)cc1C#N]

37. The compound of claim 2, or a salt thereof, wherein $R^b$ is $OR^4$, and $R^4$ is unsubstituted alkyl.

38. The compound of claim 2, or a salt thereof, wherein $R^b$ is $OR^4$, and $R^4$ is unsubstituted $C_1$ or $C_2$ or $C_3$ alkyl.

39. The compound of claim 2, or a salt thereof, wherein $R^b$ is $OR^4$, and $R^4$ is unsubstituted $C_4$ or $C_5$ or $C_6$ alkyl.

40. The compound of claim 2, or a salt thereof, wherein $R^b$ is $OR^4$, and $R^4$ is alkyl substituted with one or two or three halogen.

41. The compound of claim 2, or a salt thereof, wherein $R^b$ is —$O(CH_2)_{m1}OC(O)R^{4d}$, wherein m1 is a number selected from 1 or 2 or 3 or 4 or 5 or 6 and $R^{4d}$ is unsubstituted $C_1$ or $C_2$ or $C_3$ or $C_4$ or $C_5$ or $C_6$ alkyl.

42. The compound of claim 2, or a salt thereof, wherein $R^b$ is —$O(CH_2)_{m1}C(O)R^{4d}$, wherein m1 is a number selected from 1 or 2, or 3 or 4 or 5 or 6 and $R^{4d}$ is unsubstituted $C_1$ or $C_2$ or $C_3$ or $C_4$ or $C_5$ or $C_6$ alkyl.

43. The compound of claim 2, or a salt thereof, wherein $R^b$ is —$O(CH_2)_{m1}C(O)OR^{4d}$, wherein m1 is a number selected from 1 or 2 or 3 or 4 or 5 or 6 and $R^{4d}$ is H or unsubstituted.

44. The compound of claim 2, or a salt thereof, wherein $R^b$ is —$O(CH_2)_{m2}C(O)NR^{4e}R^{4f}$, wherein m2 is a number selected from 1 or 2 or 3 or 4 or 5 or 6, and $R^{4e}$ is H or unsubstituted alkyl, $R^{4f}$ is H or unsubstituted alkyl, or $R^{4e}$ and $R^{4f}$, together with the nitrogen to which they are attached, are optionally joined to form a substituted or unsubstituted 4 to 8 membered ring.

45. The compound of claim 2, or a salt thereof, wherein $R^b$ is $OR^4$, wherein $R^4$ is substituted or unsubstituted cycloalkyl.

46. The compound of claim 2, or a salt thereof, wherein $R^b$ is $OR^4$, wherein $R^4$ is unsubstituted cyclopentyl or unsubstituted cyclohexyl.

47. The compound of claim 2, or a salt thereof, wherein $R^b$ is $OR^4$, wherein $R^4$ is alkyl substituted with unsubstituted alkoxy.

48. The compound of claim 2, or a salt thereof, wherein $R^b$ is —$O(CH_2)_{m5}OR^{30}$, wherein m5 is 1 or 2 or 3 or 4 or 5 or 6 and $R^{30}$ is H or unsubstituted alkyl or unsubstituted tetrahydropyran.

49. The compound of claim 48, or a salt thereof, wherein $R^{30}$ is unsubstituted $C_1$ or $C_2$ or $C_3$ or $C_4$ or $C_5$ or $C_6$ alkyl.

50. The compound of claim 2, or a salt thereof, wherein $R^b$ is —$C(O)R^4$, wherein $R^4$ is H or unsubstituted $C_1$ or $C_2$ or $C_3$ or $C_4$ or $C_5$ or $C_6$ alkyl.

51. The compound of claim 2, or a salt thereof, wherein $R^b$ is alkyl substituted with hydroxy.

52. The compound of claim 2, or a salt thereof, wherein $R^b$ is alkyl substituted with carboxy or ester.

53. The compound of claim 2, or a salt thereof, wherein $R^b$ is —$(CH_2)_{m1}C(O)OR^{4a}$, wherein m1 is a number selected from 1 or 2 or 3 or 4 or 5 or 6 and $R^{4a}$ is H or unsubstituted alkyl.

54. The compound of claim 2, or a salt thereof, wherein $R^b$ is —$CH_2C(O)OR^{4a}$, wherein $R^{4a}$ is H or methyl or ethyl or t-butyl.

55. The compound of claim 2, or a salt thereof, wherein $R^b$ is alkyl substituted with amino.

56. The compound of claim 2, or a salt thereof, wherein $R^b$ is —$(CH_2)_{m7}NR^{4a}R^{4b}$, wherein m7 is selected from the group consisting of 1, 2, 3, 4, 5 and 6 and $R^{4a}$ is selected from the group consisting of H, unsubstituted alkyl and formyl, $R^{4b}$ is selected from the group consisting of H, unsubstituted alkyl and formyl, or $R^{4a}$ and $R^{4b}$, together with the nitrogen to which they are attached, are optionally joined to form a substituted or unsubstituted 4 to 8 membered ring.

57. The compound of claim 2, or a salt thereof, wherein $R^b$ is selected from the group consisting of —$NH(CH_2)_2OH$, —$NH(CH_2)_2OCH_3$, —$NHCH_3$, —$NHC(CH_3)_3$, —$NH(CH_2)Ph$, and —$NH(CH_2)_2O(CH_2)Ph$.

58. The compound of claim 2, or a salt thereof, wherein $R^b$ is selected from the group consisting of —$N(CH_3)_2$, —$N(CH_3)(CH_2)_2OH$, —$N(CH_3)(CH_2)_2OCH_3$, —$NHCH_3$, —$NHC(CH_3)_3$, —$NH(CH_2)Ph$, and —$NH(CH_2)_2O(CH_2)Ph$.

59. The compound of claim 1, or a salt thereof, having a structure which is

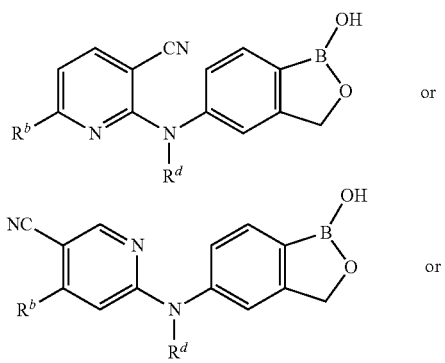

-continued

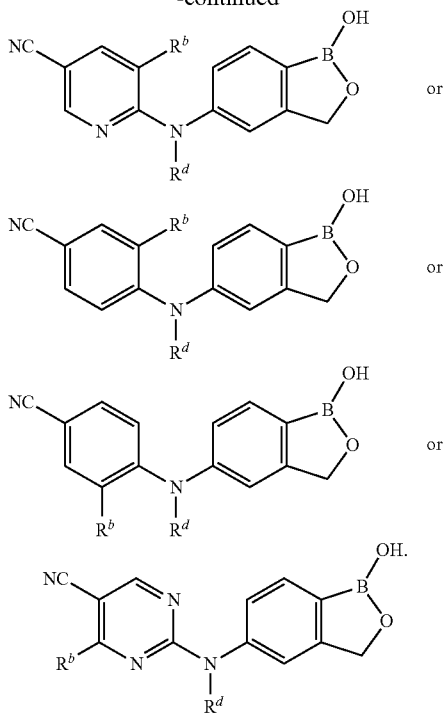

or or or

60. The compound of claim 1, or a salt thereof, having a structure which is

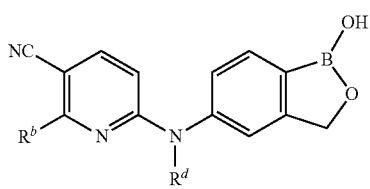

wherein
R$^b$ is OR$^4$
R$^4$ is unsubstituted C$_1$ or C$_2$ or C$_3$ alkyl or unsubstituted C$_4$ or C$_5$ or C$_6$ alkyl or
—O(CH$_2$)$_{m1}$C(O)R$^{4d}$, wherein m1 is a number selected from 1 or 2 or 3 or 4 or 5 or 6 and R4d is unsubstituted C$_1$ or C$_2$ or C$_3$ or C$_4$ or C$_5$ or C$_6$ alkyl or
—O(CH$_2$)$_{m5}$OR$^{30}$, wherein m5 is 1 or 2 or 3 or 4 or 5 or 6 and R$^{30}$ is unsubstituted C$_1$ or C$_2$ or C$_3$ or C$_4$ or C$_5$ or C$_6$ alkyl.

61. The compound of claim 1, or a salt thereof, having a structure which is

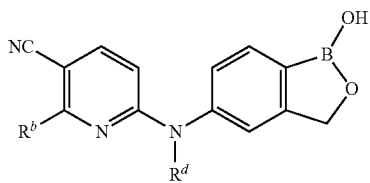

wherein
R$^b$ is unsubstituted C$_2$ alkyl.

62. The compound of claim 1, or a salt thereof, having a structure which is

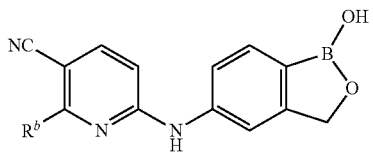

wherein
R$^b$ is —O(CH$_2$)$_3$C(O)CH$_3$.

63. The compound of claim 1, or a salt thereof, having a structure which is

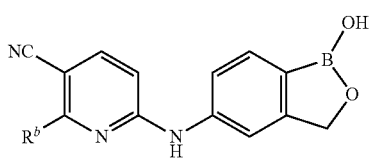

wherein
R$^b$ is —O(CH$_2$)$_2$OCH(CH$_3$)$_2$.

64. The compound of claim 1, or a salt thereof, having a structure which is

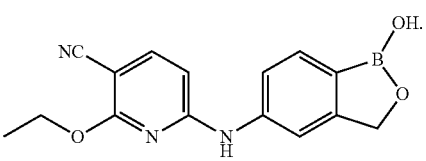 [SMILES: CCOc1nc(Nc2ccc3c(c2)COB3O)ccc1C#N]

65. The compound of claim 1, or a salt thereof, having a structure which is

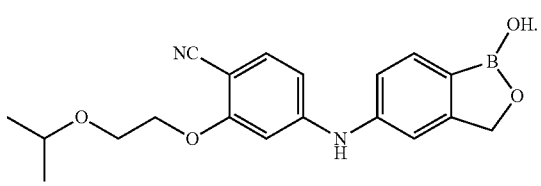 [SMILES: CC(C)OCCOc1cc(Nc2ccc3c(c2)COB3O)ccc1C#N]

66. The compound of claim 1, or a salt thereof, having a structure which is

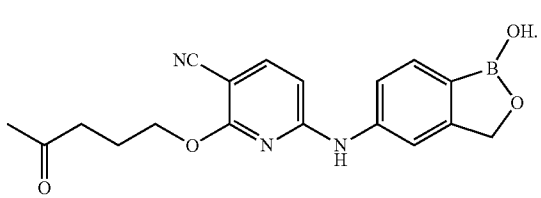 [SMILES: CC(=O)CCCOc1nc(Nc2ccc3c(c2)COB3O)ccc1C#N]

* * * * *